(12) United States Patent
Luo et al.

(10) Patent No.: US 12,054,548 B2
(45) Date of Patent: Aug. 6, 2024

(54) ANTI-PD-L1 ANTIBODIES AND USE THEREOF

(71) Applicant: Adagene Inc., Grand Cayman (KY)

(72) Inventors: Peizhi Luo, Jiangsu (CN); Fangyong Du, Jiangsu (CN); Guizhong Liu, Jiangsu (CN); Yan Li, Jiangsu (CN)

(73) Assignee: Adagene, Inc., Gran Cayman (KY)

( * ) Notice: Subject to any disclaimer, the term of this patent is extended or adjusted under 35 U.S.C. 154(b) by 946 days.

(21) Appl. No.: 17/043,454

(22) PCT Filed: Mar. 29, 2019

(86) PCT No.: PCT/CN2019/080496
§ 371 (c)(1),
(2) Date: Sep. 29, 2020

(87) PCT Pub. No.: WO2019/185035
PCT Pub. Date: Oct. 3, 2019

(65) Prior Publication Data
US 2021/0122824 A1   Apr. 29, 2021

(30) Foreign Application Priority Data

Mar. 29, 2018  (WO) ................ PCT/CN2018/081096

(51) Int. Cl.
| | | |
|---|---|---|
| *C07K 16/00* | (2006.01) | |
| *A61K 39/395* | (2006.01) | |
| *A61K 51/10* | (2006.01) | |
| *A61P 35/00* | (2006.01) | |
| *C07K 16/28* | (2006.01) | |
| *G01N 33/574* | (2006.01) | |
| *A61K 39/00* | (2006.01) | |

(52) U.S. Cl.
CPC .... *C07K 16/2827* (2013.01); *A61K 39/39541* (2013.01); *A61K 51/1027* (2013.01); *A61P 35/00* (2018.01); *C07K 16/2878* (2013.01); *G01N 33/57492* (2013.01); *A61K 2039/507* (2013.01); *C07K 2317/33* (2013.01); *C07K 2317/52* (2013.01); *C07K 2317/732* (2013.01); *C07K 2317/92* (2013.01); *G01N 2333/70532* (2013.01)

(58) Field of Classification Search
CPC ............ C07K 16/2827; C07K 16/2878; C07K 2317/33; C07K 2317/52; C07K 2317/732; C07K 2317/92; A61K 39/39541; A61K 51/1027; A61K 2039/507; A61P 35/00; G01N 33/57492
See application file for complete search history.

(56) References Cited

U.S. PATENT DOCUMENTS

2016/0108123 A1*  4/2016  Freeman .................. A61N 5/10
                                                         435/69.6

FOREIGN PATENT DOCUMENTS

| WO | 2016061142 A1 | 4/2016 |
|---|---|---|
| WO | 2017215590 A1 | 12/2017 |

OTHER PUBLICATIONS

International Search Report in International Application No. PCT/CN2019/080496 mailed Aug. 16, 2019.

* cited by examiner

*Primary Examiner* — Lei Yao
(74) *Attorney, Agent, or Firm* — Quarles & Brady LLP

(57) ABSTRACT

The present disclosure provides antibodies that bind to the T-cell co-inhibitor ligand programmed death-ligand1 (PD-L1) protein, and methods of use. In various embodiments of the disclosure, the antibodies are fully human antibodies that bind to PD-L1. In certain embodiments, the present disclosure provides multi-specific antigen-binding molecules comprising a first binding specificity that binds to PD-L1 and a second binding specificity that binds to a tumor cell antigen, an infected cell-specific antigen, or a T-cell co-inhibitor. In some embodiments, the antibodies of the disclosure are useful for inhibiting or neutralizing PD-L1 activity, thus providing a means of treating a disease or disorder such as cancer or viral infection.

11 Claims, 19 Drawing Sheets

Specification includes a Sequence Listing.

ANTI-PD-L1 ANTIBODIES AND USE THEREOF

CROSS REFERENCE TO RELATED APPLICATIONS

This application is a U.S. National Phase application under 35 U.S.C. 371 of International Application No. PCT/CN2019/080496, filed Mar. 29, 2019, which claims priority to and the benefit of PCT International Application No. PCT/CN2018/081096, filed Mar. 29, 2018, each of which is incorporated herein by reference in their entirety.

FIELD

The present application relates to anti-PD-L1 antibodies or antigen binding fragments thereof, nucleic acid encoding the same, therapeutic compositions thereof, and their use to enhance T-cell function to upregulate cell-mediated immune responses and for the treatment of T cell dysfunctional disorders, such as tumor immunity, and for the treatment of cancer.

BACKGROUND

The ability of T cells to mediate an immune response against an antigen requires two distinct signaling interactions (Viglietta, V. et al. (2007) Neurotherapeutics 4:666-675; Korman, A. J. et al. (2007) Adv. Immunol. 90:297-339). First, an antigen that has been arrayed on the surface of antigen-presenting cells (APC) is presented to an antigen-specific naive CD4$^+$ T cell. Such presentation delivers a signal via the T cell receptor (TCR) that directs the T cell to initiate an immune response specific to the presented antigen. Second, various co-stimulatory and inhibitory signals mediated through interactions between the APC and distinct T cell surface molecules trigger the activation and proliferation of the T cells and ultimately their inhibition.

The immune system is tightly controlled by a network of costimulatory and co-inhibitory ligands and receptors. These molecules provide the second signal for T cell activation and provide a balanced network of positive and negative signals to maximize immune responses against infection, while limiting immunity to self (Wang, L. et al. (Epub Mar. 7, 2011) J. Exp. Med. 208(3):577-92; Lepenies, B. et al. (2008) Endocrine, Metabolic & Immune Disorders—Drug Targets 8:279-288). Examples of costimulatory signals include the binding between the B7.1 (CD80) and B7.2 (CD86) ligands of the APC and the CD28 and CTLA-4 receptors of the CD4 T-lymphocyte (Sharpe, A. H. et al. (2002) Nature Rev. Immunol. 2: 116-126; Lindley, P. S. et al. (2009) Immunol. Rev. 229:307-321). Binding of B7.1 or B7.2 to CD28 stimulates T cell activation, whereas binding of B7.1 or B7.2 to CTLA-4 inhibits such activation (Dong, C. et al. (2003) Immunolog. Res. 28(1):39-48; Greenwald, R. J. et al. (2005) Ann. Rev. Immunol. 23:515-548). CD28 is constitutively expressed on the surface of T cells (Gross, J., et al. (1992) J. Immunol. 149:380-388), whereas CTLA-4 expression is rapidly up-regulated following T-cell activation (Linsley, P. et al. (1996) Immunity 4:535-543).

Other ligands of the CD28 receptor include a group of related B7 molecules, also known as the "B7 Superfamily" (Coyle, A. J. et al. (2001) Nature Immunol. 2(3):203-209; Sharpe, A. H. et al. (2002) Nature Rev. Immunol. 2: 116-126; Collins, M. et al. (2005) Genome Biol. 6:223.1-223.7; Korman, A. J. et al. (2007) Adv. Immunol. 90:297-339). Several members of the B7 Superfamily are known, including B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) Genome Biol. 6:223.1-223.7).

The Programmed Death 1 (PD-1) protein is an inhibitory member of the extended CD28/CTLA-4 family of T cell regulators (Okazaki et al. (2002) Curr Opin Immunol 14: 391779-82; Bennett et al. (2003) J. Immunol. 170:711-8). Other members of the CD28 family include CD28, CTLA-4, ICOS and BTLA. Two cell surface glycoprotein ligands for PD-1 have been identified, Program Death Ligand 1 (PD-L1) and Program Death Ligand 2 (PD-L2). PD-L1 and PD-L2 have been shown to downregulate T cell activation and cytokine secretion upon binding to PD-1 (Freeman et al. (2000) J Exp Med 192: 1027-34; Latchman et al. (2001) Nat Immunol 2:261-8; Carter et al. (2002) Eur J Immunol 32:634-43; Ohigashi et al. (2005) Clin Cancer Res 11:2947-53).

PD-L1 (also known as cluster of differentiation 274 (CD274) or B7 homolog 1 (B7-H1)) is a 40 kDa type 1 transmembrane protein. PD-L1 binds to its receptor, PD-1, found on activated T cells, B cells, and myeloid cells, to modulate activation or inhibition. Both PD-L1 and PD-L2 are B7 homologs that bind to PD-1, but do not bind to CD28 or CTLA-4 (Blank et al. (2005) Cancer Immunol Immunother. 54:307-14). Binding of PD-L1 with its receptor PD-1 on T cells delivers a signal that inhibits TCR-mediated activation of IL-2 production and T cell proliferation. The mechanism involves inhibition of ZAP70 phosphorylation and its association with CD3C (Sheppard et al. (2004) FEB S Lett. 574:37-41). PD-1 signaling attenuates PKC-Θ activation loop phosphorylation resulting from TCR signaling, necessary for the activation of transcription factors NF-κB and AP-1, and for production of IL-2. PD-L1 also binds to the costimulatory molecule CD80 (B7-1), but not CD86 (B7-2) (Butte et al. (2008) Mol Immunol. 45:3567-72).

Expression of PD-L1 on the cell surface has been shown to be upregulated through IFN-γ stimulation. PD-L1 expression has been found in many cancers, including human lung, ovarian and colon carcinoma and various myelomas, and is often associated with poor prognosis (Iwai et al. (2002) PNAS 99:12293-7; Ohigashi et al. (2005) Clin Cancer Res 11:2947-53; Okazaki et al. (2007) Intern. Immun. 19:813-24; Thompson et al. (2006) Cancer Res. 66:3381-5). PD-L1 has been suggested to play a role in tumor immunity by increasing apoptosis of antigen-specific T-cell clones (Dong et al. (2002) Nat Med 8:793-800). It has also been suggested that PD-L1 might be involved in intestinal mucosal inflammation and inhibition of PD-L1 suppresses wasting disease associated with colitis (Kanai et al. (2003) J Immunol 171:4156-63).

Given the importance of immune checkpoint pathways in regulating an immune response, the need exists for developing novel agents that modulate the activity of immunoinhibitory proteins, such as PD-L1, thus leading to activation of the immune system. Such agents can be used, e.g., for cancer immunotherapy and treatment of other conditions, such as chronic infection.

SUMMARY

The present disclosure provides for anti-PD-L1 antibodies, including nucleic acid encoding and compositions containing such antibodies, and for their use to enhance T-cell function to upregulate cell-mediated immune responses and for the treatment of T cell dysfunctional disorders, including infection (e.g., acute and chronic) and tumor immunity.

In one aspect, provided herein is an isolated antibody, or antigen-binding fragment thereof, comprising one or more of the following HVR_L1, HVR_L2, and/or HRV_L3, or comprising all three of HVR_L1, HVR_L2, and HRV_L3 (or a sequence having at least 85% sequence identity thereto):

(1) an HVR_L1 having the amino acid sequence selected from the group consisting of

```
                                    (SEQ ID NO: 1)
(a) RASQX1X2X3X4X5LA
wherein:
X1: G S

X2: I V

X3: E G S

X4: K P S

X5: F W Y (SEQ ID NO: 2)
(b) RASX1SVDFX2GX3SFLX4
wherein:
X1: E Q

X2: F H Y

X3: I K

X4: A D (SEQ ID NO: 3)
(c) X1ASQX2IPX3FLX4
wherein:
X1: Q R

X2: D S T

X3: K S T

X4: A N (SEQ ID NO: 4)
(d) RASQGX1SX2X3LA
wherein:
X1: I V

X2: P S

X3: W Y
and (SEQ ID NO: 5)
(e) RASQX1IPSFLN
wherein:
X1: S T
```

(2) an HVR_L2 having the amino acid sequence selected from the group consisting of

```
                                    (SEQ ID NO: 6)
(a) DASX1X2X3X4GX5
wherein:
X1: N S

X2: L R

X3: A E

X4: S T

X5: I V
```

```
                                    (SEQ ID NO: 7)
(b) AASX1LQSGV
wherein:
X1: S T
and (SEQ ID NO: 8)
(c) DASNX1X2TGX3
wherein:
X1: L R

X2: A E

X3: I V
```

(3) HVR_L3 having the amino acid sequence selected from the group consisting of:

```
                                    (SEQ ID NO: 9)
(a) YCQQYDX1WPYT
wherein:
X1: A H S Y (SEQ ID NO: 10)
(b) YCQX1YX2SWPRX3FT
wherein:
X1: H Q

X2: G I S T V

X3: G L Q R V (SEQ ID NO: 11)
(c) YCQQYDX1WPYT
wherein:
X1: A S
and (SEQ ID NO: 12)
(d) YCQHYX1SWPRQFT
wherein:
X1: I T
```

In some embodiments, the antibody or fragment thereof can include an HVR_L1 having the amino acid sequence selected from the group consisting of SEQ ID NOs: 13-39 and 94-102, an HVR_L2 having the amino acid sequence selected from the group consisting of SEQ ID NOs: 40-66 and 103-111, and/or an HVR_L3 having the amino acid sequence selected from the group consisting of SEQ ID NOs: 67-93 and 112-120.

In certain embodiments, the antibody or fragment thereof can include an HVR_L1 having the amino acid sequence selected from the group consisting of SEQ ID NOs: 13-39, an HVR_L2 having the amino acid sequence selected from the group consisting of SEQ ID NOs: 40-66, and/or an HVR_L3 having the amino acid sequence selected from the group consisting of SEQ ID NOs: 67-93. In embodiments, such antibody or fragment thereof is cross-reactive with human and monkey PD-L1.

In certain embodiments, the antibody or fragment thereof can have an HVR_L1 having the amino acid sequence selected from the group consisting of SEQ ID NOs: 94-102, an HVR_L2 having the amino acid sequence selected from the group consisting of SEQ ID NOs: 103-111, and/or an HVR_L3 having the amino acid sequence selected from the group consisting of SEQ ID NOs: 112-120. In embodiments, such antibody or fragment thereof is cross-reactive with human, monkey and mouse PD-L1.

In certain embodiments, the antibody or fragment thereof can have a VL having the amino acid sequence selected from the group consisting of SEQ ID NOs:121-125:

(SEQ ID NO: 121)
DIQLTQSPSSLSASVGDRVTITCRASQX1X2X3X4X5LAWYQQKPGKAPK

WYDASX6X7X8X9GX10PSRFSGSGSGTDFTLTISSLQPEDFATYYCQQY

DX11WPYTFGQGTKVEIKR
wherein:
X1: G S

X2: I V

X3: E G S

X4: K P S

X5: F W Y

X6: N S

X7: L R

X8: A E

X9: S T

X10: I V

X11: A S Y (SEQ ID NO: 122)
DIQLTQSPSSLSASVGDRVTITCRASX1SVDFX2GX3SFLX4WYQQKPGK

APKLLIYDASX5X6X7X8GX9PSRFSGSGSGTDFTLTISSLQPEDFATYY

CQQYDX10WPYTFGQGTKVEIKR
wherein:
X1: E Q

X2: F H Y

X3: I K

X4: A D

X5: N S

X6: L R

X7: A E

X8: S T

X9: I V

X10: A H S Y (SEQ ID NO: 123)
DIQLTQSPSSLSASVGDRVTITCX1ASQX2IPX3FLX4WYQQKPGKAPKL

LIYAASX5LQSGVPSRFSGSGSGTDFTLTISSLQPEDFATYYCQX6YX7S

WPRX8FTFGQGTKVEIKR
wherein:
X1: Q R

X2: D S T

X3: K S T

X4: A N

X5: S T

X6: H Q

X7: G I S T V

X8: G L Q R V (SEQ ID NO: 124)
DIQLTQSPSSLSASVGDRVTITCRASQGX1SX2X3LAWYQQKPGKAPKLL

IYDASNX4X5TGX6PSRFSGSGSGTDFTLTISSLQPEDFATYYCQQYDX7

WPYTFGQGTKVEIKR
wherein:
X1: I V

X2: P S

X3: W Y

X4: L R

X5: A E

X6: I V

X7: A S (SEQ ID NO: 125)
DIQLTQSPSSLSASVGDRVTITCRASQX1IPSFLNWYQQKPGKAPKLLIY

AASSLQSGVPSRFSGSGSGTDFTLTISSLQPEDFATYYCQHYX2SWPRQF

TFGQGTKVEIKR
wherein:
X1: S T

X2: I T

In some embodiments, the antibody or fragment thereof can have a VL having the amino acid sequence selected from the group consisting of SEQ ID NOs: 121-122 and 124, which can be cross-reactive with human and monkey PD-L1.

In some embodiments, the antibody or fragment thereof can have a VL having the amino acid sequence selected from the group consisting of SEQ ID NOs: 123 and 125, which can be cross-reactive with human, monkey and mouse PD-L1.

In various embodiments, the antibody or fragment thereof can further include an HVR_H1 having the amino acid sequence selected from the group consisting of SEQ ID NOs: 164 and 167, an HVR_H2 having the amino acid sequence selected from the group consisting of SEQ ID NOs: 165 and 168, and/or an HVR_H3 having the amino acid sequence selected from the group consisting of SEQ ID NOs: 166 and 169.

In some embodiments, the antibody or fragment thereof can have a VH having the amino acid sequence selected from the group consisting of SEQ ID NOs: 126-127.

In some embodiments, the antibody or fragment thereof can have a VL having the amino acid sequence selected from the group consisting of SEQ ID NOs: 128-163.

In some embodiments, the antibody or fragment thereof binds human PD-L1 with a $K_D$ of 100 nM or less, preferably 50 nM or less, more preferably 10 nM or less, as measured by surface plasmon resonance.

A further aspect relates to a pharmaceutical composition comprising one or more of the antibody or fragment thereof disclosed herein and a pharmaceutically acceptable carrier.

Another aspect relates to a method for treating a cancer and/or reducing tumor growth in a subject in need thereof, comprising administering a therapeutically effective amount of one or more of the antibody or fragment thereof disclosed herein to said subject.

Also provided herein is a theranostic composition comprising one or more of the antibody or fragment thereof disclosed herein and a diagnostic imaging agent, wherein preferably the diagnostic imaging agent is a radionuclide label.

A further aspect relates to a method for diagnosing and treating a cancer in a subject in need thereof, comprising administering an effective amount of the theranostic composition disclosed herein to said subject.

Also provided herein is a method of detecting PD-L1 in vitro, comprising fixing a cell with paraformaldehyde, and immunostaining the cell with one or more of the antibody or fragment thereof disclosed herein.

In certain embodiments, the antibody or antigen-binding fragment thereof has a sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to one or more of SEQ ID NOs: 1-169.

In a still further aspect, any one of the antibodies disclosed herein can further comprise a human or murine constant region. The human constant region may be selected from the group consisting of IgG1, IgG2, IgG3, and IgG4. In some embodiments, the human constant region is IgG1. The murine constant region may be selected from the group consisting of IgG1, IgG2A, IgG2B, and IgG3. In some embodiments, the murine constant region is IgG2A.

In a further aspect, provided herein is an isolated antibody or antigen-binding fragment thereof that competes for binding to human PD-L1 protein with a reference antibody selected from any of the anti-PD-L1 antibodies disclosed herein. In some embodiments, the antibody or fragment has one or more of the following properties: (a) binds monomeric PD-L1 with a binding dissociation equilibrium constant ($K_D$) of less than about 310 pM as measured in a surface plasmon resonance assay at 37° C.; (b) binds monomeric human PD-L1 with a $K_D$ less than about 180 pM in a surface plasmon resonance assay at 25° C.; (c) binds dimeric human PD-L1 with a $K_D$ of less than about 15 pM as measured in a surface plasmon resonance assay at 37° C.; and (d) binds dimeric human PD-L1 with a $K_D$ less than about 8 pM in a surface plasmon resonance assay at 25° C.

In a still further aspect, a nucleic acid encoding any one of the sequences disclosed herein is provided. The nucleic acid may further comprise a vector suitable for expression of the nucleic acid encoding any of the previously described anti-PD-L1 antibodies. In some embodiments, the vector is provided along with or inside a host cell suitable for expression of the nucleic acid. The host cell may be a eukaryotic cell or a prokaryotic cell. In some embodiments, the eukaryotic cell is a mammalian cell, such as Chinese Hamster Ovary (CHO).

Also provided herein is a bispecific or multi-specific antibody or antigen-binding molecule or fragment thereof comprising a first antigen-binding specificity that binds specifically to PD-L1 and a second antigen-binding specificity that binds specifically to an antigen selected from, e.g., a tumor-cell-specific antigen, an antigen specific to a virally-infected cell, and a T-cell co-inhibitor. The tumor cell-specific antigen may be one or more of CA9, CA125, melanoma-associated antigen (MAGE), carcinoembryonic antigen (CEA), vimentin, tumor-M2-PK, prostate-specific antigen (PSA), MART-1, and CA19-9. The virally-infected cell may be infected with a virus selected from one or more of human immunodeficiency virus (HIV), hepatitis C virus (HCV), human papilloma virus (HPV), lymphocytic choriomeningitis virus (LCMV), and simian immunodeficiency virus (SW). The T-cell co-inhibitor may be one or more of LAG 3, TIM3, B7-1, CTLA-4, BTLA, CD28, 2B4, LY108, TIGIT, ICOS, and CD160. In some embodiments, the bi- or multi-specific antibodies can be used to treat a cancer selected from one or more of renal cell carcinoma, colorectal cancer, ovarian cancer, prostate cancer, breast cancer, colon cancer, non-small-cell lung cancer and melanoma. In certain embodiments, the bi- or multi-specific antibodies can be used to treat viral infection caused by a virus selected from one or more of HIV, HPV, HBV, HCV, LCMV and SIV.

In a still further aspect, the disclosure provides for a process of making an anti-PD-L1 antibody or antigen binding fragment thereof, comprising culturing a host cell containing a nucleic acid encoding any of the previously described anti-PD-L1 antibodies or antigen-binding fragment thereof in a form suitable for expression, under conditions suitable to produce such antibody or fragment, and recovering the antibody or fragment.

In a still further aspect, the disclosure provides for an anti-PD-L1 composition comprising an anti-PD-L1 antibody or antigen binding fragment thereof (or a bi- or multi-specific antibody) as provided herein and at least one pharmaceutically acceptable carrier.

In a still further aspect, the disclosure provides an article of manufacture comprising a container enclosing a therapeutically effective amount of an anti-PD-L1 composition disclosed herein and a package insert indicating use for the treatment of a T-cell dysfunctional disorder.

In a still further aspect, the disclosure provides for an article of manufacture comprising any of the above described anti-PD-L1 compositions in combination with at least one BNCA molecules. In one aspect, the BNCA molecules is an antibody, antigen binding antibody fragment, BNCA oligopeptide, BNCA RNAi or BNCA small molecule. In another aspect, the B7 negative costimulatory molecule is selected from the group consisting of: CTLA-4, PD-1, PD-L1, PD-L2, B7.1, B7-H3 and B7-H4.

In a still further aspect, provided herein is an article of manufacture comprising any of the above described anti-PD-L1 compositions in combination with a chemotherapeutic agent. In one embodiment, the chemotherapeutic agent is gemcitabine.

In a still further aspect, the disclosure provides for an article of manufacture comprising any of the above described anti-PD-L1 antibodies in combination with one or more agonists of a positive costimulatory molecule. In one embodiment, a positive costimulatory molecule is a B7 family costimulatory molecule. In another embodiment the positive costimulatory molecule is selected from the group consisting of: CD28, CD80, CD86, ICOS/ICOSL. In yet another embodiment, the positive costimulatory molecule is a TNFR family costimulatory molecule. In a further embodiment, the TNFR costimulatory molecule is selected form the group consisting of: OX40/OX40L, 4-1BB/4-1BBL, CD27/CD27L, CD30/CD30L and HVEM/LIGHT, and soluble fragments, constructs and agonist antibodies thereof.

In a still further aspect, the disclosure provides for an article of manufacture comprising any of the above described anti-PD-L1 antibodies (or a bi- or multi-specific antibodies) in combination with one or more antibiotics. In one aspect, the antibiotic is selected from the group consisting of an anti-viral agent, anti-bacterial agent, anti-fungal agent, anti-protozoan agent.

In some embodiments, the anti-viral agent is selected from the group consisting of reverse transcriptase inhibitors, protease inhibitors, integrase inhibitors, entry or fusion inhibitors, maturation inhibitors, viral release inhibitors, immune response enhancers, anti-viral synergistic enhancers, vaccines, hepatic agonists and herbal therapies. In yet another aspect, the combination comprises one or more categories of anti-viral agents.

In a still further aspect, the disclosure provides for an article of manufacture comprising any of the above described anti-PD-L1 antibodies (or a bi- or multi-specific antibodies) in combination with one or more vaccines.

In a still further aspect, the disclosure provides for a method of enhancing T-cell function comprising administering an effective amount of any of the above described anti-PD-L1 antibodies or compositions (or a bi- or multi-specific antibodies). In one embodiment, the anti-PD-L1 antibody or composition renders dysfunctional T-cells non-dysfunctional.

In a still further aspect, the disclosure provides for a method of treating a T-cell dysfunctional disorder comprising administering a therapeutically effective amount of any of the above described anti-PD-L1 antibodies or compositions (or a bi- or multi-specific antibodies). In one specific embodiment, the T-cell dysfunctional disorder is infection or tumor immunity. The infection can be acute or chronic. In some embodiments, the chronic infection is persistent, latent or slow. In yet another embodiment, the chronic infection results from a pathogen selected from the group consisting of bacteria, virus, fungi and protozoan. In a further embodiment, the pathogen level in the host is reduced.

In a still further embodiment, the method further comprises treatment with a vaccine. In a still further embodiment, the method further comprises treatment with an antibiotic. In a still further embodiment, the pathogen is a bacterium, and the method further comprises the administration of an antibacterial agent. In a still further embodiment, the bacterium is selected from the group consisting of: *Mycobacterium* spp., *Salmonella* spp., *Listeria* spp., *Streptococcus* spp., *Haemophilus* spp., *Neisseria* spp., *Klebsiella* spp., *Borrelia* spp., *Bacterioides fragillis*, *Treponema* spp., and *Helicobacter pylori*. In a still further embodiment, the pathogen is a virus, and the method further comprises the administration of an anti-viral agent. In a still further aspect, the virus is selected from the group consisting of: hepatitis-B, -C, herpes simplex virus-I, -II, human immunodeficiency virus-I, -II, cytomegalovirus, Eppstein Barr virus, human papillomavirus, human T lymphotrophic viruses, -I, -II, varicella zoster. In a still further embodiment, the pathogen is a fungus, and the method further comprises the administration of an anti-fungal agent. In a still further embodiment, the disorder is selected from the group consisting of: aspergilosis, blastomycosis, candidiasis albicans, coccidioiodmycosis immitis, histoplasmosis, paracoccidioiomycosis, microsporidiosis. In a still further embodiment, the pathogen is a protozoan, and the method further comprises the administration of an anti-protozoan agent. In a still further embodiment, the disorder is selected from the group consisting of: leishmaniasis, plasmodiosis (i.e., malaria), cryptosporidiosis, toxoplasmosis, trypanosomiasis, and helminth infections, including those resulting from trematodes (e.g., schistosomiasis), cestodes (e.g., echinococcosis) and nemotodes (e.g., trchinosis, ascariasis, filariosis and strongylodiosis).

In a still further aspect, the T-cell dysfunctional disorder is tumor immunity. In a still further embodiment, the PD-L1 antibody or composition is combined with a treatment regimen further comprising a traditional therapy selected from the group consisting of: radiation therapy, chemotherapy, targeted therapy, immunotherapy, hormonal therapy, angiogenesis inhibition and palliative care. In a still further specific embodiment, the chemotherapy treatment is selected from the group consisting of: gemcitabine, cyclophosphamide, doxorubicin, paclitaxel, cisplatin. In a still further specific embodiment, the tumor immunity results from a cancer selected from the group consisting of: breast, lung, colon, ovarian, melanoma, bladder, kidney, liver, salivary, stomach, gliomas, thyroid, thymic, epithelial, head and neck cancers, gastric, and pancreatic cancer.

Also provided herein is a pharmaceutical composition comprising the anti-PD-L1 antibody or fragment thereof disclosed herein, an anti-CD137 antibody or antigen-binding fragment thereof as disclosed in PCT International Application No. PCT/CN2017/098332 incorporated herein by reference in its entirety, and a pharmaceutically acceptable carrier. The anti-CD137 antibody or fragment thereof can comprise the following HVR_H1, HVR_H2, HVR_H3, HVR_L1, HVR_L2, and/or HRV_L3:

```
(1) an HVR_H1 having amino acid sequence selected
from the group consisting of:
                                          (SEQ ID NO.: 172)
(a) X1TFX2X3YX4IHWV
wherein:
X1: F or Y X2: S or T X3: G or N or S X4: A or G or W wherein preferably X2 is S and/or X4 is W;

(SEQ ID NO.: 173)
(b) YSIX1SGX2X3WX4WI
wherein:
X1: S or T

X2: H or Y

X3: H or Y

X4: A or D or G or N or S or T wherein preferably X4 is A, D, G, N, or S;
and
                                          (SEQ ID NO.: 174)
(c) FSLSTX1GVX2VX3WI
wherein:
X1: G or S X2: A or G X3: A or G or S or T wherein preferably X3 is A or G or S;

(2) an HVR_H2 having amino acid sequence selected
from the group consisting of:
                                          (SEQ ID NO.: 175)
(a) LALIDWX1X2DKX3YSX4SLKSRL
wherein:
X1: A or D or Y X2: D or G X3: R or S or Y X4: P or T;

(SEQ ID NO.: 176)
(b) IGX1IYHSGX2TYYX3PSLKSRV
wherein:
X1: D or E

X2: N or S

X3: N or S;
``` and (c) VSX1ISGX2GX3X4TYYADSVKGRF  (SEQ ID NO.: 177)
wherein:
X1: A or G or S or V or Y X2: A or D or S or Y X3: D or G or S X4: S or T wherein preferably X1 is G or S or V or Y;

(3) an HVR_H3 having the amino acid sequence of
 (SEQ ID NO.: 178)
ARX1GX2X3X4VX5GDWFX6Y
wherein:
X1: E or G X2: E or S X3: D or T X4: A or T or V X5: A or I or L or T or V X6: A or D or G;

(4) an HVR_L1 having the amino acid sequence of
 (SEQ ID NO.: 179)
X1A5QX2X3X4X5X6X7X8
wherein:
X1: Q or R X2: D or G or S X3: I or V X4: G or R or S or T X5: P or R or S or T X6: A or D or F or S or V or Y X7: L or V X8: A or G or N wherein preferably X6 is A or F or S or V or Y
and/or X8 is A or G;

(5) an HVR_L2 having the amino acid sequence of
 (SEQ ID NO.: 180)
X1ASX2X3X4X5GX6
wherein:
X1: A or D X2: N or S or T X3: L or R X4: A or E or Q X5: S or T X6: I or V wherein preferably X2 is N or S;

(6) HVR_L3 having amino acid sequence selected from the group consisting of:
 (SEQ ID NO.: 181)
(a) YCQQX1YX2X3X4T
wherein:
X1: A or G or S or Y X2: Q or S or Y X3: I or L or T or Y X4: I or S or V or W;

wherein preferably:
X1: A or G

X2: S or Y

X3: I or L or T

X4 is W;
and
 (SEQ ID NO.: 182)
(b) YCX1QX2X3X4X5PX6T
wherein:
X1: E or Q

X2: P or S or Y

X3: D or L or S or T or Y

X4: D or E or H or S or T

X5: D or L or T or W

X6: L or P or R or V.

A further aspect relates to a method for treating a cancer and/or reducing tumor growth in a subject in need thereof, comprising administering a therapeutically effective amount of the anti-PD-L1 antibody or fragment thereof disclosed herein and the above-mentioned anti-CD137 antibody or antigen-binding fragment thereof to said subject.

DETAILED DESCRIPTION

Figure 1A:
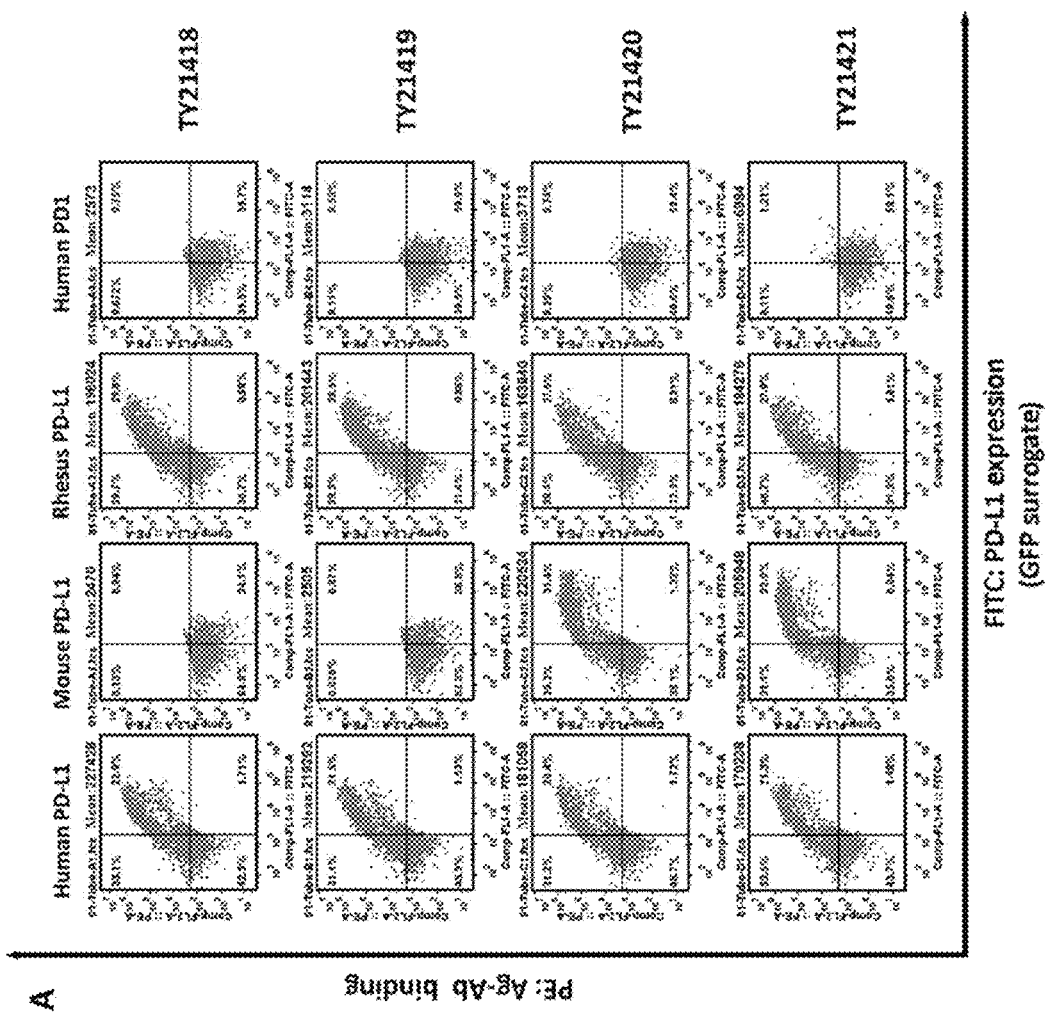
FIG. 1 shows flow cytometry-based binding assays of the exemplary antibodies to human, monkey and mouse PD-L1 expressed on mammalian cell surface. It also shows the binding specificity of the exemplary antibodies to PD-L1, but not to other immune checkpoint molecules as indicated at top of the panel.
Figure 1B:
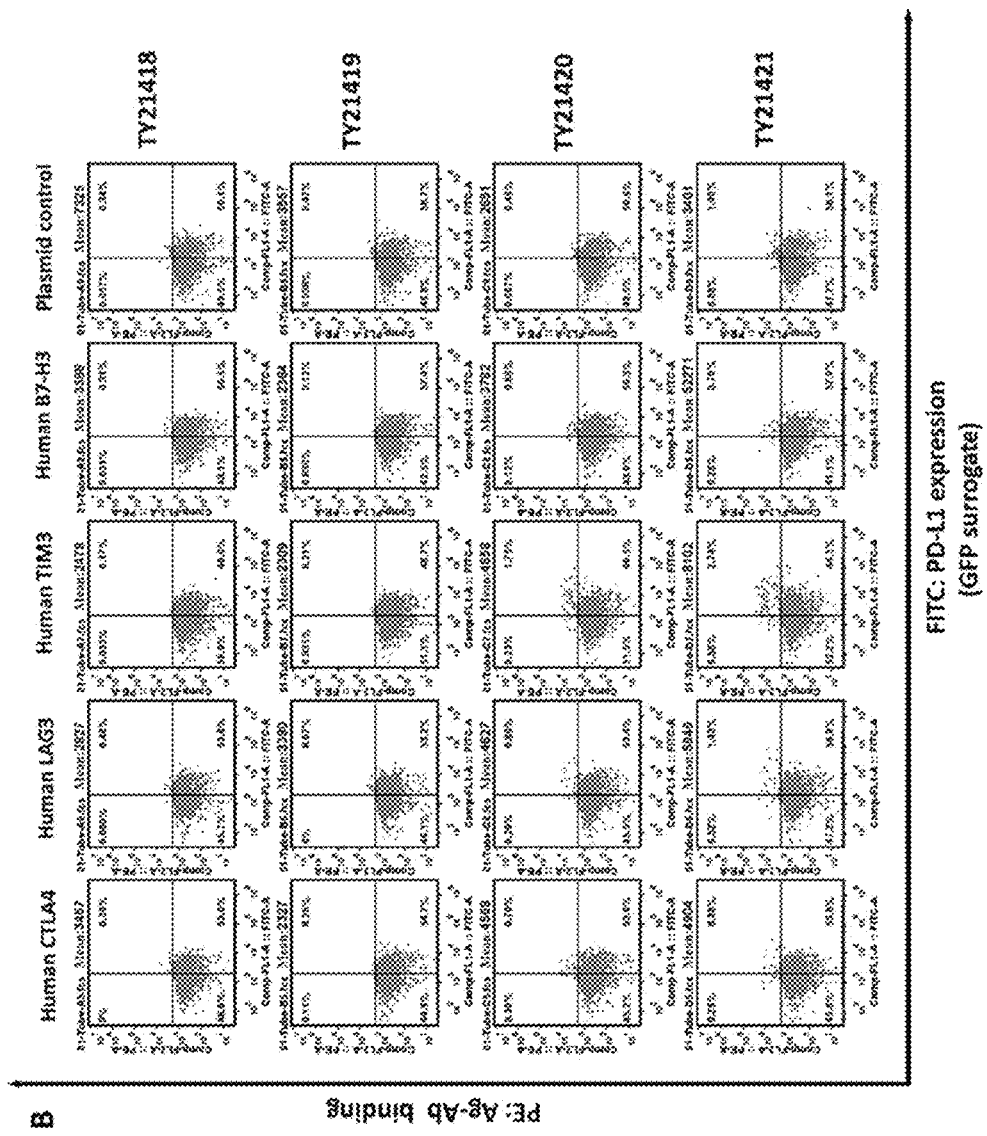
Figure 1C:
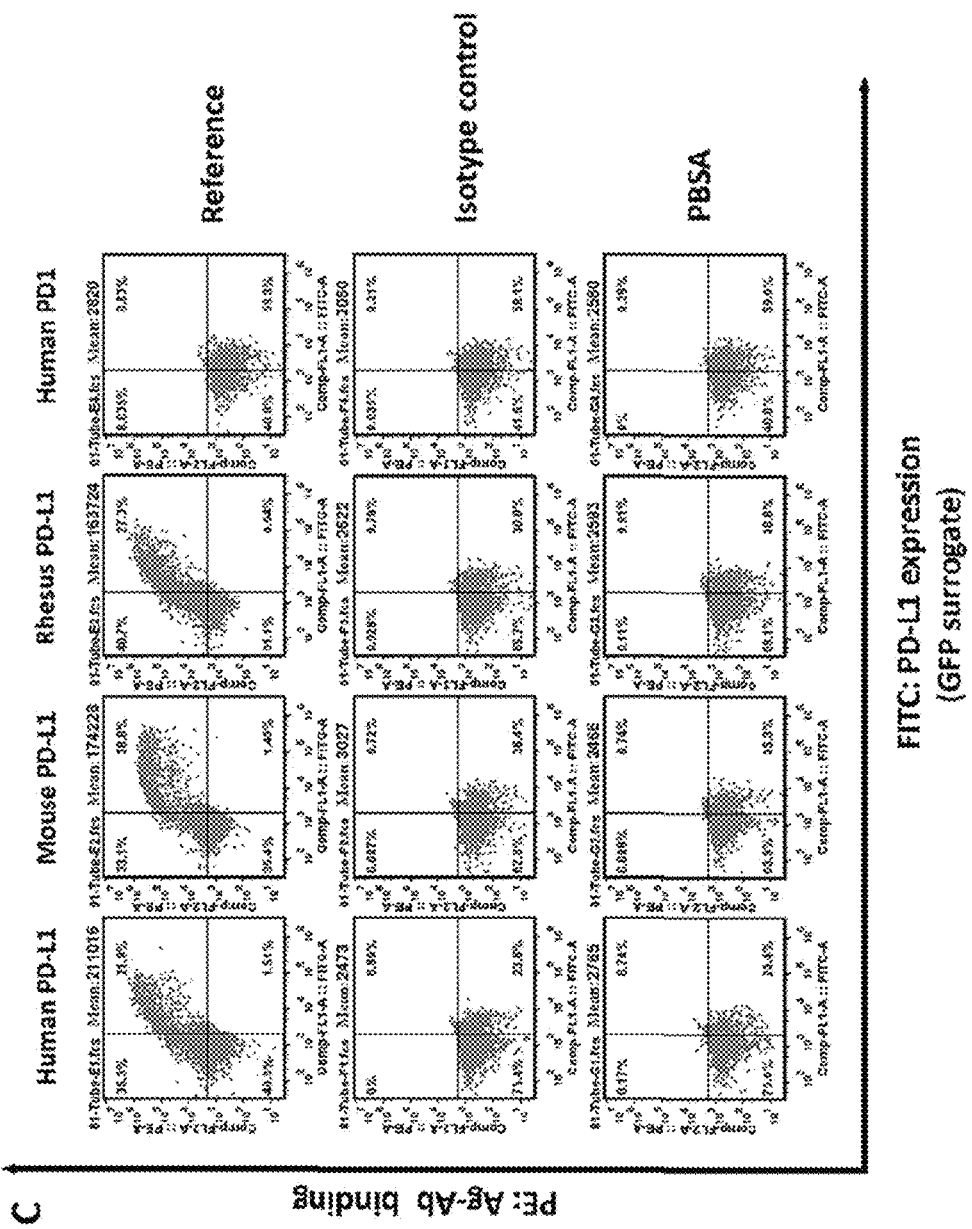
Figure 1D:
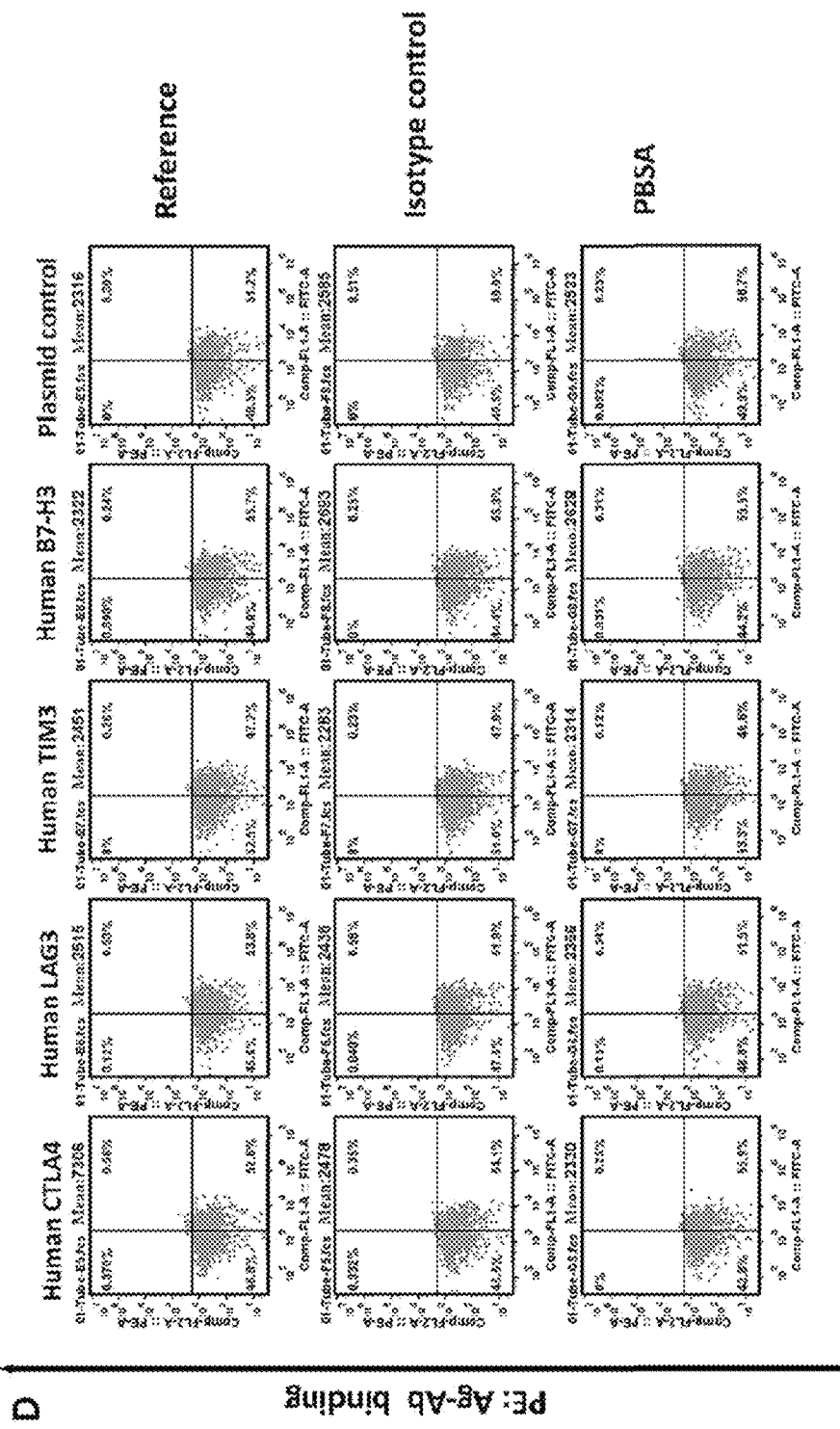

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds 1987, and periodic updates); PCR: The Polymerase Chain Reaction, (Mullis et al., ed., 1994); A Practical Guide to Molecular Cloning (Perbal Bernard V., 1988); Phage Display: A Laboratory Manual (Barbas et al., 2001).

Mechanisms of host immunity, including lymphocyte development and activation, T-cells and their function, the immune response, co-stimulation by the immunoglobulin superfamily (including the B7.1(CD80)/B7.2(CD86)-CD28/CTLA-4(CD152) T-cell costimulatory pathway, ICOS/ICOSL signaling, the PD-1 pathway, etc.) and TNFR family costimulators are reviewed in U.S. Pat. No. 8,217,419 at columns 11-24, which is incorporated by reference in its entirety. The programmed death-1/programmed death ligand-1 (PD-1/PD-L1) pathway and their implications in cancer therapy are reviewed by, e.g., Ohaegbulam et al., Human cancer immunotherapy with antibodies to the PD-1 and PD-L1 pathway, Trends in Molecular Medicine, Volume 21, Issue 1, pp. 24-33, January 2015 (DOI: dx.doi.org/10.1016/j.molmed.2014.10.009) and Dolan et al., PD-1 Pathway Inhibitors: Changing the Landscape of Cancer Immunotherapy, Cancer Control, July 2014, Vol. 21, No. 3, pp. 231-237, which references are incorporated by reference in their entirety.

In one aspect, the present disclosure provides anti-PD-L1 antibodies such that the antagonism of signaling through PD-L1, including blocking PD-L1 from interacting with PD-1, thereby preventing PD-L1 from sending a negative co-stimulatory signal to T-cells and other antigen presenting cells is likely to enhance immunity in response to infection (e.g., acute and chronic) and tumor immunity. In addition, the anti-PD-L1 antibodies of the present disclosure, may be combined with antagonists of other components of PD-1:PD-L1 signaling, for example, anti-PD-1 and anti-PD-L2 antibodies.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

As used herein, the following terms and phrases are intended to have the following meanings:

The articles "a" and "an" are used herein to refer to one or to more than one (i.e., to at least one) of the grammatical object of the article. By way of example, "an element" means one element or more than one element.

As used herein, the term "about" means the usual error range for the respective value readily known to the skilled person in this technical field, e.g., within 20%, more preferably within 10% and most preferably within 5%.

The term "theranostic" refers to a dual-function agent that combines diagnostic and therapeutic capabilities. For example, the theranostic can combine the modalities of therapy and diagnostic imaging. In certain embodiments, the theranostic agent described herein delivers a therapeutic drug and diagnostic imaging agent at the same time within the same dose. By combining these features in one drug, the theranostic agent can overcome the undesirable differences in biodistribution and selectivity that currently exists between distinct imaging and therapeutic agents. Moreover, in this aspect, the theranostic agent of the present disclosure gives the physician the ability to image the cancer and monitor the tumor, the delivery kinetics, and the effectiveness of the therapeutic drug in one package and as a result fine-tune the therapy and dose thereof to the individual patient. In some embodiments, the theranostic can be radionuclide-labeled agents (e.g., the antibodies disclosed herein) that specifically permit diagnosis of disease (e.g., cancer) in a subject and then use identical or closely related agents to treat the disease.

"Dysfunction" in the context of immune dysfunction, refers to a state of immune reduced responsiveness to antigenic stimulation. The term includes the common elements of both exhaustion and/or anergy in which antigen recognition may occur, but the ensuing immune response is ineffective to control infection or tumor growth.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from CD8+ T-cells, increased proliferation, increased antigen responsiveness (e.g., viral or pathogen clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

"Chronic infection" refers to an infection in which an infectious agent (e.g., pathogens such as viruses, bacteria, protozoan parasites, fungi, or the like) has induced an immune response in the infected host, but has not been cleared or eliminated from that host as during an acute infection. Chronic infections may be persistent, latent, or slow. While acute infections are typically resolved by the immune system within a few days or weeks (e.g., influenza), persistent infections can persist at a relatively low level for months, years, decades, or a lifetime (e.g., Hepatitis B). In contrast, a latent infection is characterized by a long period of asymptomatic activity punctuated by a period of rapidly increasing high grade infection and elevated pathogen levels (e.g., herpes simplex). Finally, a slow infection is one characterized by a gradual and continuous increase in disease symptoms, such as a long period of incubation followed by a protracted and progressive clinical course beginning after the onset of clinical symptoms. Unlike latent and persistent infections, slow infection may not begin with an acute period of viral multiplication (e.g., picornaviruses infection, visnavirus, scrapie, Creutzfeldt-Jakob disease). Exemplary infectious agents capable of inducing a chronic infection include viruses (e.g., cytomegalovirus, Epstein Barr virus, hepatitis B virus, hepatitis C virus, herpes simplex virus, types I and II, human immunodeficiency virus, types 1 and 2, human papillomavirus, human T lymphotrophic viruses, types 1 and 2, varicella zoster virus and the like), bacteria (e.g., *Mycobacterium tuberculosis, Listeria* spp., *Klebsiella pneumoniae, Streptococcus pneumoniae, Staphylococcus aureus, Borrelia* spp., *Helicobacter pylori*, and the like), protozoan parasites (e.g., *Leishmania* spp., *Plasmodium falciparum, Schistosoma* spp., *Toxoplasma* spp., *Trypanosoma* spp., *Taenia carssiceps* and the like), and fungi (e.g., *Aspergillus* spp., *Candida albicans, Coccidioides immitis, Histoplasma capsulatum, Pneumocystis carinii* and the like). Additional infectious agents include prions or misfolded proteins that affect the brain or of neuron structure by further propagating protein misfolding in these tissues, resulting in the formation of amyloid plaques which cause cell death, tissue damage and eventual death. Example of disease resulting from prion infection include: Creutzfeldt-Jakob disease and its varieties, Gerstmann-Straussler-Scheinker syndrome (GSS), fatal familial insomnia (sFI), kuru, scrapie, Bovine spongiform encephalopathy (BSE) in cattle (aka "mad cow" disease), and various other animal forms of encephalopathy [e.g., transmissible mink encephalopathy (TME), chronic wasting disease (CWD) in white-tailed deer, elk and mule deer, feline spongiform encephalopathy, exotic ungulate encephalopathy (EUE) in nyala, oryx and greater kudu, spongiform encephalopathy of the ostrich].

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

A "B7-negative costimulatory antagonist" ("BNCA") is an agent that decreases, blocks, inhibits, abrogates or interferes with the negative co-stimulatory signal mediated by or through cell surface proteins expressed on T lymphocytes mediated by a member of the B7 family. In one aspect, a BNCA may either alone, or in combination with the anti-PD-1 antibodies of the disclosure render a dysfunctional T-cell non-dysfunctional. In another aspect, a BNCA may be an agent that inhibits nucleic acid or protein synthesis, expression, signaling, and/or post-expression processing of a B7-negative costimulatory molecule. In yet another aspect, a BNCA is an antibody, antigen binding antibody fragment, BNCA oligopeptide, BNCA RNAi or BNCA small molecule that decreases, blocks, inhibits, abrogates or interferes with signal transduction by a B7-negative costimulatory molecule. Example B7 negative costimulatory molecules includes: CTLA-4, PD-L1, PD-1, B7.1 (expressed on T-cells), PD-L2, B7-H3 and B7-H4.

A "positive costimulatory agonist" is a molecule that increases, enhances, augments or facilitates a co-stimulatory signal mediated by or through cell surface proteins expressed on T lymphocytes. In one aspect, a positive costimulatory molecule can be an extracellular domain, soluble construct or agonist antibody which activates a positive costimulatory pathway. Example positive costimulatory molecules include the B7 superfamily molecules, e.g., B7.1, B7.2, CD28 and ICOS/ICOSL. Additional examples include the TNFR family costimulatory molecules, e.g., OX40/OX40L, 41-BB/41-BBL, CD27/CD27L, CD30/CD30L and HVEM/LIGHT.

A "small molecule" or "small organic molecule" is one that has a molecular weight below about 500 Daltons.

The term "antibiotic" includes any molecule that specifically inhibits or abolishes the growth of micro-organisms, such as virus, bacteria, fungi or protozoa, but is non-lethal to the host at the concentration and dosing interval administered. As used herein, the term antibiotic includes antibacterial agent, anti-viral, agent, anti-fungal agent and anti-protozoan agent. In a specific aspect, an antibiotic is non-toxic to the host at the administered concentration and dosing intervals. Anti-bacterial antibiotics or anti-bacterials can be broadly classified as either bactericidal (i.e., directly kills) or bacteriostatic (i.e., prevents division). Anti-bactericidal antibiotics can be further subclassified as narrow-spectrum (i.e., only affects a small class of subset of bacteria, e.g., gram-negative, etc.) or broad-spectrum (i.e., affects a broad class). Examples of antibiotics include: (i) aminoglycosides, e.g., amikacin, gentamicin, kanamycin, neomycin, netilmicin, streptomycin, tobramycin, paromycin, (ii) ansamycins, e.g., geldanamycin, herbimycin, (iii) carbacephems, e.g., loracarbef, (iv), carbapenems, e.g., ertapenum, doripenem, imipenem/cilastatin, meropenem, (v) cephalosporins (first generation), e.g., cefadroxil, cefazolin, cefalotin, cefalexin, (vi) cephalosporins (second generation), e.g., ceflaclor, cefamandole, cefoxitin, cefprozil, cefuroxime, (vi) cephalosporins (third generation), e.g., cefixime, cefdinir, cefditoren, cefoperazone, cefotaxime, cefpodoxime, ceftazidime, ceftibuten, ceftizoxime, ceftriaxone, (vii) cephalosporins (fourth generation), e.g., cefepime, (viii), cephalosporins (fifth generation), e.g., ceftobiprole, (ix) glycopeptides, e.g., teicoplanin, vancomycin, (x) macrolides, e.g., axithromycin, clarithromycin, dirithromycine, erythromycin, roxithromycin, troleandomycin, telithromycin, spectinomycin, (xi) monobactams, e.g., axtreonam, (xii) penicilins, e.g., amoxicillin, ampicillin, axlocillin, carbenicillin, cloxacillin, dicloxacillin, flucloxacillin, mezlocillin, meticillin, nafcilin, oxacillin, penicillin, peperacillin, ticarcillin, (xiii) antibiotic polypeptides, e.g., bacitracin, colistin, polymyxin B, (xiv) quinolones, e.g., ciprofloxacin, enoxacin, gatifloxacin, levofloxacin, lemefloxacin, moxifloxacin, norfloxacin, orfloxacin, trovafloxacin, (xv) sulfonamides, e.g., mafenide, prontosil, sulfacetamide, sulfamethizole, sulfanilamide, sulfasalazine, sulfisoxazole, trimethoprim, trimethoprim-sulfamethoxazole (TMP-SMX), (xvi) tetracyclines, e.g., demeclocycline, doxycycline, minocycline, oxytetracycline, tetracycline and (xvii) others such as arspenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin or tinidazole.

The term "antiviral agent" includes any molecule that inhibits or abolishes the growth, morbidity and/or survival of viruses. This includes anti-retroviral drugs such as (1) reverse transcriptase inhibitors including for example: (a) nucleoside analog reverse transcriptase inhibitors (NRTIs) (E.g., aciclovir/acyclovir (ZOVIRAX®, ZOVIR®), cidofovir, azidothymidine/zidovudine (AZT, RETROVIR®), didanosine (ddI, VIDEX®; zalcitabine (ddC, HMD®); stavudine (d4T, ZERIT®; lamivudine (3TC, EPIVIR®); abacavir (ZIAGEN®); emtricitabine (EMTRIVA®); brivudine (HELPIN®); entecavir (BARACLUDE®); idoxuridine; viramidine (taribavirin by Valeant Pharmaceuticals), cytidine nucleoside analog polymerase inhibitor PCI-6130, and prodrug variants (e.g., R7128) by Pharmasset/Roche; nucleoside analog inhibitor by Merck/Isis Pharmaceuticals—MK-0608, (b) nucleotide analog reverse transcriptase inhibitors (NtRTIs) (E.g., tenofovir (VIREAD®); adefovir (PREVEON®, HEPSERA®); fomivirsen (VITRAVENE®); (c) non-nucleoside reverse transcriptase inhibitors, (NNRTIs), efavirenz (SUSTIVA®, STOCRIN®); nevirapine (VIRAMUNE®), delavirdine (RESCREPTOR®), etravirine (INTELENCE®), loviride; non-nucleoside inhibitor of HCV RNA-dependent RNA polymerase by ViroChem Pharma—VCH-759, non-nucleoside inhibitor of HCV polymerase inhibitor by Pfizer—PF-868554; and (d) polymerase inhibitors, including: RNA-dependent RNA polymerase of the hepatitis C virus by Boehringer Ingelheim—BILB-1941, RNA polymerase inhibitor by Roche—R1626; ACH-0137171 a replicase inhibitor by Achillion Pharmaceuticals, R7128—polymerase inhibitor by Roche/Pharmasset, ABT-333, and ABT-072—polymerase inhibitors by Abbott, BI 207127 polymerase inhibitor by Boehringer Ingelheim, PSI-7851—polymerase inhibitor by Pharmasset, ANA598—polymerase inhibitor by Anadys Pharmaceuticals, MK-3281—polymerase inhibitor by Merck, IDX184—polymerase inhibitor by Idenix, GSK 625433—polymerase inhibitor by Glaxo Smith Kline, INX-189—polymerase inhibitor by Inhibitex, NM283—polymerase inhibitor by Idenix, HCV796—polymerase inhibitor by Wyeth, GL60667 and GS9190—polymerase inhibitors by Gilead, PF-00868554 0 polymerase inhibitor by Pfizer, VCH759, VCH916, VX222 and VX759—polymerase inhibitors by Virochem, IDX184 and IDX375—polymerase inhibitors by Idenix, BMS650032—polymerase inhibitor by Bristol Myers Squibb; (2) protease inhibitors including for example: saquinavir (FOROVASE®/INVIRASE®), ritonavir (NORVIR®), indinavir (CRIXIVAN®), nelfinavir (VIRACEPT®), amprenavir (AGENERASE®), lopinavir (KALETRA®), atazanavir (REYATAZ®), fosamprenavir (LEXIVA®), tipranavir (APTIVUS®), darunavir (PREZISTA®), telapravir (VX-950); the second generation HCV protease inhibitors by Vertex Pharmaceuticals—VX-500 and VX-813; the NS3/4A protease inhibitor by Intermune/ Roche—ITMN-191/R-7227, boceprevir, the protease inhibitor by Schering-Plough—SCH 503034, the HCV NS3/4A protease inbihitor by Medivir/Tibotec—TMC435/TMC435350, ACH-1625 protease inhibitor by Achillion. Pharmaceuticals, ACH-806—protease inhibitor by Achillion/Gilead, BI201335 and BILN 2061—protease inhibitors by Boehringer Ingelheim, SCH 900518/SP900518 (narlaprevir)—protease inhibitor by Schering-Plough, MK-7009—protease inhibitor by Merck, BMS-650032, BMS-790052 and BMS-791325—protease inhibitors by Bristol Myeres Squibb, R7227—protease inhibitor by Roche, PHX1766—protease inhibitor by Phenomix, AVL-181—protease inhibitor by Avila Therapeutics, biliverdin, CTS-1027—protease inhibitor by Roche Biosciences, VX985—protease inhibitor by Vertex, VCH-759 and VCH-917—protease inhibitors by Virochem/Vertex, IDX-136 and 316—protease inhibitors by Idenix, ABT-450—protease inhibitor by Abbott, VBY 376—protease inhibitor by Virobay; (3) integrase inhibitors including for example: raltegravir (ISENTRESS®), elvitegravir; (4) combo therapies of nucleoside analog/nucleotide analog inhibitors, atripla (tenofovir+embricitabine+efavirenz), combivir (lamivudein+zidovudine), (5) entry or fusion inhibitors including for example: maraviroc, enfuvirtide, docosanol, anti-CD4 antibody, anti-gp120 antibody, anti-CCR5 antibody, HCV NS5a antagonists: (a) A-831, A-689 and AZD 2836 by Arrow Therapeutics, (b) BMS-790052 and BMS-824393 by Bristol Myers Squibb, (c) GSK-625433 by Glaxo Smith Kline, (d) NS4a antagonists ACH-1095; (5) maturation inhibitors including for example: bevirimat and vivecon; (6) viral release inhibitors including for example: zanamivir (RELENZA®), oseltamivir (TAMIFLU®), arbidol; (7) immune response enhancers, including for example interferon-α (E.g., BLX-883 and BLX 883 CR by Biolex Therapeutics, belerofon by Nautilus Biotech, long-acting IFN-α, IFN-α SR by LG Life Sciences, long acting IFN-α2b CR and IFN-α2b XL by Flamel Technologies, pegylated IFN-α (E.g., PEG-IFN-α-2a, PEGASYS®; PEG-IFN-α2b, PEGINTRON®), IFN-α2b-Human serum albumin fusion protein (ALBUFERON®); interferon-β, including IFN-β-1b (BETASERON®), interferon-γ, interferon-λ, pegylated interferon-λ (e.g., PEG-rIL-29 by ZymoGenetics/Novo Nordisk), interferon-w/leukocyte II interferon (E.g., Intarcia Therapeutics), toll-like receptor 7 agonists including imiquimod, isatoribine and prodrug variants thereof (e.g., ANA-975 and ANA-971) by Anadys Pharmaceuticals, oglufanide L-Glu-L-Trp-OH) and lipid- or -glycosylconjugated variants thereof by Implicit Bioscience, NOV-205 (E.g., Molixan®— a peptidic antiviral by Novelos Therapeutics, Inc.), the antiviral EHC18 by Enzo Biochem, gamma-D-glutamyl-L-tryptophan (E.g., SCV-07, SciClone Pharmaceuticals/Verta), aloferon (E.g., aloferon-1-HGVSGHGQHGVHG, aloferon-2-GVSGHGQHGVHG), CPG 10101—a TLR-9 agonist by Coley Pharmaceuticals/Actilon; (8) anti-viral synergistic enchancers, i.e., little or no anti-viral properties alone, but enhances the effect of other anti-virals—e.g., choroquine, grapefruit juice, hydroxyurea, leflunomide, mycophenolic acid, resveratrol, ritonavi; as well as other anti-viral drugs such as amantadine, edoxudine, famciclovir (FAMVIR®), penciclovir, fascarnet, fosfonet, ganciclovir (CYTOVENE®, CYMEVENE®, VITRASERT®), gardasil, ibacitabine, immunovir, moroxydine, nexavir, peramivir, pleconaril, podophyllotoxin, ribavirin, rimantadine, trifluridine, trizivir, tromantadine, truvada, valaciclovir, valganciclovir, vidarabine, and interferon enchancers such as EMZ702 by Transition Therapeutics, histamine dihydrochloride (E.g., Ceplene®+IFN-α); and (9)

miscellaneous or unclassified anti-virals such as: KPE-02003002 (Artenimol) by Kemin Pharmaceuticals, mitoquinone—a coenzyme Q10 anti-oxidant agonist by Antipodean Pharmaceuticals, alpha-glucosydase I inhibitors (E.g., MX-3253-celgosivir by Migenix Pharmaceuticals, castanospermine, glucocorticoid antagonists (e.g., HCV IRES inhibitors, mifepristone, VGX-410C by VGX Pharmaceuticals), hepatic agonists (E.g., PYN17 by Phynova Pharmaceuticals), anti-viral agents derived from traditional herbal therapies, e.g., PYN18 by Phynova Pharmaceuticals, caspase inhibitors (E.g., LB-84451—by LG Life Sciences, emricasan—PF-03491390/IDN-6556 by Pfizer), cyclosporine analogs that inhibit viral replication by preventing binding to cyclophilin A (E.g., SDZ NIM 911 by Novartis, Debio-025 by Debiopharm).

The term "anti fungal agent" includes any molecule that inhibits or abolishes the growth, morbity and/or survival of fungi. This includes for example, (1) polyene antifungals such as natamyin, rimocidin, filipin, nystatin, Amphotericin B, candicin; (2) imidazoles such as miconazole, ketoconazole (LOTRIMIN®), econazole, bifonazole, butoconazole, fenticonazole, isoconazole, oxiconazole, sertaconazole (ERTACZO®), sulconazole, tioconazole, (3) triazoles such as fluconazole, itraconazole, isavuconazole, ravuconazole posaconazole, voriconazole, terconazole; (4) allylamines such as terbinafine (LAMISIL®), amorolfine, naftifine (Naftin®), butenafine (LOTRIMIN ULTRA®); (5) Echinocandins, such as anidulafungin, caspofungin, micafungin, and other substances with anti-fungal properties such as benzoic acid, cicclopix, flucytosine, griseofulvin, gentian violet, haloprogin, tolnaftate (TINACTIN®, DESENEX®, AFTATE®), undecylenic acid, tea tree oil—ISO 4730 (Oil of Melaleuca, Terpinen-4-ol type) citronella oil, lemon grass, orange oil, palmarosa oil, patchouli, lemon myrtle, neem seed oil, Coconut Oil.

The term "anti-protozoan agent" or "anti-protozoal agent" includes any molecule that inhibits or abolishes the growth, morbidity and/or survival or protozoan organisms. Example anti-protozoan agents include, (1) anti-malarial agents, E.g., quinine, quinimax, quinidine, quinimax, chloroquine (ARALEN®), Hydroxycloroquine (PLAQUENIL®), amodiaquine, pyrimethamine (DARAPRIM®), sulphadoxine, proguanil, mefloquine (LARIAM®), halofantrine, primaquine, artemesinin and it derivatives (e.g., artemether, artensunate, dihydroartemisinin, arteether), clindamycin and combinations thereof; (2) protease inhibitors, and the drugs, benznidaole, buparvaquone, carbarsone, clioquinol, disulfuram, eflornithine, emetine, furazolidone, meglumine antimoniate, melarsoprol, metronidazole (FLAGYL®), miltefosine, nifurtimox, nitazoxanide, ornidazole, paromomycin sulfate, pentamidine, pyrimethamine (DARAPRIM®), secnidazole, tinidazole.

The term "vaccine" as used herein includes any nonpathogenic immunogen that, when inoculated into a host, induces protective immunity against a specific pathogen. Vaccines can take many forms. Vaccines can be whole organisms that share important antigens with the pathogen, but are not pathogenic themselves (e.g., cowpox). Vaccines can also be prepared from killed (e.g., Salk polio vaccine) or attenuated (lost ability to produce disease—e.g., Sabin polio vaccine). Vaccines can also be prepared from purified macromolecules isolated from the pathogenic organism. For example, toxoid vaccines (e.g., tetanus and diphtheria) containing the inactive form of soluble bacterial toxin—resulting in the production of anti-toxin antibodies, but not immunity to the intact bacteria. Subunit vaccines (e.g., Hepatitis B) contain only a single immunogenic protein isolated from the pathogen of interest. Hapten conjugate vaccines attach certain carbohydrate or polypeptide epitopes isolated from the pathogen of interest to immunogenic carriers, such as tetanus toxoid. These strategies essentially use the epitopes as haptens to induce antibody production, which then recognize the same epitope in the native pathogen. However, to be maximally effective, such vaccines must incorporate both B- and T-cell cell epitopes, and the T-cell epitopes must be chosen to ensure that they can be recognized, presented and responded to by the immune systems of the host individuals.

Examples of anti-viral vaccines that can be used in combination with the anti-PD-L1 antibodies for the methods described herein include: HCV vaccine (virasome) by Pevion Biotech., TG4040 (MVA-HCV by Transgene viron designed to enhance cellular (Cytotoxic T lymphocytes CD4+ and CD8+) immune response against NS3, NS4 and NS5B, CHRONVAC®—a codon-optimized NS3/4a DNA vaccine by Inovio Biomedical, HCV/CpG vaccines by Novartis, GI-5005—an HCV vaccine by Globeimmune, IC41 a mixture of synthetic peptides having HCV CD4 and CD8 T epitopes in combination with poly-L-arginine by Intercell.

Host responses to immunogens can be enhanced if administered as a mixture with adjuvants. Immune adjuvants function in one or more of the following ways: (1) prolonging retention of the immunogen, (2) increased effective size of the immunogen (and hence promoting phagocytosis and presentation to macrophages), (3) stimulating the influx of macrophage or other immune cells to the injection site, or (4) promoting local cytokine production and other immunologic activities. Example adjuvants include: complete Freund's adjuvant (CFA), aluminum salts, and mycobacterial derived proteins such as muramyl di- or tri-peptides.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain at its other end. The VL is aligned with the VH and the CL is aligned with the first constant domain of the heavy chain (CHI). Particular amino acid residues are believed to form an interface between the light chain and heavy chain variable domains. The pairing of a VH and VL together forms a single antigen-binding site. For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgA2.

An "isolated" antibody is one that has been identified, separated and/or recovered from a component of its production environment (E.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or nonproteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites. In some embodiments, the light chain variable region is the kappa type and may be referred to as "VK".

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226 or from Pro230, to the carboxyl-terminus thereof. A "native sequence Fc region" comprises an amino acid sequence identical to the amino acid sequence of a Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof. A "variant Fc region" comprises an amino acid sequence that differs from a native sequence Fc region by virtue of at least one "amino acid modification" as herein defined. The variant Fc region can have at least one amino acid substitution compared to a native sequence Fc region or to the Fc region of a parent antibody, and may have, for example, from about one to about ten amino acid substitutions, or from about one to about five amino acid substitutions in a native sequence Fc region or in the Fc region of the parent antibody. The variant Fc region can possess at least about 80% identity with a native sequence Fc region and/or with an Fc region of a parent antibody, and may have at least about 90% identity therewith, or have at least about 95% identity therewith.

An "antibody fragment" or "antigen-binding fragment" comprises a portion of an intact antibody, preferably the antigen binding and/or the variable region of the intact antibody. Examples of antibody fragments include Fab, Fab', F(ab')2 and Fv fragments; diabodies; linear antibodies (see U.S. Pat. No. 5,641,870, Example 2; Zapata et al., Protein Eng. 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having different antigen-binding activity and is still capable of cross-linking antigen. Fab' fragments differ from Fab fragments by having a few additional residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

"Functional fragments" of the antibodies of the present disclosure comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the VH and VL domains of the two antibodies are present on different polypeptide chains. Diabodies are described in greater detail in, for example, EP 404,097; WO 93/11161; Hollinger et al., Proc. Natl. Acad. Sci. USA 90: 6444-6448 (1993).

The antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include PRIMATTZFD® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982, 321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light to carboxy-terminus in the following order: FW1, HVR1, FW2, HVR2, FW3, HVR3, FW4. For comparison, the Kabat CDR definition by Yvonne Chen, et al. (Selection and Analysis of an Optimized Anti-VEGF Antibody: Crystal Structure of an Affinity-matured Fab in Complex with Antigen, J. Mol. Biol. (1999) 293, 865-881) is also shown below.

```
VH    EVQLVESGGGLVQPGGSLRLSCAASGFTFTSYGIHWVRQAPGKGLEWVSGISGAGDTTYYADSVKGRFTISRDNSKNTLYLQLN
ADG   <-----------FW1----------><---HVR_H1-><----FW2--><-------HVR_H2------><------------FW3

SLRAEDTAVYYCARERDYDFDYWGQGTLVTVSS
      -----------><-HVR_H3-><---FW4--->

VH    EVQLVESGGGLVQPGGSLRLSCAASGFTFTSYGIHWVRQAPGKGLEWVSGISGAGDTTYYADSVKGRFTISRDNSKNTLYLQLN
Kabat <-----------FW1----------><---CDR1----><------FW2----><------CDR2-----><--------------FW3

SLRAEDTAVYYCARERDYDFDYWGQGTLVTVSS
      --------------><-CDR3-><---FW4--->

VL    DIQLTQSPSSLSASVGDRVTITCRASQSVSSYLAWYQQKPGKAPKLLIYDASNLETGVPSRFSGSGSGTDFTLTISSLQPEDFA
ADG   <----------FW1-----------><--HVR_L1-><------FW2-----><-HVR_L2><-------------FW3----------

TYYCQQSYSTSHTFGQGTKVEIKR
      -><---HVR_L3-><---FW4--->

VL    DIQLTQSPSSLSASVGDRVTITCRASQSVSSYLAWYQQKPGKAPKLLIYDASNLETGVPSRFSGSGSGTDFTLTISSLQPEDFA
Kabat <----------FW1-----------><----CDR1--><------FW2-----><-CDR2><--------------FW3----------

TYYCQQSYSTSHTFGQGTKVEIKR
      ----><---CDR3-><---FW4--->
``` chain. See, e.g., Hamers-Casterman et al., Nature 363:446-448 (1993); Sheriff et al., Nature Struct. Biol. 3:733-736 (1996).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 (Kabat Numbering) | H31-H35B | H26-H35B | H26-H32 | H30-H35B |
| H1 (Chothia Numbering) | H31-H35 | H26-H35 | H26-H32 | H30-H35 |
| H2 | H50-H65 | H50-H58 | H53-H55 | H47-H58 |
| H3 | H95-H102 | H95-H102 | H96-H101 | H93-H101 |

In some embodiments, the three HVRs of the heavy chain are referred to herein as HVR_H1, HVR_H2, and HVR_H3 and the three HVRs of the light chain are referred to as HVR_L1, HVR_L2, and HVR_L3, the definition of which in accordance with the "ADG" numbering system as shown below. Each $V_H$ and $V_L$ is composed of three HVRs and four FWs (framework region), arranged from the amino-terminus to carboxy-terminus in the following order: FW1, HVR1, FW2, HVR2, FW3, HVR3, FW4.

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined. A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "amino-acid modification" at a specified position, e.g., of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., Bio/Technology 10:779-783 (1992) describes affinity maturation by VH- and VL-domain shuffling. Random mutagenesis of HVR and/or framework residues is described by, for example: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. The anti-PD-L1 antibodies of the disclosure block the signaling through PD-1 so as to restore a functional response by T-cells from a dysfunctional state to antigen stimulation.

An "agonist" or activating antibody is one that enhances or initiates signaling by the antigen to which it binds. In some embodiments, agonist antibodies cause or activate signaling without the presence of the natural ligand.

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody—dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The antibody effector function is readily determinable and measurable by one of ordinary skill in the art. In a preferred embodiment, the antibody effector functions of complement binding, complement dependent cytotoxicity and antibody dependent cytotoxicity are affected. In some embodiments of the disclosure, effector function is eliminated through a mutation in the constant region that eliminated glycosylation, e.g., "effector-less mutation." In one aspect, the effector-less mutation is an N297A or DANA mutation (D265A+N297A) in the CH2 region. Shields et al., J. Biol. Chem. 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., E. coli.) or in which result in an altered glycolsylation pattern that is ineffective or less effective at promoting effector function (e.g., Shinkawa et al., J. Biol. Chem. 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII Fc expression on hematopoietic cells is summarized in Table 3 on page 464 of Ravetch and Kinet, Annu. Rev. Immunol. 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., PNAS USA 95:652-656 (1998).

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass)

which are bound to their cognate antigen. To assess complement activation, a CDC assay, e.g., as described in Gazzano-Santoro et al., J. Immunol. Methods 202: 163 (1996), may be performed. Antibody variants with altered Fc region amino acid sequences and increased or decreased C1q binding capability are described in U.S. Pat. No. 6,194, 551B1 and WO99/51642. The contents of those patent publications are specifically incorporated herein by reference. See, also, Idusogie et al. J. Immunol. 164: 4178-4184 (2000).

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative and exemplary embodiments for measuring binding affinity are described in the following.

The "Kd" or "Kd value" according to this disclosure is in one embodiment measured by a radiolabeled antigen binding assay (MA) performed with the Fab version of the antibody and antigen molecule as described by the following assay that measures solution binding affinity of Fabs for antigen by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol. Biol 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [125I]-antigen are mixed with serial dilutions of a Fab of interest (consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

According to another embodiment, the Kd is measured by using surface-plasmon resonance assays using a BIACORE®-2000, a BIACORE®-3000 or a BIACORE®-T200instrument (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 µg/ml (~0.2 µM) before injection at a flow rate of 5 µL/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 µL/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds 106M-1 s-1 by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

An "on-rate," "rate of association," "association rate," or "$k_{on}$" according to this disclosure can also be determined as described above using a BIACORE®-2000 or a BIACORE®-3000 system (BIAcore, Inc., Piscataway, N.J.) at 25° C. with immobilized antigen CM5 chips at about 10 response units (RU). Briefly, carboxymethylated dextran biosensor ships (CM5, BIAcore Inc.) are activated with N-ethyl-N'-(3-dimethylamino propyl)-carbodiimide hydrochloride (ECD) and N-hydroxysuccinimide (NHS) according to the supplier's instructions. Antigen is diluted with 10 mM sodium acetate, pH 4.8, into 5 µg/ml 0.2 mM) before injection at a flow rate of 5 µl/min. to achieve approximately 10 response units (RU) of coupled protein. Following the injection of antigen, 1M ethanolamine is added to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgram. The equilibrium dissociation constant (Kd) was calculated as the ratio $k_{off}/k_{on}$. See, e.g., Chen, Y., et al., (1999) J. Mol. Biol 293:865-881. However, if the on-rate exceeds 106 M-1 S-1 by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the disclosure and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The terms "cross-compete", "cross-competition", "cross-block", "cross-blocked" and "cross-blocking" are used interchangeably herein to mean the ability of an antibody or fragment thereof to interfere with the binding directly or indirectly through allosteric modulation of the anti-PD-L1 antibodies of the disclosure to the target human PD-L1. The extent to which an antibody or fragment thereof is able to interfere with the binding of another to the target, and therefore whether it can be said to cross-block or cross-compete according to the disclosure, can be determined using competition binding assays. One particularly suitable quantitative cross-competition assay uses a FACS- or an AlphaScreen-based approach to measure competition between the labelled (e.g., His tagged, biotinylated or radioactive labelled) an antibody or fragment thereof and the other an antibody or fragment thereof in terms of their binding to the target. In general, a cross-competing antibody or fragment thereof is for example one which will bind to the target in the cross-competition assay such that, during the assay and in the presence of a second antibody or fragment thereof, the recorded displacement of the immunoglobulin single variable domain or polypeptide according to the disclosure is up to 100% (e.g., in FACS based competition assay) of the maximum theoretical displacement (e.g., displacement by cold (e.g., unlabeled) antibody or fragment thereof that needs to be cross-blocked) by the to be tested potentially cross-blocking antibody or fragment thereof that is present in a given amount. Preferably, cross-competing antibodies or fragments thereof have a recorded displacement that is between 10% and 100%, more preferred between 50% to 100%.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, authored by Genentech, Inc. The source code of ALIGN-2 has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described in the immediately preceding paragraph using the ALIGN-2 computer program.

An "isolated" nucleic acid molecule encoding the antibodies herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "host" is intended to include any individual virus or cell or culture thereof that can be or has been a recipient for vectors or for the incorporation of exogenous nucleic acid molecules, polynucleotides, and/or proteins. It also is intended to include progeny of a single virus or cell. The progeny may not necessarily be completely identical (in morphology or in genomic or total DNA complement) to the original parent cell due to natural, accidental, or deliberate mutation. The virus can be phage. The cells may be prokaryotic or eukaryotic, and include but are not limited to bacterial cells, yeast cells, insect cells, animal cells, and mammalian cells, e.g., murine, rat, simian, or human cells.

As used herein, the term "vector" refers to a nucleic acid molecule capable of transporting another nucleic acid to which it has been linked. A vector includes any genetic element, such as a plasmid, phage vector, phagemid, transposon, cosmid, chromosome, artificial chromosome, episome, virus, virion, etc., capable of replication (e.g., containing an origin of replication which is DNA sequence allowing initiation of replication by recruiting replication machinery proteins) when associated with the proper control elements and which can transfer gene sequences into or between hosts. One type of vector is an episome, i.e., a nucleic acid capable of extra-chromosomal replication. Another type of vector is an integrative vector that is designed to recombine with the genetic material of a host cell. Vectors may be both autonomously replicating and integrative, and the properties of a vector may differ depending on the cellular context (i.e., a vector may be autonomously replicating in one host cell type and purely integrative in another host cell type). Vectors generally contain one or a small number of restriction endonuclease recognition sites and/or sites for site-specific recombination. A foreign DNA fragment may be cleaved and ligated into the vector at these sites. The vector may contain a marker suitable for use in the identification of transformed or transfected cells. For example, markers may provide antibiotic resistant, fluorescent, enzymatic, as well as other traits. As a second example, markers may complement auxotrophic deficiencies or supply critical nutrients not in the culture media.

A "stable" formulation is one in which the protein therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation during storage can be used as an indicator of protein stability. Thus, a "stable" formulation may be one wherein less than about 10% and preferably less than about 5% of the protein are present as an aggregate in the formulation. In other embodiments, any increase in aggregate formation during storage of the formulation can be determined.

A "reconstituted" formulation is one which has been prepared by dissolving a lyophilized protein or antibody formulation in a diluent such that the protein is dispersed throughout. The reconstituted formulation is suitable for administration (e.g., subcutaneous administration) to a patient to be treated with the protein of interest and, in certain embodiments of the disclosure, may be one which is suitable for parenteral or intravenous administration.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present disclosure are hypertonic as a result of the addition of salt and/or buffer.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

A "pharmaceutically acceptable acid" includes inorganic and organic acids which are non toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cycloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo [2.2.2]-oct-2-ene-1-carboxylic, glucoheptonic, 4,4'-methylenebis-3-(hydroxy-2-ene-1-carboxylic acid), hydroxynapthoic.

"Pharmaceutically-acceptable bases" include inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amines, substituted amines, cyclic amines and basic ion exchange resins, [e.g., N(R')4+(where R' is independently H or C1-4 alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine. Additional pharmaceutically acceptable acids and bases useable with the present disclosure include those which are derived from the amino acids, for example, histidine, glycine, phenylalanine, aspartic acid, glutamic acid, lysine and asparagine.

"Pharmaceutically acceptable" buffers and salts include those derived from both acid and base addition salts of the above indicated acids and bases. Specific buffers and/or salts include histidine, succinate and acetate.

A "pharmaceutically acceptable sugar" is a molecule which, when combined with a protein of interest, significantly prevents or reduces chemical and/or physical instability of the protein upon storage. When the formulation is intended to be lyophilized and then reconstituted, "pharmaceutically acceptable sugars" may also be known as a "lyoprotectant". Exemplary sugars and their corresponding sugar alcohols include: an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol, and mannitol; propylene glycol; polyethylene glycol; PLURONICS®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose. Pharmaceutically acceptable sugars are added to the formulation in a "protecting amount" (e.g., pre-lyophilization) which means that the protein essentially retains its physical and chemical stability and integrity during storage (e.g., after reconstitution and storage).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g., phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

"Treatment" refers to clinical intervention designed to alter the natural course of the individual or cell being treated, and can be performed either for prophylaxis or during the course of clinical pathology. Desirable effects of treatment include preventing occurrence or recurrence of disease, preventing metastasis, decreasing the rate of disease progression, ameliorating or palliating the disease state, and remission or improved prognosis. In some embodiments, antibodies of the disclosure are used to delay development of a disease or disorder. A subject is successfully "treated", for example, using the apoptotic anti-PD-L1 antibodies of the disclosure if one or more symptoms associated with a T-cell dysfunctional disorder is mitigated.

An "effective amount" refers to at least an amount effective, at dosages and for periods of time necessary, to achieve the desired or indicated effect, including a therapeutic or prophylactic result. For example, an effective amount of the anti-PD-L1 antibodies of the present disclosure is at least the minimum concentration that results in inhibition of signaling from PD-L1, either through PD-1 on T-cells or B7.1 on other APCs or both.

A "therapeutically effective amount" is at least the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects of the antibody are outweighed by the therapeutically beneficial effects. For example, a therapeutically effective amount of the anti-PD-L1 antibodies of the present disclosure is at least the minimum concentration that results in inhibition of at least one symptom of a T cell dysfunctional disorder.

A "prophylactically effective amount" refers to an amount effective, at the dosages and for periods of time necessary, to achieve the desired prophylactic result. For example, a prophylactically effective amount of the anti-PD-L1 antibodies of the present disclosure is at least the minimum concentration that prevents or attenuates the development of at least one symptom of a T cell dysfunctional disorder.

"Chronic" administration refers to administration of the medicament(s) in a continuous as opposed to acute mode, so as to main the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, horses, rabbits, cattle, pigs, hamsters, gerbils, mice, ferrets, rats, cats, etc. Preferably, the mammal is human.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

A "sterile" formulation is aseptic or free from all living microorganisms and their spores.

An "autoimmune disorder" is a disease or disorder arising from and directed against an individual's own tissues or organs or a co-segregation or manifestation thereof or resulting condition therefrom. Autoimmune diseases can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis (RA), polymyositis, etc.). Preferred such diseases include autoimmune rheumatologic disorders (such as, for example, RA, Sjögren's syndrome, scleroderma, lupus such as SLE and lupus nephritis, polymyositis-dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, RA, ulcerative colitis, ANCA-associated vasculitis, lupus, multiple sclerosis, Sjögren's syndrome, Graves' disease, IDDM, pernicious anemia, thyroiditis, and glomerulonephritis.

The term "immunoconjugate" or "antibody-drug conjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the immunoconjugate. Additionally, the immunoconjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "cytotoxic agent" as used herein refers to a substance that inhibits or prevents the function of cells and/or causes destruction of cells. The term includes radioactive isotopes (e.g., At211, I131, I125, Y90, Re186, Re188, Sm153, Bi212, P32 and radioactive isotopes of Lu), and toxins such as small-molecule toxins or enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (see, e.g., Nicolaou et al., Angew. Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2', 2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin. A particularly preferred chemotherapeutic agent useful in combination with the anti-PD-L1 antibodies of the disclosure, especially in the treatment of tumor immunity is gemcitabine.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX®); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

A "growth-inhibitory agent" refers to a compound or composition that inhibits growth of a cell, which growth depends on receptor activation either in vitro or in vivo. Thus, the growth-inhibitory agent includes one that significantly reduces the percentage of receptor-dependent cells in S phase. Examples of growth-inhibitory agents include agents that block cell-cycle progression (at a place other than S phase), such as agents that induce G1 arrest and M-phase arrest. Classical M-phase blockers include the vincas and vinca alkaloids (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb).

The term "cytokine" is a generic term for proteins released by one cell population that act on another cell as intercellular mediators. Examples of such cytokines are lymphokines, monokines; interleukins (ILs) such as IL-1, IL-1α, IL-2, IL-3, IL-4, IL-5, IL-6, IL-7, IL-8, IL-9, IL-11, IL-12, IL-13, IL-15 . . . IL-35, including PROLEUKIN® rIL-2; a tumor-necrosis factor such as TNF-α or TNF-β; and other polypeptide factors including LIF and kit ligand (KL), while the term "interleukin" has now essentially become a synonym for cytokine. As used herein, the term cytokine includes proteins from natural sources or from recombinant cell culture and biologically active equivalents of the native-sequence cytokines, including synthetically produced small-molecule entities and pharmaceutically acceptable derivatives and salts thereof. Cytokines can be classified on the proximal location of the intended target, wherein autocrine refers to action on the same cell from which it is secreted, paracrine refers to action restricted to the immediate vicinity into which the cytokine is secreted, and endocrine refers to action in distant regions of the body. Immune cytokines can also be classified by whether they enhance a type I response, (e.g., IFN-γ, TGF-β etc), which favor cellular immunity or a type II response (IL-4, IL-10, IL-13, etc.), which favor antibody or humoral immunity. Immune cytokines play roles in co-stimulation, maturation, proliferation, activation, inflammation, growth, differentiation, cytokines production and secretion, survival of various immune cells.

Other terms used in the fields of immunology, cancer immunotherapy, pharmacology, recombinant nucleic acid technology, antibody engineering, and molecular and cell biology as used herein will be generally understood by one of ordinary skill in the applicable arts.

Antibody Library and Screening Thereof

Phage(mid) display (also referred to herein as phage display) can be used as a convenient and fast method for generating and screening many different potential variant antibodies in a library generated by, e.g., sequence design and/or randomization. However, other methods for making and screening altered antibodies are available to the skilled person.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage(mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., Proteins, 8:309 (1990); Lowman and Wells, Methods: A Companion to Methods in Enzymology, 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g., U.S. Pat. Nos. 5,723,286, 5,432,018, 5,580,717, 5,427,908 and 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

In one embodiment, heavy chain and light chain libraries are prepared and screened as described in PCT International Application Nos. PCT/CN2017/098333 and PCT/CN2017/098299, which are incorporated herein by reference in their entirety.

Methods of substituting an amino acid of choice into a template nucleic acid are well established in the art, some of which are described herein. For example, hypervariable region residues can be substituted using the Kunkel method. See, e.g., Kunkel et al., Methods Enzymol. 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

| IUB Codes | | |
|---|---|---|
| G (Guanine) | Y (C or T) | H (A or C or T) |
| A (Adenine) | M (A or C) | B (C or G or T) |
| T (Thymine) | K (G or T) | V (A or C or G) |
| C (Cytosine) | S (C or G) | D (A or G or T) |
| R (A or G) | W (A or T) | N (A or C or G or T) |

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Recombinant Preparation

The present disclosure also provides an isolated nucleic acid encoding an anti-PD-L1 antibody, vectors and host cells comprising such nucleic acid, and recombinant techniques for the production of the antibody.

For recombinant production of the antibody, the nucleic acid encoding it is isolated and inserted into a replicable vector for further cloning (amplification of the DNA) or for expression in accordance with general recombinant DNA technology. After library screening as described above, DNA encoding the antibody is readily deduced or otherwise isolated and sequenced using conventional procedures (e.g., by using oligonucleotide probes that are capable of binding specifically to genes encoding the heavy and light chains of the antibody). Many vectors known in the art are available for cloning the DNA. The choice of vector depends in part on the host cell to be used. Generally, preferred host cells are of either prokaryotic or eukaryotic (generally mammalian) origin. Once cloned, the antibody can be expressed and purified, using methods well known in the art.

Epitope Mapping and Related Technologies

The present disclosure includes anti-PD-L1 antibodies which interact with one or more amino acids found within one or more domains of the PD-L1 molecule including, e.g., extracellular (IgV-like) domain, the extracellular IgC-like domain, a transmembrane domain, and an intracellular domain. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the PD-L1 molecule (e.g., a linear epitope in a domain). Alternatively, the epitope may consist of a plurality of noncontiguous amino acids (or amino acid sequences) located within either or both of the aforementioned domains of the PD-L1 molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, NY). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation. Modification-Assisted Profiling (MAP), also known as Antigen Structure-based Antibody Profiling (ASAP) is a method that categorizes large numbers of antibodies directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

One can easily determine whether an antibody binds to the same epitope as, or competes for binding with, a reference anti-PD-L1 antibody by using routine methods known in the art. For example, to determine if a test antibody binds to the same epitope as a reference anti-PD-L1 antibody of the disclosure, the reference antibody is allowed to bind to a PD-L1 protein or peptide under saturating conditions. Next, the ability of a test antibody to bind to the PD-L1 molecule is assessed. If the test antibody is able to bind to PD-L1 following saturation binding with the reference anti-PD-L1 antibody, it can be concluded that the test antibody binds to a different epitope than the reference anti-PD-L1 antibody. On the other hand, if the test antibody is not able to bind to the PD-L1 protein following saturation binding with the reference anti-PD-L1 antibody, then the test antibody may bind to the same epitope as the epitope bound by the reference anti-PD-L1 antibody of the disclosure.

To determine if an antibody competes for binding with a reference anti-PD-L1 antibody, the above-described binding methodology is performed in two orientations: In a first orientation, the reference antibody is allowed to bind to a PD-L1 protein under saturating conditions followed by assessment of binding of the test antibody to the PD-L1 molecule. In a second orientation, the test antibody is allowed to bind to a PD-L1 molecule under saturating conditions followed by assessment of binding of the reference antibody to the PD-L1 molecule. If, in both orientations, only the first (saturating) antibody is capable of binding to the PD-L1 molecule, then it is concluded that the test antibody and the reference antibody compete for binding to PD-L1. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Antibody and Fragments

In some embodiments, provided herein is an isolated antibody, or antigen-binding fragment thereof, comprising one or more of the following HVR_L1, HVR_L2, and/or HRV_L3:

(1) an HVR_L1 having the amino acid sequence selected from the group consisting of (a) RASQX1X2X3X4X5LA (SEQ ID NO: 1)
wherein:
X1: G S

X2: I V

X3: E G S

X4: K P S

X5: F W Y (b) RASX1SVDFX2GX3SFLX4 (SEQ ID NO: 2)
wherein:
X1: E Q

X2: F H Y

X3: I K

X4: A D (c) X1ASQX2IPX3FLX4 (SEQ ID NO: 3)
wherein:
X1: Q R

X2: D S T

X3: K S T

X4: A N (d) RASQGX1SX2X3LA (SEQ ID NO: 4)
wherein:
X1: I V

X2: P S

X3: W Y
and (e) RASQX1IPSFLN (SEQ ID NO: 5)
wherein:
X1: S T (2) an HVR_L2 having the amino acid sequence selected from the group consisting of (a) DASX1X2X3X4GX5 (SEQ ID NO: 6)
wherein:
X1: N S

X2: L R

X3: A E

X4: S T

X5: I V (b) AASX1LQSGV (SEQ ID NO: 7)
wherein:
X1: S T
and (c) DASNX1X2TGX3 (SEQ ID NO: 8)
wherein:
X1: L R

X2: A E

X3: I V (3) HVR_L3 having the amino acid sequence selected from the group consisting of:

(e) YCQQYDX1WPYT (SEQ ID NO: 9)
wherein:
X1: A H S Y (f) YCQX1YX2SWPRX3FT (SEQ ID NO: 10)
wherein:
X1: H Q

X2: G I S T V

X3: G L Q R V (g) YCQQYDX1WPYT (SEQ ID NO: 11)
wherein:
X1: A S
and (h) YCQHYX1SWPRQFT (SEQ ID NO: 12)
wherein:
X1: I T In certain embodiments, the antibody or fragment thereof can include an HVR_L1 having the amino acid sequence selected from the group consisting of SEQ ID NOs: 13-39 and 94-102, an HVR_L2 having the amino acid sequence selected from the group consisting of SEQ ID NOs: 40-66 and 103-111, and/or an HVR_L3 having the amino acid sequence selected from the group consisting of SEQ ID NOs: 67-93 and 112-120. In some embodiments, the antibody or fragment thereof having the HVR_L1 having the amino acid sequence selected from the group consisting of SEQ ID NOs: 13-39, the HVR_L2 having the amino acid sequence selected from the group consisting of SEQ ID NOs: 40-66, and/or the HVR_L3 having the amino acid sequence selected from the group consisting of SEQ ID NOs: 67-93 is cross-reactive with human and monkey PD-L1. In certain embodiments, the antibody or fragment thereof having the HVR_L1 having the amino acid sequence selected from the group consisting of SEQ ID NOs: 94-102, the HVR_L2 having the amino acid sequence selected from the group consisting of SEQ ID NOs: 103-111, and/or the HVR_L3 having the amino acid sequence selected from the group consisting of SEQ ID NOs: 112-120 is cross-reactive with human, monkey and mouse PD-L1.

>B14033-HVR_L1 (SEQ ID NO: 13)
RASQGIGSFLA

>B14614-HVR_L1 (SEQ ID NO: 14)
RASESVDFYGKSFLD

>B14615-HVR_L1 (SEQ ID NO: 15)
RASQSVDFYGKSFLA

>B14617-HVR_L1 (SEQ ID NO: 16)
RASESVDFFGKSFLA

>B14622-HVR_L1 (SEQ ID NO: 17)
RASQSVDFYGKSFLD

>B14627-HVR_L1 (SEQ ID NO: 18)
RASQSVSSWLA

>B14631-HVR_L1 (SEQ ID NO: 19)
RASESVDFFGKSFLA

>B14633-HVR_L1 (SEQ ID NO: 20)
RASESVDFHGISFLA

>B14634-HVR_L1 (SEQ ID NO: 21)
RASQSVSPYLA

>B14638-HVR_L1 (SEQ ID NO: 22)
RASQSVGSIYLG

>B14642-HVR_L1 (SEQ ID NO: 23)
RASQSVDFYGKSFLA

>B14644-HVR_L1 (SEQ ID NO: 24)
RASESVDFYGKSFLA

>B14645-HVR_L1 (SEQ ID NO: 25)
RASQSVDFYGKSFLD

>B14650-HVR_L1 (SEQ ID NO: 26)
RASESVDFYGKSFLD

>B14651-HVR_L1 (SEQ ID NO: 27)
RASESVDFHGKSFLA

>B14652-HVR_L1 (SEQ ID NO: 28)
RASQGVSPWLA

>B14654-HVR_L1 (SEQ ID NO: 29)
RASQSVSPYLA

>B14658-HVR_L1 (SEQ ID NO: 30)
RASQSVDFHGKSFLD

>B14665-HVR_L1 (SEQ ID NO: 31)
RASQSVDFYGKSFLA

>B14673-HVR_L1 (SEQ ID NO: 32)
RASESVDFYGKSFLA

>B14674-HVR_L1 (SEQ ID NO: 33)
RASQSIEKWLA

>B14681-HVR_L1 (SEQ ID NO: 34)
RASQSVDFHGISFLD

>B14689-HVR_L1 (SEQ ID NO: 35)
RASQSVDFYGKSFLD

>B14690-HVR_L1 (SEQ ID NO: 36)
RASQSVDFHGISFLD

>B13002-HVR_L1 (SEQ ID NO: 37)
RASQGVSSYLA

>B13004-HVR_L1 (SEQ ID NO: 38)
RASQGISPWLA

>B13005-HVR_L1 (SEQ ID NO: 39)
RASQSVSSYLA

>B14033-HVR_L2 (SEQ ID NO: 40)
DASSLESGV

>B14614-HVR_L2 (SEQ ID NO: 41)
DASNRATGI

>B14615-HVR_L2 (SEQ ID NO: 42)
DASSLESGV

>B14617-HVR_L2 (SEQ ID NO: 43)
DASSLESGV

>B14622-HVR_L2 (SEQ ID NO: 44)
DASNRATGI

>B14627-HVR_L2 (SEQ ID NO: 45)
DASSLESGV

>B14631-HVR_L2 (SEQ ID NO: 46)
DASNLETGV

>B14633-HVR_L2 (SEQ ID NO: 47)
DASNRATGI

>B14634-HVR_L2 (SEQ ID NO: 48)
DASNLETGV

>B14638-HVR_L2 (SEQ ID NO: 49)
DASNRATGI

>B14642-HVR_L2 (SEQ ID NO: 50)
DASSLESGV

>B14644-HVR_L2 (SEQ ID NO: 51)
DASNRATGI

>B14645-HVR_L2 (SEQ ID NO: 52)
DASNLETGV

>B14650-HVR_L2 (SEQ ID NO: 53)
DASNRATGI

>B14651-HVR_L2 (SEQ ID NO: 54)
DASNRATGI

>B14652-HVR_L2 (SEQ ID NO: 55)
DASSLESGV

-continued

>B14654-HVR_L2 (SEQ ID NO: 56)
DASNRATGI

>B14658-HVR_L2 (SEQ ID NO: 57)
DASNRATGI

>B14665-HVR_L2 (SEQ ID NO: 58)
DASSLESGV

>B14673-HVR_L2 (SEQ ID NO: 59)
DASSLESGV

>B14674-HVR_L2 (SEQ ID NO: 60)
DASSLESGV

>B14681-HVR_L2 (SEQ ID NO: 61)
DASNRATGI

>B14689-HVR_L2 (SEQ ID NO: 62)
DASSLESGV

>B14690-HVR_L2 (SEQ ID NO: 63)
DASNLETGV

>B13002-HVR_L2 (SEQ ID NO: 64)
DASNLETGV

>B13004-HVR_L2 (SEQ ID NO: 65)
DASNRATGI

>B13005-HVR_L2 (SEQ ID NO: 66)
DASNLETGV

>B14033-HVR_L3 (SEQ ID NO: 67)
YCQQYDYWPYT

>B14614-HVR_L3 (SEQ ID NO: 68)
YCQQYDSWPYT

>B14615-HVR_L3 (SEQ ID NO: 69)
YCQQYDHWPYT

>B14617-HVR_L3 (SEQ ID NO: 70)
YCQQYDSWPYT

>B14622-HVR_L3 (SEQ ID NO: 71)
YCQQYDSWPYT

>B14627-HVR_L3 (SEQ ID NO: 72)
YCQQYDSWPYT

>B14631-HVR_L3 (SEQ ID NO: 73)
YCQQYDHWPYT

>B14633-HVR_L3 (SEQ ID NO: 74)
YCQQYDHWPYT

>B14634-HVR_L3 (SEQ ID NO: 75)
YCQQYDAWPYT

-continued

>B14638-HVR_L3 (SEQ ID NO: 76)
YCQQYDSWPYT

>B14642-HVR_L3 (SEQ ID NO: 77)
YCQQYDAWPYT

>B14644-HVR_L3 (SEQ ID NO: 78)
YCQQYDYWPYT

>B14645-HVR_L3 (SEQ ID NO: 79)
YCQQYDAWPYT

>B14650-HVR_L3 (SEQ ID NO: 80)
YCQQYDHWPYT

>B14651-HVR_L3 (SEQ ID NO: 81)
YCQQYDHWPYT

>B14652-HVR_L3 (SEQ ID NO: 82)
YCQQYDAWPYT

>B14654-HVR_L3 (SEQ ID NO: 83)
YCQQYDAWPYT

>B14658-HVR_L3 (SEQ ID NO: 84)
YCQQYDSWPYT

>B14665-HVR_L3 (SEQ ID NO: 85)
YCQQYDSWPYT

>B14673-HVR_L3 (SEQ ID NO: 86)
YCQQYDSWPYT

>B14674-HVR_L3 (SEQ ID NO: 87)
YCQQYDAWPYT

>B14681-HVR_L3 (SEQ ID NO: 88)
YCQQYDHWPYT

>B14689-HVR_L3 (SEQ ID NO: 89)
YCQQYDHWPYT

>B14690-HVR_L3 (SEQ ID NO: 90)
YCQQYDSWPYT

>B13002-HVR_L3 (SEQ ID NO: 91)
YCQQYDAWPYT

>B13004-HVR_L3 (SEQ ID NO: 92)
YCQQYDSWPYT

>B13005-HVR_L3 (SEQ ID NO: 93)
YCQQYDAWPYT

>B14032-HVR_L1 (SEQ ID NO: 94)
QASQDIPTFLA

>B15012-HVR_L1 (SEQ ID NO: 95)
RASQTIPSFLN

>B15014-HVR_L1 (SEQ ID NO: 96)
RASQDIPKFLA

>B15016-HVR_L1 (SEQ ID NO: 97)
RASQTIPSFLN

>B15022-HVR_L1 (SEQ ID NO: 98)
RASQSIPSFLN

>B15024-HVR_L1 (SEQ ID NO: 99)
RASQSIPTFLN

>B15041-HVR_L1 (SEQ ID NO: 100)
RASQSIPSFLN

>B15074-HVR_L1 (SEQ ID NO: 101)
RASQTIPSFLN

>B15082-HVR_L1 (SEQ ID NO: 102)
RASQTIPSFLN

>B14032-HVR_L2 (SEQ ID NO: 103)
AASSLQSGV

>B15012-HVR_L2 (SEQ ID NO: 104)
AASTLQSGV

>B15014-HVR_L2 (SEQ ID NO: 105)
AASTLQSGV

>B15016-HVR_L2 (SEQ ID NO: 106)
AASSLQSGV

>B15022-HVR_L2 (SEQ ID NO: 107)
AASTLQSGV

>B15024-HVR_L2 (SEQ ID NO: 108)
AASTLQSGV

>B15041-HVR_L2 (SEQ ID NO: 109)
AASSLQSGV

>B15074-HVR_L2 (SEQ ID NO: 110)
AASTLQSGV

>B15082-HVR_L2 (SEQ ID NO: 111)
AASSLQSGV

>B14032-HVR_L3 (SEQ ID NO: 112)
YCQQYVSWPRGFT

>B15012-HVR_L3 (SEQ ID NO: 113)
YCQHYSSWPRGFT

>B15014-HVR_L3 (SEQ ID NO: 114)
YCQHYVSWPRQFT

>B15016-HVR_L3 (SEQ ID NO: 115)
YCQHYTSWPRQFT

>B15022-HVR_L3 (SEQ ID NO: 116)
YCQQYSSWPRLFT

>B15024-HVR_L3 (SEQ ID NO: 117)
YCQHYVSWPRLFT

>B15041-HVR_L3 (SEQ ID NO: 118)
YCQHYISWPRQFT

>B15074-HVR_L3 (SEQ ID NO: 119)
YCQHYISWPRVFT

>B15082-HVR_L3 (SEQ ID NO: 120)
YCQHYGSWPRRFT

In some embodiments, the antibody or fragment thereof can include a VL having the amino acid sequence selected from the group consisting of SEQ ID NOs:121-125:

(SEQ ID NO: 121)
DIQLTQSPSSLSASVGDRVTITCRASQX1X2X3X4X5LAWYQQKPGKAPK
LLIYDASX6X7X8X9GX10PSRFSGSGSGTDFTLTISSLQPEDFATYYCQ
QYDX11WPYTFGQGTKVEIKR,
wherein:
X1: G S
X2: I V
X3: E G S
X4: K P S
X5: F W Y
X6: N S
X7: L R
X8: A E
X9: S T
X10: I V
X11: A S Y (SEQ ID NO: 122)
DIQLTQSPSSLSASVGDRVTITCRASX1SVDFX2GX3SFLX4WYQQKPG
KAPKLLIYDASX5X6X7X8GX9PSRFSGSGSGTDFTLTISSLQPEDFAT
YYCQQYDX10WPYTFGQGTKVEIKR
wherein:
X1: E Q
X2: F H Y
X3: I K
X4: A D
X5: N S
X6: L R
X7: A E
X8: S T
X9: I V
X10: A H S Y (SEQ ID NO: 123)
DIQLTQSPSSLSASVGDRVTITCX1ASQX2IPX3FLX4WYQQKPGKAPKL

LIYAASX5LQSGVPSRFSGSGSGTDFTLTISSLQPEDFATYYCQX6YX7S

WPRX8FTFGQGTKVEIKR
wherein:
X1: Q R

X2: D S T

X3: K S T

X4: A N

X5: S T

X6: H Q

X7: G I S T V

X8: G L Q R V (SEQ ID NO: 124)
DIQLTQSPSSLSASVGDRVTITCRASQGX1SX2X3LAWYQQKPGKAPKLL

IYDASNX4X5TGX6PSRFSGSGSGTDFTLTISSLQPEDFATYYCQQYDX7

WPYTFGQGTKVEIKR
wherein:
X1: I V

X2: P S

X3: W Y

X4: L R

X5: A E

X6: I V

X7: A S (SEQ ID NO: 125)
DIQLTQSPSSLSASVGDRVTITCRASQX1IPSFLNWYQQKPGKAPKLLIY

AASSLQSGVPSRFSGSGSGTDFTLTISSLQPEDFATYYCQHYX2SWPRQF

TFGQGTKVEIKR
wherein:
X1: S T

X2: I T

In some embodiments, the antibody or fragment thereof having the VL having the amino acid sequence selected from the group consisting of SEQ ID NOs: 121-122, and 124 is cross-reactive with human and monkey PD-L1. In certain embodiments, the antibody or fragment thereof having the VL having the amino acid sequence selected from the group consisting of SEQ ID NOs: 123 and 125 is cross-reactive with human, monkey and mouse PD-L1.

In various embodiments, the antibody or fragment thereof can further include an HVR_H1 having the amino acid sequence selected from the group consisting of SEQ ID NOs: 164 and 167, an HVR_H2 having the amino acid sequence selected from the group consisting of SEQ ID NOs: 165 and 168, and/or an HVR_H3 having the amino acid sequence selected from the group consisting of SEQ ID NOs: 166 and 169:

(SEQ ID NO: 164)
YTFSNYGIFIWV (SEQ ID NO: 165)
IGWIYPSGGGTKYAQKFQGRV (SEQ ID NO: 166)
AREGGGYGYALDY (SEQ ID NO: 167)
YSISSGYYWGWI (SEQ ID NO: 168)
IGIIYPSGGGTNYAQKFQGRV (SEQ ID NO: 169)
ARGGGLGFDY

In some embodiments, the antibody or fragment thereof further comprises a VH having the amino acid sequence selected from the group consisting of SEQ ID NOs: 126-127. In embodiments, the antibody or fragment thereof of can comprise a VL having the amino acid sequence selected from the group consisting of SEQ ID NOs: 128-163. These sequences can be in the form of Fab.

>B14032-VH
(SEQ ID NO: 127)
EVQLVESGGGLVQPGGSLRLSCAASGYSISSGYYWGWIRQAPGKGLEWIG

IIYPSGGGTNYAQKFQGRVTISRDNSKNTLYLQLNSLRAEDTAVYYCARG

GGLGFDYWGQGTLVTVSS

>B14032-VL
(SEQ ID NO: 128)
DIQLTQSPSSLSASVGDRVTITCQASQDIPTFLAWYQQKPGKAPKLLIYA

ASSLQSGVPSRFSGSGSGTDFTLTISSLQPEDFATYYCQQYVSWPRGFTF

GQGTKVEIKR

>B14033-VH
(SEQ ID NO: 126)
EVQLVESGGGLVQPGGSLRLSCAASGYTFSNYGIHWVRQAPGKGLEWIGW

IYPSGGGTKYAQKFQGRVTISRDNSKNTLYLQLNSLRAEDTAVYYCAREG

GGYGYALDWGQGTLVTVSS

>B14033-VL
(SEQ ID NO: 129)
DIQLTQSPSSLSASVGDRVTITCRASQGIGSFLAWYQQKPGKAPKLLIYD

ASSLESGVPSRFSGSGSGTDFTLTISSLQPEDFATYYCQQYDWPYTFGQG

TKVEIKR

>B14614-VH
(SEQ ID NO: 126)
EVQLVESGGGLVQPGGSLRLSCAASGYTFSNYGIHWVRQAPGKGLEWIGW

IYPSGGGTKYAQKFQGRVTISRDNSKNTLYLQLNSLRAEDTAVYYCAREG

GGYGYALDWGQGTLVTVSS

>B14614-VL
(SEQ ID NO: 130)
DIQLTQSPSSLSASVGDRVTITCRASESVDFYGKSFLDWYQQKPGKAPKL

LIYDASNRATGIPSRFSGSGSGTDFTLTISSLQPEDFATYYCQQYDSWPY

TFGQGTKVEIKR

>B14615-VH
(SEQ ID NO: 126)
EVQLVESGGGLVQPGGSLRLSCAASGYTFSNYGIHWVRQAPGKGLEWIGW
IYPSGGGTKYAQKFQGRVTISRDNSKNTLYLQLNSLRAEDTAVYYCAREG
GGYGYALDWGQGTLVTVSS

>B14615-VL
(SEQ ID NO: 131)
DIQLTQSPSSLSASVGDRVTITCRASQSVDFYGKSFLAWYQQKPGKAPKL
LIYDASSLESGVPSRFSGSGSGTDFTLTISSLQPEDFATYYCQQYDHWPY
TFGQGTKVEIKR

>B14617-VH
(SEQ ID NO: 126)
EVQLVESGGGLVQPGGSLRLSCAASGYTFSNYGIHWVRQAPGKGLEWIGW
IYPSGGGTKYAQKFQGRVTISRDNSKNTLYLQLNSLRAEDTAVYYCAREG
GGYGYALDWGQGTLVTVSS

>B14617-VL
(SEQ ID NO: 132)
DIQLTQSPSSLSASVGDRVTITCRASESVDFFGKSFLAWYQQKPGKAPKL
LIYDASSLESGVPSRFSGSGSGTDFTLTISSLQPEDFATYYCQQYDSWPY
TFGQGTKVEIKR

>B14622-VH
(SEQ ID NO: 126)
EVQLVESGGGLVQPGGSLRLSCAASGYTFSNYGIHWVRQAPGKGLEWIGW
IYPSGGGTKYAQKFQGRVTISRDNSKNTLYLQLNSLRAEDTAVYYCAREG
GGYGYALDWGQGTLVTVSS

>B14622-VL
(SEQ ID NO: 133)
DIQLTQSPSSLSASVGDRVTITCRASQSVDFYGKSFLDWYQQKPGKAPKL
LIYDASNRATGIPSRFSGSGSGTDFTLTISSLQPEDFATYYCQQYDSWPY
TFGQGTKVEIKR

>B14627-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14627-VL
(SEQ ID NO: 134)
DIQLTQSPSSLSASVGDRVTITCRASQSVSSWLAWYQQKPGKAPKLLIYD
ASSLESGVPSRFSGSGSGTDFTLTISSLQPEDFATYYCQQYDSWPYTFGQ
GTKVEIKR

>B14631-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14631-VL
(SEQ ID NO: 135)
DIQLTQSPSSLSASVGDRVTITCRASESVDFFGKSFLAWYQQKPGKAPKL
LIYDASNLETGVPSRFSGSGSGTDFTLTISSLQPEDFATYYCQQYDHWPY
TFGQGTKVEIKR

>B14633-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14633-VL
(SEQ ID NO: 136)
DIQLTQSPSSLSASVGDRVTITCRASESVDFHGISFLAWYQQKPGKAPKL
LIYDASNRATGIPSRFSGSGSGTDFTLTISSLQPEDFATYYCQQYDHWPY
TFGQGTKVEIKR

>B14634-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14634-VL
(SEQ ID NO: 137)
DIQLTQSPSSLSASVGDRVTITCRASQSVSPYLAWYQQKPGKAPKLLIYD
ASNLETGVPSRFSGSGSGTDFTLTISSLQPEDFATYYCQQYDAWPYTFGQ
GTKVEIKR

>B14638-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDYWGQGTLVTVSS

>B14638-VL
(SEQ ID NO: 138)
DIQLTQSPSSLSASVGDRVTITCRASQSVGSIYLGWYQQKPGKAPKLLIY
DASNRATGIPSRFSGSGSGTDFTLTISSLQPEDFATYYCQQYDSWPYTFG
QGTKVEIKR

>B14642-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDYWGQGTLVTVSS

>B14642-VL
(SEQ ID NO: 139)
DIQLTQSPSSLSASVGDRVTITCRASQSVDFYGKSFLAWYQQKPGKAPKL
LIYDASSLESGVPSRFSGSGSGTDFTLTISSLQPEDFATYYCQQYDAWPY
TFGQGTKVEIKR

>B14644-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14644-VL
(SEQ ID NO: 140)
DIQLTQSPSSLSASVGDRVTITCRASESVDFYGKSFLAWYQQKPGKAPKL
LIYDASNRATGIPSRFSGSGSGTDFTLTISSLQPEDFATYYCQQYDYWPY
TFGQGTKVEIKR

>B14645-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14645-VL
(SEQ ID NO: 141)
DIQLTQSPSSLSASVGDRVTITCRASQSVDFYGKSFLDWYQQKPGKAPKL
LIYDASNLETGVPSRFSGSGSGTDFTLTISSLQPEDFATYYCQQYDAWPY
TFGQGTKVEIKR

>B14650-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14650-VL
(SEQ ID NO: 142)
DIQLTQSPSSLSASVGDRVTITCRASESVDFYGKSFLDWYQQKPGKAPKL
LIYDASNRATGIPSRFSGSGSGTDFTLTISSLQPEDFATYYCQQYDHWPY
TFGQGTKVEIKR

>B14651-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14651-VL
(SEQ ID NO: 143)
DIQLTQSPSSLSASVGDRVTITCRASESVDFHGKSFLAWYQQKPGKAPKL
LIYDASNRATGIPSRFSGSGSGTDFTLTISSLQPEDFATYYCQQYDHWPY
TFGQGTKVEIKR

>B14652-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14652-VL
(SEQ ID NO: 144)
DIQLTQSPSSLSASVGDRVTITCRASQGVSPWLAWYQQKPGKAPKLLIYD
ASSLESGVPSRFSGSGSGTDFTLTISSLQPEDFATYYCQQYDAWPYTFGQ
GTKVEIKR

>B14654-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14654-VL
(SEQ ID NO: 145)
DIQLTQSPSSLSASVGDRVTITCRASQSVSPYLAWYQQKPGKAPKLLIYD
ASNRATGIPSRFSGSGSGTDFTLTISSLQPEDFATYYCQQYDAWPYTFGQ
GTKVEIKR

>B14658-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14658-VL
(SEQ ID NO: 146)
DIQLTQSPSSLSASVGDRVTITCRASQSVDFHGKSFLDWYQQKPGKAPKL
LIYDASNRATGIPSRFSGSGSGTDFTLTISSLQPEDFATYYCQQYDSWPY
TFGQGTKVEIKR

>B14665-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14665-VL
(SEQ ID NO: 147)
DIQLTQSPSSLSASVGDRVTITCRASQSVDFYGKSFLAWYQQKPGKAPKL
LIYDASSLESGVPSRFSGSGSGTDFTLTISSLQPEDFATYYCQQYDSWPY
TFGQGTKVEIKR

>B14673-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14673-VL
(SEQ ID NO: 148)
DIQLTQSPSSLSASVGDRVTITCRASESVDFYGKSFLAWYQQKPGKAPKL
LIYDASSLESGVPSRFSGSGSGTDFTLTISSLQPEDFATYYCQQYDSWPY
TFGQGTKVEIKR

>B14674-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14674-VL
(SEQ ID NO: 149)
DIQLTQSPSSLSASVGDRVTITCRASQSIEKWLAWYQQKPGKAPKLLIYD
ASSLESGVPSRFSGSGSGTDFTLTISSLQPEDFATYYCQQYDAWPYTFGQ
GTKVEIKR

>B14681-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14681-VL
(SEQ ID NO: 150)
DIQLTQSPSSLSASVGDRVTITCRASQSVDFHGISFLDWYQQKPGKAPKL
LIYDASNRATGIPSRFSGSGSGTDFTLTISSLQPEDFATYYCQQYDHWPY
TFGQGTKVEIKR

>B14689-VH
(SEQ ID NO: 126)
EVQLVESGGGLVQPGGSLRLSCAASGYTFSNYGIFIWVRQAPGKGLEWIG
WIYPSGGGTKYAQKFQGRVTISRDNSKNTLYLQLNSLRAEDTAVYYCARE
GGGYGYALDWGQGTLVTVSS

>B14689-VL
(SEQ ID NO: 151)
DIQLTQSPSSLSASVGDRVTITCRASQSVDFYGKSFLDWYQQKPGKAPKL
LIYDASSLESGVPSRFSGSGSGTDFTLTISSLQPEDFATYYCQQYDHWPY
TFGQGTKVEIKR

>B14690-VH
(SEQ ID NO: 126)
EVQLVESGGGLVQPGGSLRLSCAASGYTFSNYGIHWVRQAPGKGLEWIGW
IYPSGGGTKYAQKFQGRVTISRDNSKNTLYLQLNSLRAEDTAVYYCAREG
GGYGYALDWGQGTLVTVSS

>B14690-VL
(SEQ ID NO: 152)
DIQLTQSPSSLSASVGDRVTITCRASQSVDFHGISFLDWYQQKPGKAPKL
LIYDASNLETGVPSRFSGSGSGTDFTLTISSLQPEDFATYYCQQYDSWPY
TFGQGTKVEIKR

>B15012-VH
(SEQ ID NO: 127)
EVQLVESGGGLVQPGGSLRLSCAASGYSISSGYYWGWIRQAPGKGLEWIG
ITYPSGGGTNYAQKFQGRVTISRDNSKNTLYLQLNSLRAEDTAVYYCARG
GGLGFDWGQGTLVTVSS

>B15012-VL
(SEQ ID NO: 153)
DIQLTQSPSSLSASVGDRVTITCRASQTIPSFLNWYQQKPGKAPKLLIYA
ASTLQSGVPSRFSGSGSGTDFTLTISSLQPEDFATYYCQHYSSWPRGFTF
GQGTKVEIKR

>B15014-VH
(SEQ ID NO: 127)
EVQLVESGGGLVQPGGSLRLSCAASGYSISSGYYWGWIRQAPGKGLEWIG
ITYPSGGGTNYAQKFQGRVTISRDNSKNTLYLQLNSLRAEDTAVYYCARG
GGLGFDWGQGTLVTVSS

>B15014-VL
(SEQ ID NO: 154)
DIQLTQSPSSLSASVGDRVTITCRASQDIPKFLAWYQQKPGKAPKLLIYA
ASTLQSGVPSRFSGSGSGTDFTLTISSLQPEDFATYYCQHYVSWPRQFTF
GQGTKVEIKR

>B15016-VH
(SEQ ID NO: 127)
EVQLVESGGGLVQPGGSLRLSCAASGYSISSGYYWGWIRQAPGKGLEWIG
ITYPSGGGTNYAQKFQGRVTISRDNSKNTLYLQLNSLRAEDTAVYYCARG
GGLGFDYWGQGTLVTVSS

>B15016-VL
(SEQ ID NO: 155)
DIQLTQSPSSLSASVGDRVTITCRASQTIPSFLNWYQQKPGKAPKLLIYA
ASSLQSGVPSRFSGSGSGTDFTLTISSLQPEDFATYYCQHYTSWPRQFTF
GQGTKVEIKR

>B15022-VH
(SEQ ID NO: 127)
EVQLVESGGGLVQPGGSLRLSCAASGYSISSGYYWGWIRQAPGKGLEWIG
ITYPSGGGTNYAQKFQGRVTISRDNSKNTLYLQLNSLRAEDTAVYYCARG
GGLGFDWGQGTLVTVSS

>B15022-VL
(SEQ ID NO: 156)
DIQLTQSPSSLSASVGDRVTITCRASQSIPSFLNWYQQKPGKAPKLLIYA
ASTLQSGVPSRFSGSGSGTDFTLTISSLQPEDFATYYCQQYSSWPRLFTF
GQGTKVEIKR

>B15024-VH
(SEQ ID NO: 127)
EVQLVESGGGLVQPGGSLRLSCAASGYSISSGYYWGWIRQAPGKGLEWIG
ITYPSGGGTNYAQKFQGRVTISRDNSKNTLYLQLNSLRAEDTAVYYCARG
GGLGFDWGQGTLVTVSS

>B15024-VL
(SEQ ID NO: 157)
DIQLTQSPSSLSASVGDRVTITCRASQSIPTFLNWYQQKPGKAPKLLIYA
ASTLQSGVPSRFSGSGSGTDFTLTISSLQPEDFATYYCQHYVSWPRLFTF
GQGTKVEIKR

>B15041-VH
(SEQ ID NO: 127)
EVQLVESGGGLVQPGGSLRLSCAASGYSISSGYYWGWIRQAPGKGLEWIG
ITYPSGGGTNYAQKFQGRVTISRDNSKNTLYLQLNSLRAEDTAVYYCARG
GGLGFDWGQGTLVTVSS

>B15041-VL
(SEQ ID NO: 158)
DIQLTQSPSSLSASVGDRVTITCRASQSIPSFLNWYQQKPGKAPKLLIYA
ASSLQSGVPSRFSGSGSGTDFTLTISSLQPEDFATYYCQHYISWPRQFTF
GQGTKVEIKR

>B15074-VH
(SEQ ID NO: 127)
EVQLVESGGGLVQPGGSLRLSCAASGYSISSGYYWGWIRQAPGKGLEWIG
ITYPSGGGTNYAQKFQGRVTISRDNSKNTLYLQLNSLRAEDTAVYYCARG
GGLGFDWGQGTLVTVSS

>B15074-VL
(SEQ ID NO: 159)
DIQLTQSPSSLSASVGDRVTITCRASQTIPSFLNWYQQKPGKAPKLLIYA
ASTLQSGVPSRFSGSGSGTDFTLTISSLQPEDFATYYCQHYISWPRVFTF
GQGTKVEIKR

>B15082-VH
(SEQ ID NO: 127)
EVQLVESGGGLVQPGGSLRLSCAASGYSISSGYYWGWIRQAPGKGLEWIG
ITYPSGGGTNYAQKFQGRVTISRDNSKNTLYLQLNSLRAEDTAVYYCARG
GGLGFDYWGQGTLVTVSS

>B15082-VL
(SEQ ID NO: 160)
DIQLTQSPSSLSASVGDRVTITCRASQTIPSFLNWYQQKPGKAPKLLIYA
ASSLQSGVPSRFSGSGSGTDFTLTISSLQPEDFATYYCQHYGSWPRRFTF
GQGTKVEIKR

>B13002-VH (SEQ ID NO: 126)
EVQLVESGGGLVQPGGSLRLSCAASGYTFSNYGIHWVRQAPGKGLEWIGW
IYPSGGGTKYAQKFQGRVTISRDNSKNTLYLQLNSLRAEDTAVYYCAREG
GGYGYALDWGQGTLVTVSS

>B13002-VL (SEQ ID NO: 161)
DIQLTQSPSSLSASVGDRVTITCRASQGVSSYLAWYQQKPGKAPKLLIYD
ASNLETGVPSRFSGSGSGTDFTLTISSLQPEDFATYYCQQYDAWPYTFGQ
GTKVEIKR

>B13004-VH (SEQ ID NO: 126)
EVQLVESGGGLVQPGGSLRLSCAASGYTFSNYGIHWVRQAPGKGLEWIGW
IYPSGGGTKYAQKFQGRVTISRDNSKNTLYLQLNSLRAEDTAVYYCAREG
GGYGYALDWGQGTLVTVSS

>B13004-VL (SEQ ID NO: 162)
DIQLTQSPSSLSASVGDRVTITCRASQGISPWLAWYQQKPGKAPKLLIYD
ASNRATGIPSRFSGSGSGTDFTLTISSLQPEDFATYYCQQYDSWPYTFGQ
GTKVEIKR

>B13005-VH (SEQ ID NO: 126)
EVQLVESGGGLVQPGGSLRLSCAASGYTFSNYGIHWVRQAPGKGLEWIGW
IYPSGGGTKYAQKFQGRVTISRDNSKNTLYLQLNSLRAEDTAVYYCAREG
GGYGYALDWGQGTLVTVSS

>B13005-VL (SEQ ID NO: 163)
DIQLTQSPSSLSASVGDRVTITCRASQSVSSYLAWYQQKPGKAPKLLIYD
ASNLETGVPSRFSGSGSGTDFTLTISSLQPEDFATYYCQQYDAWPYTFGQ
GTKVEIKR

In some embodiments, one or more of the above sequences can be converted into IgG, such as IgG1, IgG2, IgG3, and IgG4. Exemplary IgG sequences can have the following VH and/or VL:

>TY21418-VH (SEQ ID NO: 126)
EVQLVESGGGLVQPGGSLRLSCAASGYTFSNYGIHWVRQAPGKGLEWIGW
IYPSGGGTKYAQKFQGRVTISRDNSKNTLYLQLNSLRAEDTAVYYCAREG
GGYGYALDYWGQGTLVTVSS

>TY21418-VL (SEQ ID NO: 161)
DIQLTQSPSSLSASVGDRVTITCRASQGVSSYLAWYQQKPGKAPKLLIYD
ASNLETGVPSRFSGSGSGTDFTLTISSLQPEDFATYYCQQYDAWPYTFGQ
GTKVEIKR

>TY21419-VH (SEQ ID NO: 126)
EVQLVESGGGLVQPGGSLRLSCAASGYTFSNYGIHWVRQAPGKGLEWIGW
IYPSGGGTKYAQKFQGRVTISRDNSKNTLYLQLNSLRAEDTAVYYCAREG
GGYGYALDWGQGTLVTVSS

>TY21419-VL (SEQ ID NO: 162)
DIQLTQSPSSLSASVGDRVTITCRASQGISPWLAWYQQKPGKAPKLLIYD
ASNRATGIPSRFSGSGSGTDFTLTISSLQPEDFATYYCQQYDSWPYTFGQ
GTKVEIKR

>TY21420-VH (SEQ ID NO: 127)
EVQLVESGGGLVQPGGSLRLSCAASGYSISSGYYWGWIRQAPGKGLEWIG
ITYPSGGGTNYAQKFQGRVTISRDNSKNTLYLQLNSLRAEDTAVYYCARG
GGLGFDWGQGTLVTVSS

>TY21420-VL (SEQ ID NO: 155)
DIQLTQSPSSLSASVGDRVTITCRASQTIPSFLNWYQQKPGKAPKLLIYA
ASSLQSGVPSRFSGSGSGTDFTLTISSLQPEDFATYYCQHYTSWPRQFTF
GQGTKVEIKR

>TY21421-VH (SEQ ID NO: 127)
EVQLVESGGGLVQPGGSLRLSCAASGYSISSGYYWGWIRQAPGKGLEWIG
IIYPSGGGTNYAQKFQGRVTISRDNSKNTLYLQLNSLRAEDTAVYYCARG
GGLGFDWGQGTLVTVSS

>TY21421-VL (SEQ ID NO: 158)
DIQLTQSPSSLSASVGDRVTITCRASQSIPSFLNWYQQKPGKAPKLLIYA
ASSLQSGVPSRFSGSGSGTDFTLTISSLQPEDFATYYCQHYISWPRQFTF
GQGTKVEIKR

In some embodiments, the antibody or antigen-binding fragment thereof can include one or more of the following HVR region sequences (e.g., in an IgG):

>TY21418-HVR_H1

(SEQ ID NO: 164)
YTFSNYGIFIWV

>TY21418-HVR_H2

(SEQ ID NO: 165)
IGWIYPSGGGTKYAQKFQGRV

>TY21418-HVR_H3

(SEQ ID NO: 166)
AREGGGYGYALDY

>TY21418-HVR_L1

(SEQ ID NO: 37)
RASQGVSSYLA

>TY21418-HVR_L2

(SEQ ID NO: 64)
DASNLETGV

>TY21418-HVR_L3

(SEQ ID NO: 91)
YCQQYDAWPYT

>TY21419-HVR_H1

(SEQ ID NO: 164)
YTFSNYGIFIWV

>TY21419-HVR_H2

(SEQ ID NO: 165)
IGWIYPSGGGTKYAQKFQGRV

```
>TY21419-HVR_H3
                                (SEQ ID NO: 166)
AREGGGYGYALDY

>TY21419-HVR_L1
                                (SEQ ID NO: 38)
RASQGISPWLA

>TY21419-HVR_L2
                                (SEQ ID NO: 65)
DASNRATGI

>TY21419-HVR_L3
                                (SEQ ID NO: 92)
YCQQYDSWPYT

>TY21420-HVR_H1
                                (SEQ ID NO: 167)
YSISSGYYWGWI

>TY21420-HVR_H2
                                (SEQ ID NO: 168)
IGIIYPSGGGTNYAQKFQGRV

>TY21420-HVR_H3
                                (SEQ ID NO: 169)
ARGGGLGFDY

>TY21420-HVR_L1
                                (SEQ ID NO: 97)
RASQTIPSFLN

>TY21420-HVR_L2
                                (SEQ ID NO: 106)
AASSLQSGV

>TY21420-HVR_L3
                                (SEQ ID NO: 115)
YCQHYTSWPRQFT

>TY21421-HVR_H1
                                (SEQ ID NO: 167)
YSISSGYYWGWI

>TY21421-HVR_H2
                                (SEQ ID NO: 168)
IGIIYPSGGGTNYAQKFQGRV

>TY21421-HVR_H3
                                (SEQ ID NO: 169)
ARGGGLGFDY

>TY21421-HVR_L1
                                (SEQ ID NO: 100)
RASQSIPSFLN

>TY21421-HVR_L2
                                (SEQ ID NO: 109)
AASSLQSGV

>TY21421-HVR_L3
                                (SEQ ID NO: 118)
YCQHYISWPRQFT
```

In certain circumstances there are advantages to using antibody fragments, rather than whole antibodies. Smaller fragment sizes allow for rapid clearance, and may lead to improved access to solid tumors.

Various techniques have been developed for the production of antibody fragments. Traditionally, these fragments were derived via proteolytic digestion of intact antibodies (see, e.g., Morimoto et al., J Biochem Biophys. Method. 24:107-117 (1992); and Brennan et al., Science 229:81 (1985)). However, these fragments can now be produced directly by recombinant host cells. Fab, Fv and scFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 with increase in vivo half-life is described in U.S. Pat. No. 5,869,046. In other embodiments, the antibody of choice is a single chain Fv fragment (scFv). See WO 93/16185; U.S. Pat. Nos. 5,571,894 and 5,587,458. The antibody fragment may also be a "linear antibody", e.g., as described in U.S. Pat. No. 5,641,870. Such linear antibody fragments may be monospecific or bispecific.

Bispecific and Polyspecific Antibodies

Bispecific antibodies (BsAbs) are antibodies that have binding specificities for at least two different epitopes, including those on the same or another protein. Alternatively, one arm can bind to the target antigen, and another arm can be combined with an arm that binds to a triggering molecule on a leukocyte such as a T-cell receptor molecule (e.g., CD3), or Fc receptors for IgG (FcγR) such as FcγR1 (CD64), FcγRII (CD32) and FcγRIII (CD16), so as to focus and localize cellular defense mechanisms to the target antigen-expressing cell. Such antibodies can be derived from full length antibodies or antibody fragments (e.g., F(ab')2 bispecific antibodies).

Bispecific antibodies may also be used to localize cytotoxic agents to cells which express the target antigen. Such antibodies possess one arm that binds the desired antigen and another arm that binds the cytotoxic agent (e.g., saporin, anti-interferon-α, vinca alkoloid, ricin A chain, methotrexate or radioactive isotope hapten). Examples of known bispecific antibodies include anti-ErbB2/anti-FcgRIII (WO 96/16673), anti-ErbB2/anti-FcgRI (U.S. Pat. No. 5,837,234), anti-ErbB2/anti-CD3 (U.S. Pat. No. 5,821,337).

Methods for making bispecific antibodies are known in the art. Traditional production of full length bispecific antibodies is based on the coexpression of two immunoglobulin heavy-chain/light chain pairs, where the two chains have different specificities. Millstein et al., Nature, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., EMBO J., 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecules provides for an easy way of separation. This approach is disclosed in WO 94/04690. For further details of generating bispecific antibodies, see, for example, Suresh et al., Methods in Enzymology 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., Science 229: 81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175: 217-225 (1992) describes the production of fully humanized bispecific antibody F(ab')2 molecules. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., Proc. Natl. Acad. Sci. USA, 90: 6444-6448 (1993) has provided an alternative mechanism for making bispecific/bivalent antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific/bivalent antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147: 60 (1991).

Exemplary bispecific antibodies may bind to two different epitopes on a given molecule. Alternatively, an anti-protein arm may be combined with an arm which binds to a triggering molecule on a leukocyte such as a T-cell receptor molecule (e.g., CD2, CD3, CD28 or B7), or Fc receptors for IgG (FcγR), such as FcγRT (CD64), FcγRII (CD32) and FcγRIII (CD16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

Immunoconjugates

The disclosure encompasses a human anti-PD-L1 antibody conjugated to a therapeutic moiety ("immunoconjugate"), such as a cytotoxin or a chemotherapeutic agent to treat cancer. As used herein, the term "immunoconjugate" refers to an antibody which is chemically or biologically linked to a cytotoxin, a radioactive agent, a cytokine, an interferon, a target or reporter moiety, an enzyme, a toxin, a peptide or protein or a therapeutic agent. The antibody may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antibody drug conjudages and antibody-toxin fusion proteins. In one embodiment, the agent may be a second different antibody to PD-L1. In certain embodiments, the antibody may be conjugated to an agent specific for a tumor cell or a virally infected cell. The type of therapeutic moiety that may be conjugated to the anti-PD-L1 antibody will take into account the condition to be treated and the desired therapeutic effect to be achieved. Examples of suitable agents for forming immunoconjugates are known in the art; see for example, WO 05/103081.

Effector Function Engineering

It may be desirable to modify the antibody of the disclosure with respect to Fc effector function, e.g., so as to modify (e.g., enhance or eliminate) antigen-dependent cell-mediated cyotoxicity (ADCC) and/or complement dependent cytotoxicity (CDC) of the antibody. In a preferred embodiment, Fc effector function of the anti-PD-L1 antibodies is reduced or eliminated. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table 1 below under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | Ala | ala |
| Ser (S) | Thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and its target (e.g., PD-L1, B7.1). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants to the antibodies of the disclosure are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version.

Other Antibody Modifications

The antibodies of the present disclosure can be further modified to contain additional nonproteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in Remington: The Science and Practice of Pharmacy, 20th Ed., Alfonso Gennaro, Ed., Philadelphia College of Pharmacy and Science (2000).

Therapeutic Uses of the Antibodies

The antibodies of the present disclosure are useful for the treatment, prevention, and/or amelioration of disease or disorder or condition such as cancer, autoimmune disease or a viral infection and/or for ameliorating at least one symptom associated with such disease, disorder or condition. In some embodiments of the disclosure, the antibodies described herein are useful for treating subjects suffering from primary or recurrent cancer, including for example, renal cell carcinoma, prostate cancer, ovarian cancer, kidney cancer, colorectal cancer, gastric cancer, breast cancer, head and neck cancer, non-small-cell lung cancer, brain cancer, multiple myeloma, and melanoma. The antibodies may be used to treat early stage or late-stage symptoms of cancer. In one embodiment, an antibody or fragment thereof of the disclosure may be used to treat metastatic cancer. The antibodies are useful in reducing or inhibiting or shrinking tumor growth of both solid tumors and blood cancers. In certain embodiments, the antibodies may be used to prevent relapse of a tumor. In certain embodiments, treatment with an antibody or antigen-binding fragment thereof of the disclosure may lead to more than 50% regression, more than 60% regression, more than 70% regression, more than 80% regression or more than 90% regression of a tumor in a subject. In certain embodiments, the antibodies may be used to increase survival of a subject suffering from cancer.

In certain embodiments, the antibodies of the disclosure are useful to treat subjects suffering from a chronic viral infection. In some embodiments, the antibodies of the disclosure are useful in decreasing viral titers in the host and/or rescuing exhausted T-cells. In one embodiment, an antibody or antigen-binding fragment thereof the disclosure may be administered at a therapeutic dose to a patient with an infection by human immunodeficiency virus (HIV) or human papilloma virus (HPV) or hepatitis B/C virus (HBV/HCV). In a related embodiment, an antibody or antigen-binding fragment thereof of the disclosure may be used to treat an infection by simian immunodeficiency virus (SW) in a simian subject such as cynomolgus. In another embodiment, an antibody or fragment thereof of the disclosure may be used to treat chronic viral infection by lymphocytic choriomeningitis virus (LCMV).

In certain embodiments, a blocking antibody of the present disclosure may be administered in a therapeutically effective amount to a subject suffering from cancer or a viral infection.

In certain embodiments, the antibodies of the disclosure are useful for treating an autoimmune disease, including but not limited to, alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjogren's syndrome, systemic lupus erthyematosus, vitiligo, autoimmune pancreatitis, autoimmune urticaria, autoimmune thrombocytopenic purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis. In certain embodiments, an activating antibody of the disclosure may be used to treat a subject suffering from autoimmune disease.

One or more antibodies of the present disclosure may be administered to relieve or prevent or decrease the severity of one or more of the symptoms or conditions of the disease or disorder.

It is also contemplated herein to use one or more antibodies of the present disclosure prophylactically to patients at risk for developing a disease or disorder such as cancer, and chronic viral infection.

In a further embodiment of the disclosure the present antibodies are used for the preparation of a pharmaceutical composition for treating patients suffering from cancer, autoimmune disease or viral infection. In another embodiment of the disclosure, the present antibodies are used as adjunct therapy with any other agent or any other therapy known to those skilled in the art useful for treating cancer, autoimmune disease or viral infection.

Combination Therapies

Combination therapies may include an anti-PD-L1 antibody of the disclosure and any additional therapeutic agent that may be advantageously combined with an antibody of the disclosure, or with a biologically active fragment of an antibody of the disclosure.

The antibodies of the present disclosure may be combined synergistically with one or more anti-cancer drugs or therapy used to treat cancer, including, for example, renal cell carcinoma, ovarian cancer, prostate cancer, colorectal cancer, non-small-cell lung cancer, and melanoma. It is contemplated herein to use anti-PD-L1 antibodies of the disclosure in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response.

Examples include radiation, chemotherapy, anti-angiogenic agents, and surgery.

In various embodiments, one or more antibodies of the present disclosure may be used in combination with a second antibody to PD-L1, an antibody to PD-1 (e.g., nivolumab), a LAG-3 inhibitor, a CTLA-4 inhibitor (e.g., ipilimumab), a TIM3 inhibitor, a BTLA inhibitor, a TIGIT inhibitor, a CD47 inhibitor, an antagonist of another T-cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGF3) inhibitor, an epidermal growth factor receptor (EGFR) inhibitor (e.g., erlotinib, cetuximab), an agonist to a co-stimulatory receptor (e.g., an agonist to glucocorticoid-induced TNFR-related protein), an antibody to a tumor-specific antigen (e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9), a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, PSMAxCD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any palliative care to treat cancer. In certain embodiments, the anti-PD-L1 antibodies of the present disclosure may be used in combination with cancer vaccines including dendritic cell vaccines, oncolytic viruses, tumor cell vaccines, etc. to augment the anti-tumor response. Examples of cancer vaccines that can be used in combination with anti-PD-L1 antibodies of the present disclosure include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers). In certain embodiments, the anti-PD-L1 antibodies of the present disclosure may be used in combination with a dietary supplement such as anti-oxidants or any palliative care to treat cancer.

In certain embodiments, the anti-PD-L1 antibodies of the disclosure may be administered in combination with radiation therapy in methods to generate long-term durable anti-tumor responses and/or enhance survival of patients with cancer. In some embodiments, the anti-PD-L1 antibodies of the disclosure may be administered prior to, concomitantly or after administering radiation therapy to a cancer patient. For example, radiation therapy may be administered in one or more doses to tumor lesions followed by administration of one or more doses of anti-PD-L1 antibodies of the disclosure. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-PD-L1 antibody of the disclosure. For example, intracranial radiation may be administered to a patient with brain cancer (e.g., glioblastoma multiforme) along with systemic administration of an anti-PD-L1 antibody of the disclosure. In certain embodiments, the anti-PD-L1 antibodies of the disclosure may be administered in combination with radiation therapy and a chemotherapeutic agent (e.g., temozolomide) or a VEGF antagonist (e.g., aflibercept).

The antibodies or fragments thereof of the disclosure may be administered in combination with one or more anti-viral drugs known in the art, including but not limited to, zidovudine, lamivudine, abacavir, ribavirin, lopinavir, efavirenz, cobicistat, tenofovir, rilpivirine and corticosteroids. In some embodiments, the anti-PD-L1 antibodies of the disclosure may be administered in combination with a LAG3 inhibitor, a CTLA-4 inhibitor, a PD-1 inhibitor or any antagonist of another T-cell co-inhibitor to treat chronic viral infection.

The antibodies of fragments thereof of the disclosure may be used in combination with any drug or therapy known in the art (e.g., corticosteroids and other immunosuppressants) to treat an autoimmune disease or disorder including, but not limited to, alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjogren's syndrome, systemic lupus erthyematosus, vitiligo, autoimmune pancreatitis, autoimmune urticaira, autoimmune thrombocytopenic purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis.

The additional therapeutically active component(s) may be administered prior to, concurrent with, or after the administration of the anti-PD-L1 antibody of the present disclosure. For purposes of the present disclosure, such administration regimens are considered the administration of an anti-PD-L1 antibody "in combination with" a second therapeutically active component.

The additional therapeutically active component(s) may be administered to a subject prior to administration of an anti-PD-L1 antibody of the present disclosure. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-PD-L1 antibody of the present disclosure. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-PD-L1 antibody of the present disclosure. "Concurrent" administration, for purposes of the present disclosure, includes, e.g., administration of an anti-PD-L1 antibody and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-PD-L1 antibody and the additional therapeutically active component may be administered intravenously, subcutaneously, etc.); alternatively, each dosage form may be administered via a different route (e.g., the anti-PD-L1 antibody may be administered intravenously, and the additional therapeutically active component may be administered subcutaneously). In any event, administering the components in a single dosage from, in separate dosage forms by the same route, or in separate dosage forms by different routes are all considered "concurrent administration," for purposes of the present disclosure. For purposes of the present disclosure, administration of an anti-PD-L1 antibody "prior to", "concurrent with," or "after" (as those terms are defined herein above) administration of an additional therapeutically active component is considered administration of an anti-PD-L1 antibody "in combination with" an additional therapeutically active component).

The present disclosure includes pharmaceutical compositions in which an anti-PD-L1 antibody of the present disclosure is co-formulated with one or more of the additional therapeutically active component(s) as described elsewhere herein using a variety of dosage combinations.

In exemplary embodiments in which an anti-PD-L1 antibody of the disclosure is administered in combination with a VEGF antagonist (e.g., a VEGF trap such as aflibercept), including administration of co-formulations comprising an anti-PD-L1 antibody and a VEGF antagonist, the individual components may be administered to a subject and/or co-formulated using a variety of dosage combinations. For example, the anti-PD-L1 antibody may be administered to a subject and/or contained in a co-formulation in an amount selected from the group consisting of 0.01 mg, 0.02 mg, 0.03 mg, 0.04 mg, 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, 6.0 mg, 7.0 mg, 8.0 mg, 9.0 mg, and 10.0 mg; and the VEGF antagonist (e.g., a VEGF trap such as aflibercept) may be administered to the subject and/or contained in a co-formulation in an amount selected from the group consisting of 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg and 3.0 mg. The combinations/co-formulations may be administered to a subject according to any of the administration regimens disclosed elsewhere herein, including, e.g., twice a week, once every week, once every 2 weeks, once every 3 weeks, once every month, once every 2 months, once every 3 months, once every 4 months, once every 5 months, once every 6 months, etc.

Diagnostic Uses of the Antibodies

The anti-PD-L1 antibodies of the present disclosure may be used to detect and/or measure PD-L1 in a sample, e.g., for diagnostic purposes. Some embodiments contemplate the use of one or more antibodies of the present disclosure in assays to detect a disease or disorder such as cancer, autoimmune disease or chronic viral infection. Exemplary diagnostic assays for PD-L1 may comprise, e.g., contacting a sample, obtained from a patient, with an anti-PD-L1 antibody of the disclosure, wherein the anti-PD-L1 antibody is labeled with a detectable label or reporter molecule or used as a capture ligand to selectively isolate PD-L1 from patient samples. Alternatively, an unlabeled anti-PD-L1 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure PD-L1 in a sample include enzyme-linked immunosorbent assay (ELISA), radioimmunoassay (RIA), and fluorescence-activated cell sorting (FACS).

Samples that can be used in PD-L1 diagnostic assays according to the present disclosure include any tissue or fluid sample obtainable from a patient, which contains detectable quantities of either PD-L1 protein, or fragments thereof, under normal or pathological conditions.

Generally, levels of PD-L1 in a particular sample obtained from a healthy patient (e.g., a patient not afflicted with cancer or an autoimmune disease) will be measured to initially establish a baseline, or standard, level of PD-L1. This baseline level of PD-L1 can then be compared against the levels of PD-L1 measured in samples obtained from individuals suspected of having a cancer-related condition, or symptoms associated with such condition.

The antibodies specific for PD-L1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Aspects of the disclosure relate to use of the disclosed antibodies as markers for predicting prognosis of cancer or an autoimmune disorder in patients. Antibodies of the present disclosure may be used in diagnostic assays to evaluate prognosis of cancer in a patient and to predict survival.

Pharmaceutical Formulations

Therapeutic formulations are prepared for storage by mixing the active ingredient having the desired degree of purity with optional pharmaceutically acceptable carriers, excipients or stabilizers (Remington: The Science and Practice of Pharmacy, 20th Ed., Lippincott Williams & Wiklins, Pub., Gennaro Ed., Philadelphia, Pa. 2000). Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g., Zn-protein complexes); chelating agents such as EDTA and/or non-ionic surfactants.

When the therapeutic agent is an antibody fragment, the smallest inhibitory fragment which specifically binds to the binding domain of the target protein is preferred. For example, based upon the variable region sequences of an antibody, antibody fragments or even peptide molecules can be designed which retain the ability to bind the target protein sequence. Such peptides can be synthesized chemically and/or produced by recombinant DNA technology (see, e.g., Marasco et al., Proc. Natl. Acad. Sci. USA 90: 7889-7893 [1993]).

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present disclosure include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives are added to retard microbial growth, and are typically present in a range from 0.2%-1.0% (w/v). Suitable preservatives for use with the present disclosure include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl cellulose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, supra.

Stability of the proteins and antibodies described herein may be enhanced through the use of non-toxic "water-soluble polyvalent metal salts". Examples include $Ca^{2+}$, $Mg^{2+}$, $Zn^{2+}$, $Fe^{2+}$, $Fe^{3+}$, $Cu^{2+}$, $Sn^{2+}$, $Sn^{4+}$, $Al^{2+}$ and $Al^{3+}$. Example anions that can form water soluble salts with the above polyvalent metal cations include those formed from inorganic acids and/or organic acids. Such water-soluble salts have solubility in water (at 20° C.) of at least about 20 mg/ml, alternatively at least about 100 mg/ml, alternatively at least about 200 mg/ml.

Suitable inorganic acids that can be used to form the "water soluble polyvalent metal salts" include hydrochloric, acetic, sulfuric, nitric, thiocyanic and phosphoric acid. Suitable organic acids that can be used include aliphatic carboxylic acid and aromatic acids. Aliphatic acids within this definition may be defined as saturated or unsaturated C2-9 carboxylic acids (e.g., aliphatic mono-, di- and tri-carboxylic acids). For example, exemplary monocarboxylic acids within this definition include the saturated C2-9 monocarboxylic acids acetic, proprionic, butyric, valeric, caproic, enanthic, caprylic pelargonic and capryonic, and the unsaturated C2-9 monocarboxylic acids acrylic, propriolic methacrylic, crotonic and isocrotonic acids. Exemplary dicarboxylic acids include the saturated C2-9 dicarboxylic acids malonic, succinic, glutaric, adipic and pimelic, while unsaturated C2-9 dicarboxylic acids include maleic, fumaric, citraconic and mesaconic acids. Exemplary tricarboxylic acids include the saturated C2-9 tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated polypeptides of this disclosure include, for example: (1) the inorganic acid metal salts of halides (e.g., zinc chloride, calcium chloride), sulfates, nitrates, phosphates and thiocyanates; (2) the aliphatic carboxylic acid metal salts (e.g., calcium acetate, zinc acetate, calcium proprionate, zinc glycolate, calcium lactate, zinc lactate and zinc tartrate); and (3) the aromatic carboxylic acid metal salts of benzoates (e.g., zinc benzoate) and salicylates.

Pharmaceutical Dosages

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

When in vivo administration of the polypeptides or antibodies described herein are used, normal dosage amounts may vary from about 10 ng/kg up to about 100 mg/kg of mammal body weight or more per day, preferably about 1 mg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is within the scope of the disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Administration of the Formulation

The formulations of the present disclosure, including but not limited to reconstituted and liquid formulations, are administered to a mammal in need of treatment with the anti-PD-L1 antibodies, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In preferred embodiments, the formulations are administered to the mammal by subcutaneous (i.e., beneath the skin) administration. For such purposes, the formulation may be injected using a syringe. However, other devices for administration of the formulation are available such as injection devices (e.g., the INJECT-EASE™ and GENJECT™ devices); injector pens (such as the GENPEN™); auto-injector devices, needleless devices (e.g., MEDIJECTOR™ and BIOJECTOR™); and subcutaneous patch delivery systems.

In a specific embodiment, the present disclosure is directed to kits for a single dose-administration unit. Such kits comprise a container of an aqueous formulation of therapeutic protein or antibody, including both single or multi-chambered pre-filled syringes. Exemplary pre-filled syringes are available from Vetter GmbH, Ravensburg, Germany.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to anti-PD-L1 antibody, the format of the formulation used, and the discretion of the attending physician. The anti-PD-L1 antibody is suitably administered to the patient at one time or over a series of treatments and may be administered to the patient at any time from diagnosis onwards. The anti-PD-L1 antibody may be administered as the sole treatment or in conjunction with other drugs or therapies useful in treating the condition in question.

For anti-PD-L1 antibodies, an initial candidate dosage can range from about 0.1-20 mg/kg for administration to the patient, which can take the form of one or more separate administrations. However, other dosage regimens may be useful. The progress of such therapy is easily monitored by conventional techniques.

According to certain embodiments of the present disclosure, multiple doses of an anti-PD-L1 antibody (or a pharmaceutical composition comprising a combination of an anti-PD-L1 antibody and any of the additional therapeutically active agents mentioned herein) may be administered to a subject over a defined time course. The methods according to this aspect of the disclosure comprise sequentially administering to a subject multiple doses of an anti-PD-L1 antibody of the disclosure. As used herein, "sequentially administering" means that each dose of anti-PD-L1 antibody is administered to the subject at a different point in time, e.g., on different days separated by a predetermined interval (e.g., hours, days, weeks or months). The present disclosure includes methods which comprise sequentially administering to the patient a single initial dose of an anti-PD-L1 antibody, followed by one or more secondary doses of the anti-PD-L1 antibody, and optionally followed by one or more tertiary doses of the anti-PD-L1 antibody. The anti-PD-L1 antibody may be administered at a dose of between 0.1 mg/kg to about 100 mg/kg.

The terms "initial dose," "secondary doses," and "tertiary doses," refer to the temporal sequence of administration of the anti-PD-L1 antibody of the disclosure. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-PD-L1 antibody, but generally may differ from one another in terms of frequency of administration. In certain embodiments, however, the amount of anti-PD-L1 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-PD-L1 antibody which is administered to a patient prior to the administration of the very next dose in the sequence with no intervening doses.

The methods according to this aspect of the disclosure may comprise administering to a patient any number of secondary and/or tertiary doses of an anti-PD-L1 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of, e.g., once a month (e.g., two, three, four, or more loading doses administered once a month), then the maintenance doses may be administered to the patient once every five weeks, once every six weeks, once every seven weeks, once every eight weeks, once every ten weeks, once every twelve weeks, etc.).

Articles of Manufacture

In another embodiment of the disclosure, an article of manufacture is provided which contains the formulation and preferably provides instructions for its use. The article of manufacture comprises a container. Suitable containers include, for example, bottles, vials (e.g., dual chamber vials), syringes (such as single or dual chamber syringes) and test tubes. The container may be formed from a variety of materials such as glass or plastic. The container holds the formulation. The label, which is on, or associated with the container may indicate directions for reconstitution and/or use. The label may further indicate that the formulation is useful or intended for subcutaneous administration, and/or for the treatment of a T-cell dysfunctional disorder. The container holding the formulation may be a multi-use vial, which allows for repeat administrations (e.g., from 2-6 administrations) of the reconstituted formulation. The article of manufacture may further comprise a second container comprising a suitable diluent (e.g., BWFI). Upon mixing of the diluent and the lyophilized formulation, the final protein concentration in the reconstituted formulation will generally be at least 50 mg/ml. The article of manufacture may further include other materials desirable from a commercial and user standpoint, including other buffers, diluents, filters, needles, syringes, and package inserts with instructions for use.

The disclosure will be more fully understood by reference to the following examples. They should not, however, be construed as limiting the scope of the disclosure. All citations throughout the disclosure are hereby expressly incorporated by reference.

In another embodiment, the disclosure provides for an article of manufacture comprising the formulations described herein for administration in an auto-injector device. An auto-injector can be described as an injection device that upon activation, will deliver its contents without additional necessary action from the patient or administrator. They are particularly suited for self-medication of therapeutic formulations when the delivery rate must be constant and the time of delivery is greater than a few moments.

EXAMPLES

Example 1

Discovery of Primary Fabs that Specifically Binds to PD-L1

Proprietary phagemid libraries were employed to pan against the human antigen PD-L1-His (Sino Biological #10084-H08H). The antigen was biotinylated and captured by Dynabeads (M280, Streptavidin, Invitrogen #60210) for panning through KingFisher (Thermo Scientific) according to manufacturer's instructions. Standard phage panning protocols were employed in the process. Three to four rounds of panning were conducted, and then single-colony supernatant ELISA was performed to identify the primary Fabs that bind to human PD-L1. The primary hits were defined as those whose ELISA signals were at least twice that of background. A total of 960 clones were picked for supernatant ELISA analysis, and 101 clones with unique sequences were discovered. These unique primary hits can be separated into two groups based on Fab ELISA assays: one group is specific to human PD-L1, while the other group cross-reacts with both human and mouse PD-L1. The KD for most of the primary hits ranged from 0.5 nM to 10 nM as measured by Bio-Layer Interferometry (BLI) assays.

It should be noted that KD numbers may vary by 10-20% in different measurement methods with the same antibody. The difference in KD may also have resulted from the monomeric or dimeric forms of PD-L1. Surprisingly, when PD-L1-Fc (presumably dimeric) was immobilized on chip surface, significantly higher affinity (<15 pM) was observed compared to conventional antibodies in the same assay.

12 of the primary hits, consisting of 7 cross-reactive hits and 5 human specific hits, were selected for further affinity maturation through light chain shuffling. Affinity maturation was performed through phage display or yeast display. A total of 36 hits with enhanced affinity against PD-L1 were identified, and they were separated into two groups: one group with 27 Fab hits bind to human PD-L1 (later confirmed to bind to monkey PD-L1 as well), and the other group with 9 Fab hits bind to PD-L1 from human and mouse (later confirmed to bind to monkey PD-L1 as well). The Fabs corresponding to the unique hits were expressed in *E. coli* and purified. Their affinities against human or mouse PD-L1 were measured by BLI assays. Briefly, the AHC sensors (Anti-Human IgG Fc Capture Dip and Read Biosensors) were used to capture PD-L1-Fc fusion protein (Sino Biological Cat #10084-H02H), and dipped into wells containing purified Fabs that were diluted to 5-10 µg/ml with kinetic buffer (10 mM HEPES, 150 mM NaCl, 3 mM EDTA, 0.005% v/v Surfactant P20, pH 7.4). The acquired data were processed with Data Acquisition software 7.1, and kinetic data were fitted to a 1:1 Langmuir binding model. The affinity and kinetic parameters (with background subtracted) are listed in Table 2. The amino acid sequences of all VH and VL are shown in SEQ ID NOs: 126-163.

A group of 27 Fab hits bind to human and monkey PD-L1. They have identical VH (SEQ ID NO: 126), but different VL.

A group of 9 Fab hits bind to PD-L1 from human, monkey and mouse, they have identical VH (SEQ ID NO: 127), but different VL.

TABLE 2

Affinity of Fabs against human or mouse PD-L1 measured by ForteBio

| Fab_ID | PD-L1 Species used for Kd assay | Fab_Kd |
|---|---|---|
| Human mouse cross reactive | | |
| B14032 | Human | 5.11E−09 |
| B14032 | Mouse | 4.84E−09 |
| B15012 | Human | 1.76E−09 |
| B15012 | Mouse | 2.03E−09 |
| B15014 | Human | 2.43E−09 |
| B15014 | Mouse | 3.87E−09 |
| B15016 | Human | 3.56E−09 |
| B15016 | Mouse | 2.84E−09 |
| B15022 | Human | 3.68E−09 |
| B15022 | Mouse | 3.03E−09 |
| B15024 | Human | 4.52E−09 |
| B15024 | Mouse | 3.48E−09 |
| B15041 | Human | 1.68E−09 |
| B15041 | Mouse | 1.67E−09 |
| B15074 | Human | 4.31E−09 |
| B15074 | Mouse | 2.98E−09 |
| B15082 | Human | 4.79E−09 |
| B15082 | Mouse | 3.23E−09 |
| Human (and monkey) only | | |
| B14033 | Human | 8.75E−10 |
| B14614 | Human | 3.53E−10 |
| B14615 | Human | 2.28E−10 |
| B14617 | Human | 2.88E−10 |
| B14622 | Human | 2.74E−10 |
| B14627 | Human | 1.82E−10 |
| B14631 | Human | 1.83E−10 |
| B14633 | Human | 3.22E−10 |
| B14634 | Human | 2.07E−10 |
| B14638 | Human | 3.14E−10 |
| B14642 | Human | 1.89E−10 |
| B14644 | Human | 2.48E−10 |
| B14645 | Human | 2.96E−10 |
| B14650 | Human | 3.57E−10 |
| B14651 | Human | 3.01E−10 |
| B14652 | Human | 2.94E−10 |
| B14654 | Human | 2.32E−10 |
| B14658 | Human | 1.42E−10 |
| B14665 | Human | 3.69E−10 |
| B14673 | Human | 3.23E−10 |
| B14674 | Human | 5.02E−10 |
| B14681 | Human | 5.43E−10 |
| B14689 | Human | 1.63E−10 |
| B14690 | Human | 4.67E−10 |
| B13002 | Human | 2.51E−10 |
| B13004 | Human | 3.00E−10 |
| B13005 | Human | 3.46E−10 |

Example 2

IgG Conversion and Expression: TY21418, TY21419, TY21420 and TY21421

Four Fabs, B13002, B13004, B15016, and B15041 were chosen to be converted into IgG1 s. Two of them (B13002 and B13004) were specific to human PD-L1, while the other two (B15016 and B15041) were cross-reactive with human and mouse PD-L1. Their heavy chains and light chains were cloned into the mammalian expression vector pCDNA3.3 (Thermo Fisher Scientific, cat #K830001) separately in IgG1 isotype. The heavy and light chains of the reference antibody (YW243.55.570) was also cloned into pCDNA3.3 in IgG1 isotype (Reference U.S. Pat. No. 8,217,149 B2 (Genentech) Anti-PD-L1 antibodies, compositions and articles of manufacture). The IgGs used in herein are shown in Table 3.

```
>YW243.55.S70_VH from U.S. Pat. No. 8217149 B2
                                       (SEQ ID NO. 170)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSA

>YW243.55.S70_VL from U.S. Pat. No. U58217149 B2
                                       (SEQ ID NO. 171)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR
```

TABLE 3

List of IgGs

| IgG | Fab | Isotype | Specificity | Description |
|---|---|---|---|---|
| TY21418 | B13002 | IgG1 | Human, Monkey | Adagene mAb |
| TY21419 | B13004 | IgG1 | Human, Monkey | Adagene mAb |
| TY21420 | B15016 | IgG1 | Human, Monkey, Mouse | Adagene mAb |
| TY21421 | B15041 | IgG1 | Human, Monkey, Mouse | Adagene mAb |
| Reference | YW243.55.S70 | IgG1 | Human, Monkey, Mouse | Reference |

Pairs of plasmids were transiently transfected into HEK293F cells. After six days, the supernatants were harvested, cleared by centrifugation and filtration, and IgGs were purified with standard protein A affinity chromatography (MabSelect SuRe, GE Healthcare). The IgGs were eluted and neutralized, and buffer exchanged into PB buffer (20 mM sodium phosphate, 150 mM NaCl, pH 7.0). Protein concentrations were determined by UV-spectrophotometry, and IgG purity was analyzed under denaturing, reducing and non-reducing conditions by SDS-PAGE or SEC-HPLC.

Example 3

PD-L1 Antibodies Selectively Bind to PD-L1 Expressed on Mammalian Cell Surface

The selectivity of antibodies for PD-L1 was evaluated using flow cytometry. Briefly, human, rhesus and mouse PD-L1, as well as human PD1, CTLA4, LAG3, TIM3 and B7-H3 were transiently expressed on the membrane of HEK293F cells individually. Transfected cells were washed in pre-chilled staining buffer (PBS supplemented with 2% FBS), then incubated with 100 nM test antibodies for 1 hr on ice. Cells were washed twice with staining buffer, and Phycoerythrin (PE)-conjugated mouse anti-human Fc antibodies were added and incubated for 30 min on ice. Samples were washed once with staining buffer prior to analysis by flow cytometry. As shown in FIG. 1, TY21418, TY21419, TY21420, TY21421 and the reference antibody strongly bind to human and rhesus PD-L1, while only TY21420, TY21421 and the reference antibody were able to bind to mouse PD-L1, consistent with earlier observations based on ELISA with purified Fab proteins. Importantly, the candidate antibodies TY21418, TY21419, TY21420 and TY21421 only bind to PD-L1, and none of them showed any visible binding to other tested immune checkpoint molecules.

Example 4

Blocking of PD1 and PD-L1 Interaction by Antibodies

To determine whether the candidate antibodies block the interaction between PD-L1 and its ligand PD1, three types of assays were performed. They included flow cytometry, BLI and ELISA. All three methods demonstrated that the four candidate antibodies TY21418, TY21419, TY21420 and TY21421 completely block the binding of PD1 to PD-L1.

Figure 2:
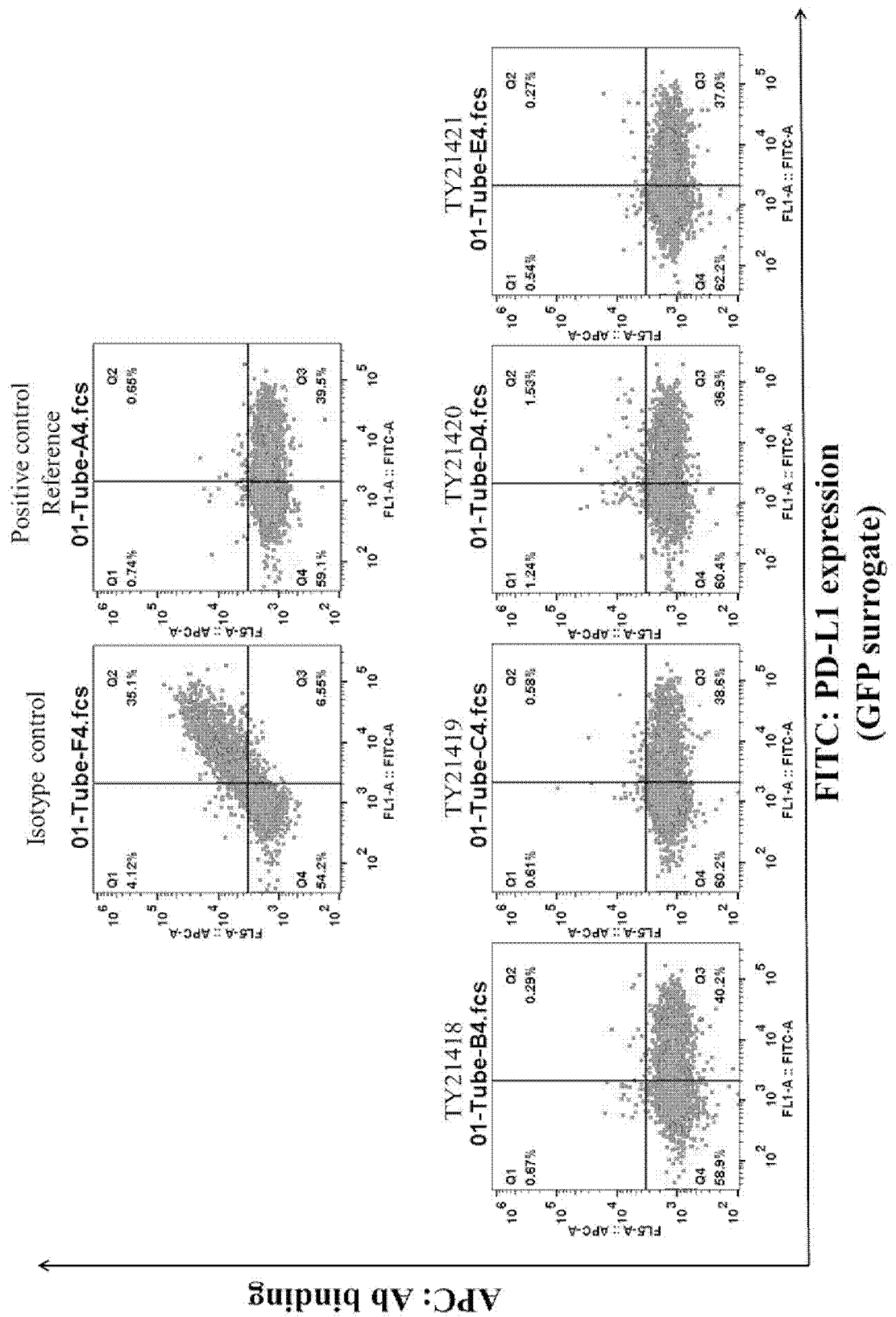
FIG. 2 shows the exemplary antibodies completely block the binding of PD-L1 and its ligand PD1 by flow cytometry-based assays.

4a. Blocking of Binding Between PD1 and PD-L1 as Measured Through Flow Cytometry The plasmid encoding full-length human PD-L1 was transiently expressed in HEK293F cells. Cells were washed with staining buffer (PBS supplemented with 1% BSA) and resuspended in staining buffer containing 100 nM test antibodies. After incubation on ice for 1 hr, 100 nM biotinylated PD1-His (Sino Biological cat #10377-H08H) were added to each well and incubated for another 30 min on ice. Cells were washed once with 1×PBSA, and 100 μL staining buffer containing Alexa fluor 633 conjugated streptavidin were added and incubated on ice for 30 min. Cells were then washed once and analyzed by CytoFlex flow cytometry. As shown in FIG. 2, all four candidate antibodies, as well as the reference antibody, effectively block binding between PD-L1 and PD1.

4b. Blocking of the Binding Between PD1 and PD-L1 as Measured Through BLI

Figure 3:
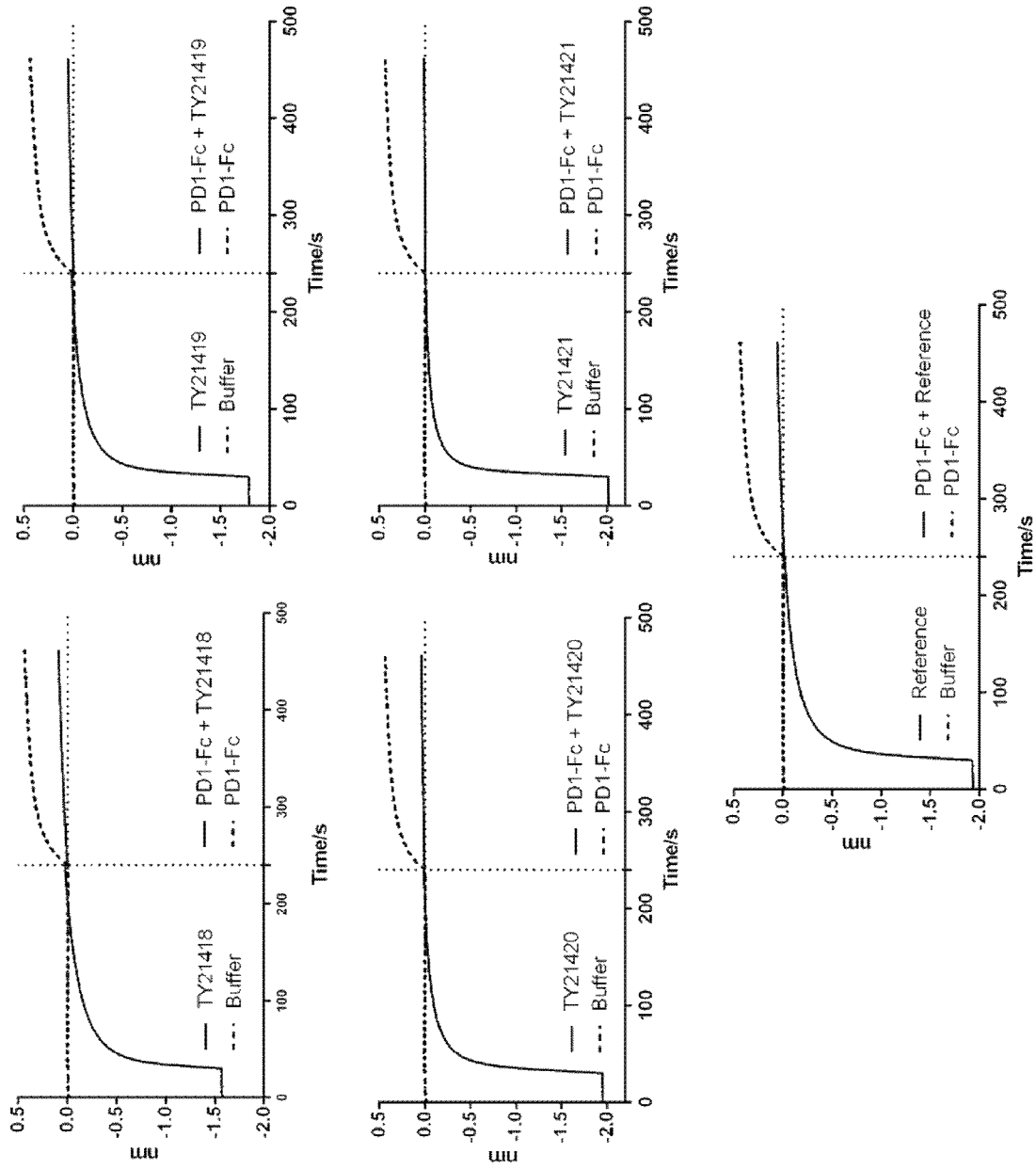
FIG. 3 shows the exemplary antibodies completely block the binding of PD-L1 and its ligand PD1 by BLI assays.

In this assay, biotinylated PD-L1-His was adjusted to 4 μg/ml, and loaded onto Streptavidin (SA) Dip and Read Biosensors in parallel. After 30 sec equilibrium in kinetic buffer, the biosensors were dipped into wells containing different antibodies adjusted to 37.5 μg/ml in kinetic buffer. After the signals reached plateau, the biosensors were dipped into wells containing mixture of PD1-Fc (5 μg/ml) and corresponding antibodies (37.5 μg/ml). The increase of signal indicated effective binding. As evidenced in FIG. 3, all four candidate antibodies, as well as the reference antibody, prevented the increase of PD1 signal, suggesting that they effectively block interaction between PD-L1 and PD1.

4c. Blocking of the Binding Between PD1 and PD-L1 as Measured Through ELISA

Figure 4:
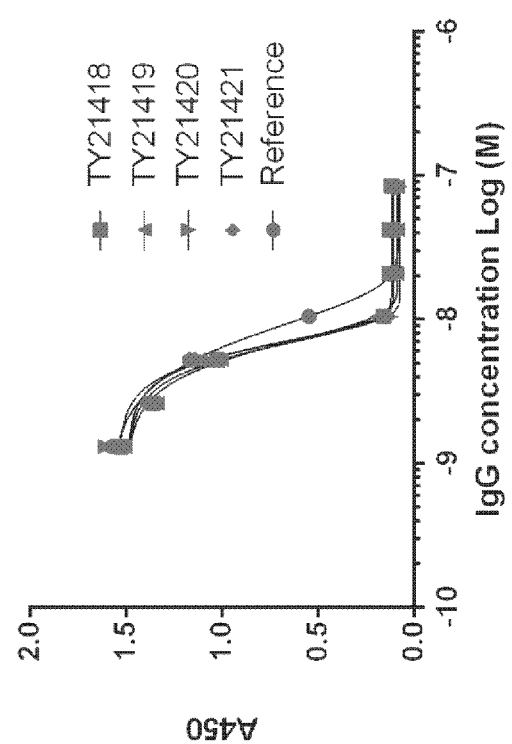
FIG. 4 shows the exemplary antibodies completely block the binding of PD-L1 and its ligand PD1 by ELISA assays.

Recombinant human PD1-Fc was diluted to 1 μg/mL in PBS and coated on Maxisorp plate at 4° C. overnight. Plates were blocked with PBS supplemented with 3% non-fat milk at 37° C. for 1 hr. After washing, a total volume of 100 μL mixture of 50 μL biotinylated PD-L1-Fc (3 μg/mL) and various concentrations of test antibodies (eight 1:2 serial dilutions ranging from 50 μg/mL to 0.195 μg/mL) were added to each well and incubated at 37° C. for 1 hr. Plates were washed three times and 100 μL HRP conjugated neutravidin (1:1,000) were added to each well and incubated at 37° C. for 1 hr. Plates were washed as previously described and 50 μL TMB substrate solution was added and incubated at room temperature. Each reaction was stopped by 50 μL H$_2$SO$_4$. As shown in FIG. 4, all four candidate antibodies, as well as the reference antibody, effectively block the binding of PD-L1 to PD1.

Example 5

Characterization of Antibodies Binding to PD-L1

The binding affinity of the antibodies to human, rhesus, mouse and rat PD-L1 were measured by Biacore. The results were summarized in Tables 4-6.

5a. Measurement of Binding Affinity and Kinetics of TY21418 and TY21419 to Human PD-L1 by SPR Binding affinity and kinetics of TY21418 and TY21419 against human PD-L1 protein were examined by surface plasmon resonance (SPR) analysis using a Biacore™ T200 instrument (Biacore AB, Uppsala, Sweden) according to the manufacturer's guidelines. Anti-Human IgG (Fc) antibody from Human Antibody Capture Kit (GE BR-1008-39) was immobilized on CM5 chips by coupling of its amine groups onto carboxylated surfaces of sensor chips according to the instructions of Amine Coupling kit (GE Biacore #BR-1000-50). The immobilized Anti-Human IgG (Fc) antibody was used to capture TY21418, TY21419, or the reference antibody. Finally, six concentrations (3.13, 6.25, 12.5, 25, 50, 100) (nM) (diluted in running buffer) of human PD-L1-His6 (Sino Biological #10084-H08H) were injected at a flow rate of 30 μl/min for 300 seconds, and the dissociation time was 300 seconds. The running buffer used was 1×HBS-EP (10 mM HEPES, 150 mM NaCl, 3 mM EDTA, 0.005% v/v Surfactant P20, pH 7.4 at 25° C.). Corresponding controls were conducted in each case using a blank flow cell with no protein immobilized for "background" subtraction. The association and dissociation curves were fitted to a 1:1 Langmuir binding model using BIAcore T200 Evaluation Software (Biacore AB, Uppsala, Sweden) according to the manufacturer's guidelines. As shown in Table 4, both TY21418 and TY21419 bind to human PD-L1 with sub-nanomolar affinity, similar to the reference antibody. However, In contrast to the reference antibody, neither TY21418 nor TY21419 showed any binding to mouse PD-L1 in Biacore.

TABLE 4

Binding affinity of TY21418 and TY21419 to human PD-L1

| | Biacore | | |
|---|---|---|---|
| | Kon (1/Ms) | Koff (1/s) | KD (M) |
| TY21418 | 4.48E+05 | 1.79E−04 | 3.99E−10 |
| TY21419 | 3.07E+05 | 1.43E−04 | 4.65E−10 |
| Reference | 4.32E+05 | 1.33E−04 | 3.07E−10 |

5b. Measurement of Binding Affinity and Kinetics of TY21421 to Human PD-L1 by SPR Binding affinity and kinetics of TY21421 against human PD-L1 protein were similarly examined by SPR analysis using a Biacore™ T200 instrument (Biacore AB, Uppsala, Sweden), except that human PD-L1-Fc fusion protein was directly immobilized on CM5 chip to 300 RU, and two-fold serial dilutions (0.098 nM to 1.563 nM) of IgGs in running buffer (HBS-EP) were injected at 25° C. with a flow rate of 30 μmin for 300 seconds, followed by 1,200 seconds of dissociation time. The association and dissociation curves were fitted to a 1:1 Langmuir binding model using BIAcore T200 Evaluation Software (Biacore AB, Uppsala, Sweden) according to the manufacturer's guidelines. As shown in Table 5, TY21421 binds to immobilized human PD-L1-Fc with extremely high affinity (KD<10 pM), similar or slightly better than the reference antibody.

TABLE 5

Binding affinity of TY21421 to immobilized human PD-L1-Fc

| | Biacore | | |
|---|---|---|---|
| | Kon (1/Ms) | Koff (1/s) | KD (M) |
| TY21421 | 6.64E+06 | 5.73E−05 | 8.63E−12 |
| Reference | 5.50E+05 | 5.61E−06 | 1.02E−11 |

5c. Measurement of Binding Affinity and Kinetics of TY21421 to PD-L1 from Other Species by SPR Binding affinity and kinetics of TY21421 against PD-L1 protein from human, rhesus (Sino Biological cat #90251-C02H), mouse and rat (Sino Biological cat #80450-R08H) were similarly examined by SPR analysis using a Biacore™ T200 instrument (Biacore AB, Uppsala, Sweden), except that the PD-L1-Fc fusion proteins from human, rhesus, mouse and rat were directly immobilized on CM5 chip to around 500 RU, and two-fold serial dilutions (0.098 nM to 1.563 nM) of IgGs in running buffer (HBS-EP) were injected at 25° C. with a flow rate of 30 μl/min for 300 seconds, followed by 1,200 seconds of dissociation time. The association and dissociation curves were fitted to a 1:1 Langmuir binding model using BIAcore T200 Evaluation Software (Biacore AB, Uppsala, Sweden) according to the manufacturer's guidelines. As shown in Table 6, TY21421 binds to immobilized PD-L1 from all the tested species with picomolar affinity, although its affinity for rat PD-L1 is slightly worse (KD=20.9 pM) compared with PD-L1 from human, rhesus or mouse.

TABLE 6

Binding affinity of TY21421 to immobilized PD-L1 from different species

| | Biacore | | |
|---|---|---|---|
| | Kon (1/Ms) | Koff (1/s) | KD (M) |
| Human | 4.80E+06 | 2.97E−05 | 6.19E−12 |
| Cynomolgus | 3.93E+06 | 7.27E−06 | 1.85E−12 |
| Mouse | 1.11E+07 | 2.06E−05 | 1.86E−12 |
| Rat | 5.07E+06 | 1.06E−04 | 2.09E−11 |

Figure 5:
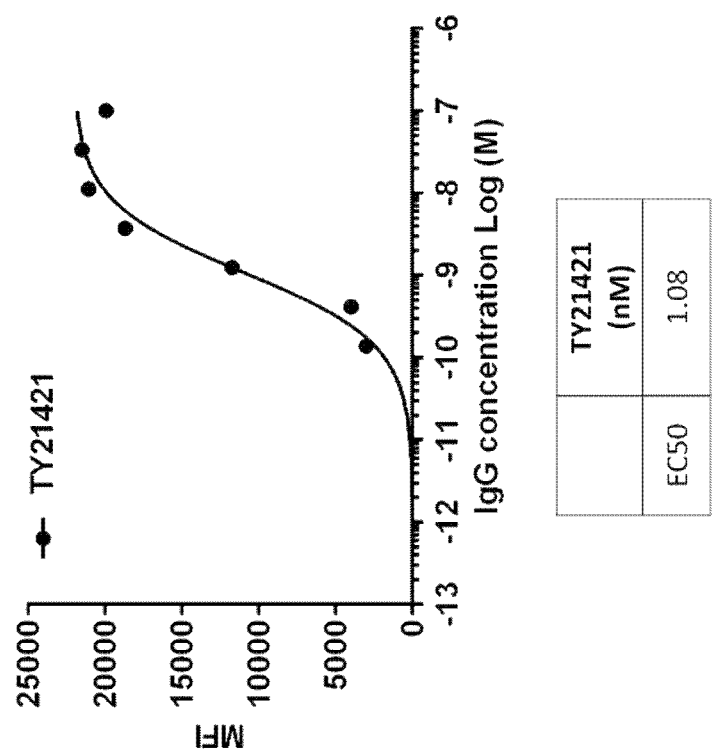
FIG. 5 shows one exemplary antibody TY21421 binds to human PD-L1 expressed on mammalian cell surface with EC50 around 1 nM.

5d. Measurement of EC50 of TY21421 to PD-L1 Expressed on Cell Surface by Flow Cytometry To measure the affinity of TY21421 to PD-L1 expressed on cell surface, a stable cell line 293T-002 (Crownbio #C2005) expressing PD-L1 on its membrane was employed. Briefly, the cells were washed once with cold FACS buffer (1×PBS supplemented with 1% BSA), and then incubated with 3-fold serial dilutions of TY21421 (starting from 100 nM) for 1 hr on ice, washed twice with pre-chilled FACS buffer, and incubated with Allophycocyanin (APC) conjugated mouse anti-human FC antibodies for 30 min on ice. The cells were washed once prior to analysis by flow cytometry (Beckman® CytoFlex). As shown in FIG. 5, TY21421 strongly binds to PD-L1 expressed on cell surface with an EC50 of 1.08 nM,

Example 6

Antibody Binding to Cell Surface PD-L1 after Fixation with Paraformaldehyde

Figure 6:
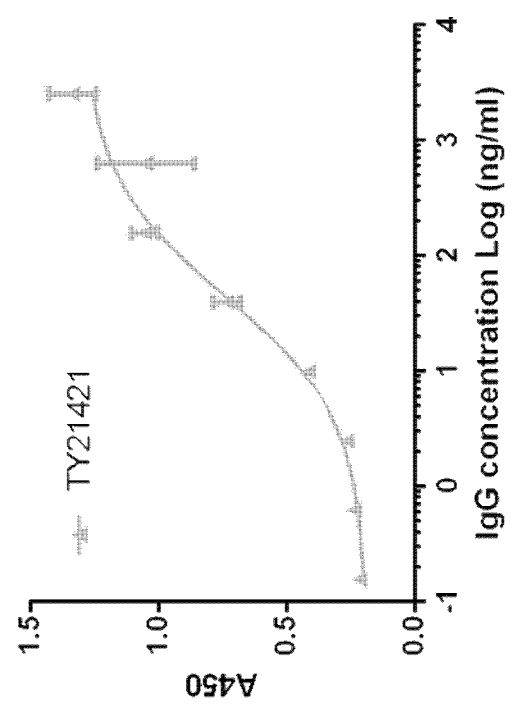
FIG. 6 shows one exemplary antibody TY21421 binds to cell surface PD-L1 that is fixed with paraformaldehyde.

Antibodies were also examined for their ability to bind to cell surface PD-L1 after fixation with paraformaldehyde. Briefly, 10,000 PD-L1-expressing HCC827 human cells (Cell Bank, Type Culture Collection of Chinese Academy of Sciences) were plated in a 96 well plate. After overnight incubation in tissue culture incubator the cells were fixed with 4% paraformaldehyde and blocked with 1% BSA. Serial dilutions of TY21421 were then added into the wells, and incubated overnight at 4° C. After wash with PBST, HRP-conjugated anti-IgG Fc antibody (Santa Cruz, sc-2005) and TMB substrate were added, and cell binding was measured by absorbance at 450 nm. As shown in FIG. 6, TY21421 binds with high affinity to cell surface PD-L1 after fixation with paraformaldehyde, its calculated EC50 is 0.30 nM.

Example 7

Figure 7:
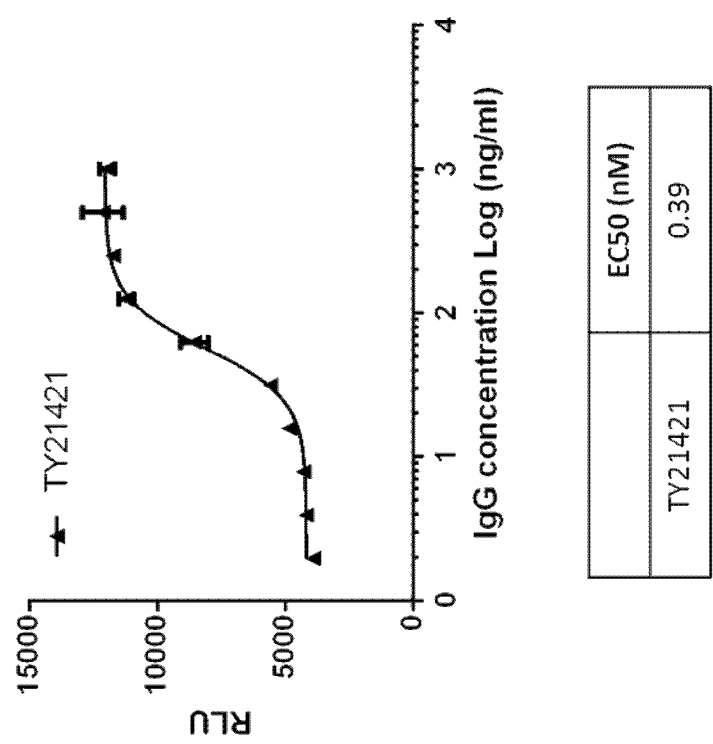
FIG. 7 shows that one exemplary antibody TY21421 is potent in Promega PD1/PD-L1 reporter gene assay.

Functional Characterization of Antibodies Using Promega PD1/PD-L1 Reporter Gene Assay The Promega PD1/PD-L1 reporter gene assay was used to examine whether the PD-L1 antibodies are functional in activating the PD-L1-dependent, NFAT mediated luciferase expression. Briefly, 40.000 PD-L1-expressing CHO cells (Promega, cat #J1081) were plated in each well of a 96 well white plate, incubated at 37° C. for 16-18 h. Then 40,000 PD-1-expressing Jurkat cells (Promega, cat #J1121) were added into each well in 2% FBS-RPMI1640. Serial dilutions of TY21421 were added into the culture, and the plate was further incubated at 37° C. for 6 h before Relative luminescence units (RLU) were measured. The antibody potency was evaluated by its calculated EC50. As shown in FIG. 7, TY21421 potently stimulates the PD-L1 dependent signaling pathway, and its calculated EC50 reaches 0.39 nM.

Example 8

Stimulation of CD4+ T Cell Activities by Anti-PD-L1 Antibodies

Figure 8:
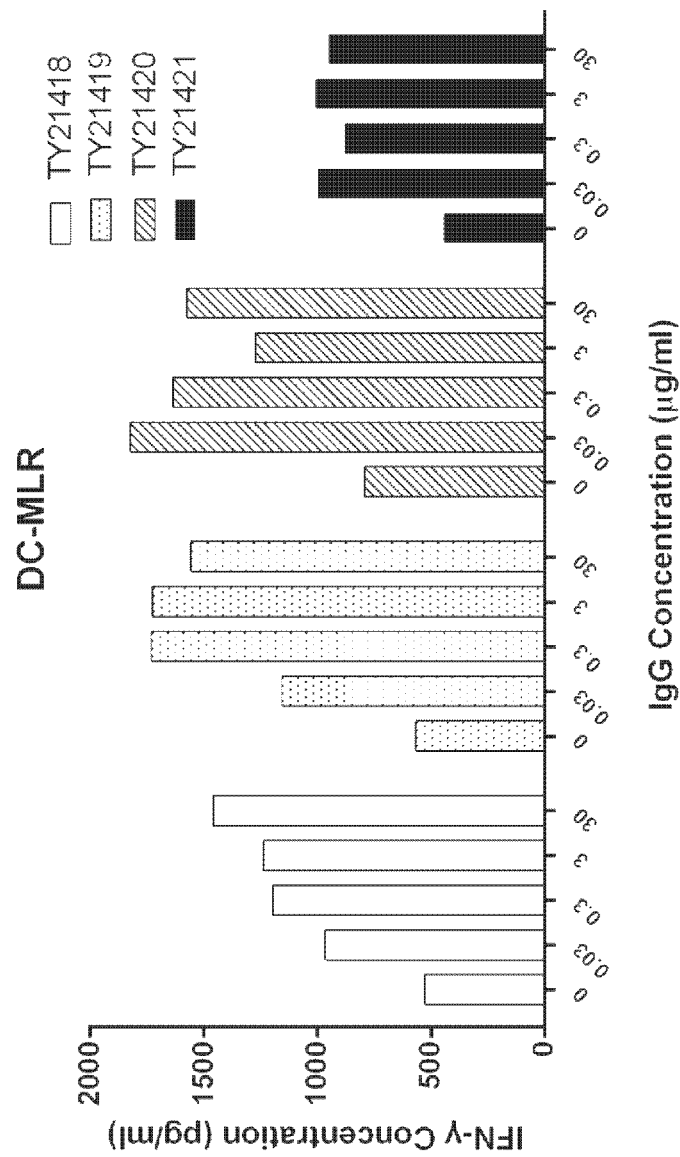
FIG. 8 shows exemplary antibodies stimulate IFN-γ release by DC-CD4+ T cells in DC-MLR assays.

PD-L1 antibodies were also tested for their ability to enhance T cell activity in DC-MLR assays. Briefly, PBMCs were isolated by density gradient centrifugation from a healthy donor and CD14+ monocytes were purified from PBMCs by positive selection commercial kit (StemCell). They were skewed into DC by in vitro culturing in RPMI 1640 medium supplemented with 10% inactivated FBS, 1% penicillin/streptomycin, 20 ng/mL rhGM-CSF and 20 ng/mL rhIL-4 for 6 days, and the culture medium was changed with fresh one on day 3. DC maturation was induced in RPMI 1640 medium supplemented with 10% inactivated FBS, 1% penicillin/streptomycin, and 50 ng/mL rhTNF-α on day 6 for 24 hours. CD4+ T cells from another healthy donor were purified by negative isolation from fresh human PBMCs, which were prepared from whole blood by centrifugation over a density gradient medium. Matured DCs (10,000) were then co-cultured with allogenic CD4+ T cells (100,000) in the presence of serial dilutions of PD-L1 antibodies. Five days later, the IFN-γ cytokine in the supernatant was measured by ELISA. As shown in FIG. 8, TY21418, TY21419 and TY21421 significantly enhanced the secretion of IFN-γ cytokine even at 0.03 μg/ml, the lowest concentration tested.

Figure 9:
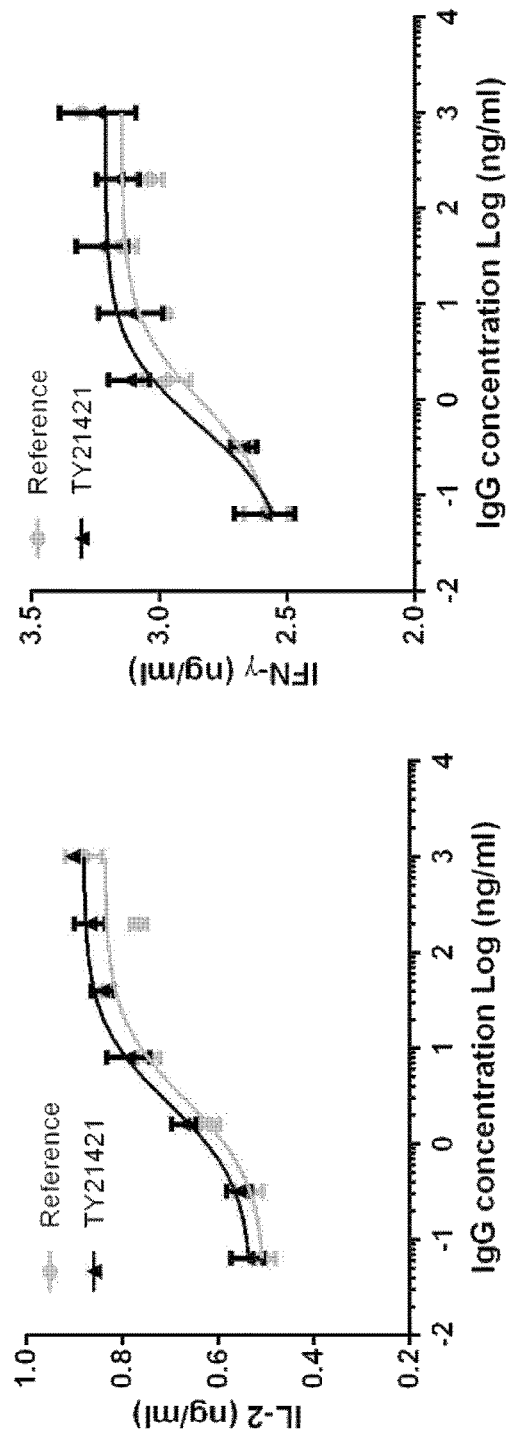
FIG. 9 shows one exemplary antibody TY21421 potently stimulates IL2 and IFN-γ release in MLR assays.

In another donor pair, and with another approach of DC maturation, i.e, using 1 mg/mL LPS (Sigma) and 50 ng/mL IFN-γ (Novoprotein) instead of 50 ng/mL rhTNF-α, TY21421 was shown to be as effective as the reference antibody in stimulating the T cell activity, exemplified by the increase of the released IL2 and IFN-γ (FIG. 9).

Example 9

Antibody Dependent Cell Mediated Cytotoxicity (ADCC) by Anti-PD-L1 Antibodies

Figure 10:
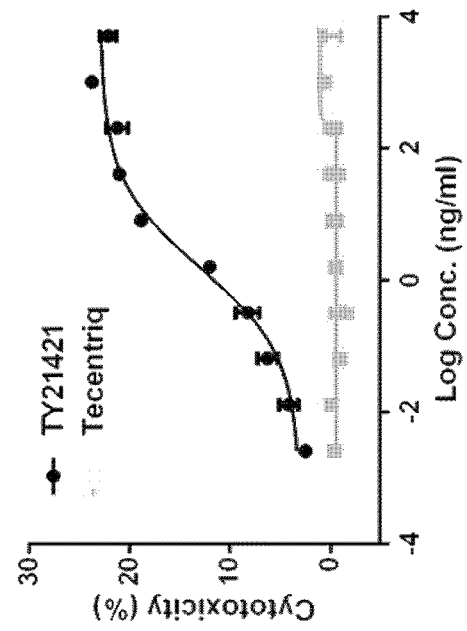
FIG. 10 shows one exemplary antibody TY21421 possesses ADCC effect, in contrast to the reference antibody Tecentriq.

The candidate antibodies were constructed in wild type IgG1 isotype. In vitro experiments were carried out to demonstrate their ADCC effect. Briefly, human peripheral blood mononuclear cells (PBMC) from a healthy donor were incubated with PD-L1-expressing HCC827 cells at a ratio of 30:1. Then serially diluted TY21421 or commercial Tecentriq (as a negative control for ADCC) were added into the culture and incubated for 4 hours. Cytotoxicity was evaluated by measuring the release of lactate dehydrogenase (LDH) from target cells by LDH cytotoxicity kit (Dojindo, cat #CK12). As evidenced in FIG. 10, TY21421 demonstrates potent ADCC effect. In contrast and consistent with earlier reports, Tecentriq shows little ADCC effect, even at high concentrations.

Example 10

Treatment of Mouse Syngeneic Models with Anti-PD-L1 Antibodies

The species cross-reactivity with mouse PD-L1 allows quick in vivo functional assessment. TY21420 and TY21421 have been tested in multiple mouse syngeneic models.

Figure 11:
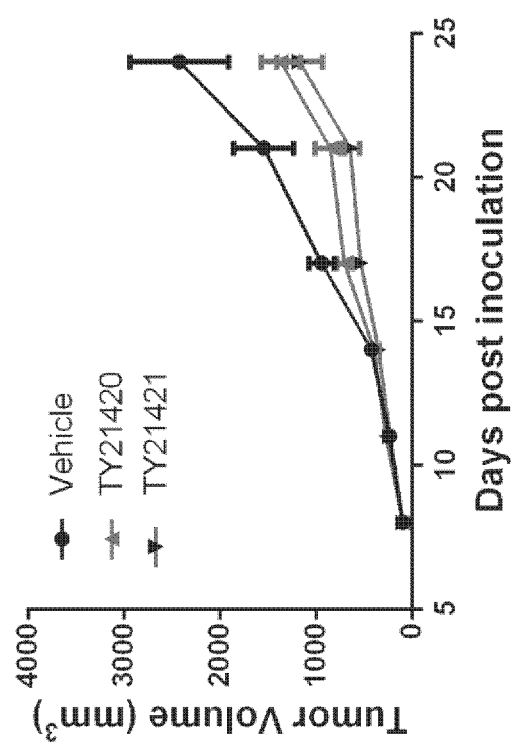
FIG. 11 shows anti-tumor efficacy of two exemplary cross-reactive antibodies in H22 mouse liver cancer model.

10a. PD-L1 Antibodies Exhibit Anti-Tumor Efficacy in H22 Mouse Liver Cancer Model BALB/c mice (n=8 per group) were transplanted subcutaneously with $2\times10^6$ H22 mouse liver cancer cells. When tumors were established (~100 mm$^3$), these tumor-bearing mice were treated with vehicle, TY21420 (10 mg/kg), or TY21421 (10 mg/kg), by intraperitoneal injection, twice a week for up to 3 weeks. Tumor growth was monitored twice a week and reported as the mean tumor volume±SEM over time. As shown in FIG. 11, both TY21420 and TY21421 were efficacious in suppressing H22 tumor growth.

Figure 12:
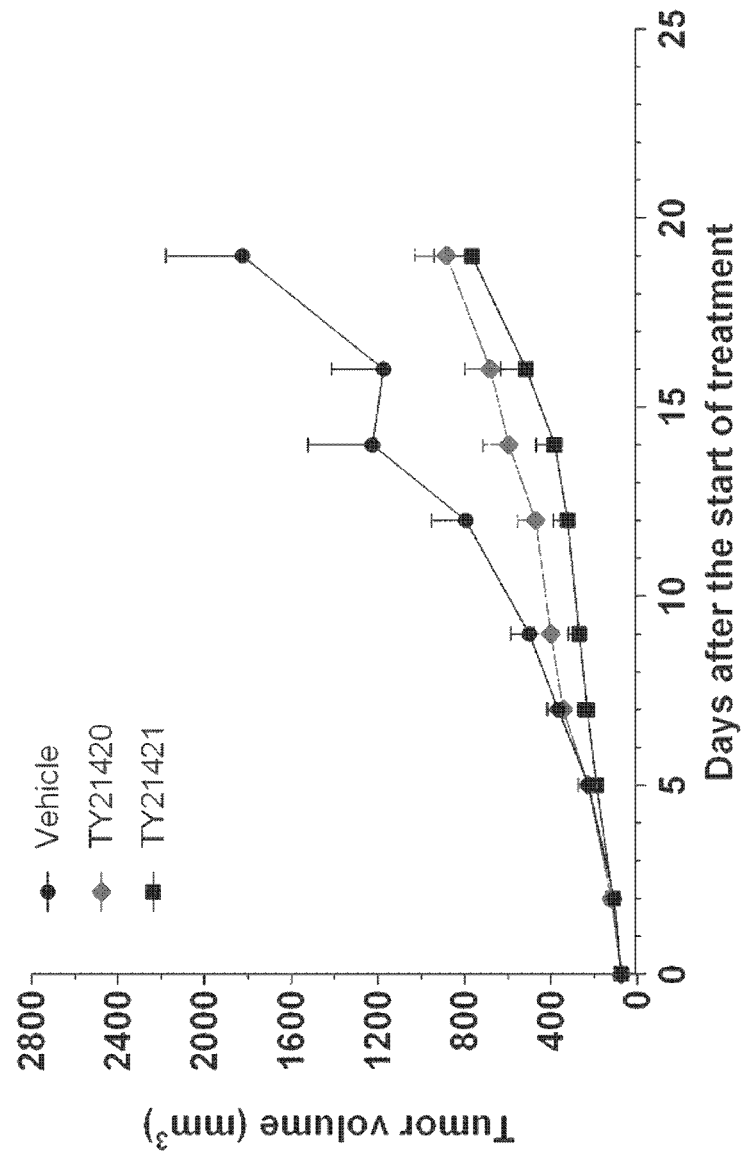
FIG. 12 shows anti-tumor efficacy of two exemplary cross-reactive antibodies in MC38 mouse colon cancer model.

10b. PD-L1 Antibodies Exhibit Anti-Tumor Efficacy in MC38 Mouse Colon Cancer Model A group of 9 Fab hits bind to PD-L1 from human, monkey and mouse, they have identical VH (SEQ ID NO: 127), but different VL. C57BL/6 mice were transplanted subcutaneously with $3\times10^5$ MC38 mouse colon cancer cells. When tumors were established (~75 mm$^3$), these tumor-bearing mice were treated with vehicle, TY21420 (10 mg/kg), or TY21421 (10 mg/kg), by intraperitoneal injection, twice a week for up to 3 weeks. Tumor growth was monitored three times weekly and reported as the mean tumor volume±SEM over time. As shown in FIG. 12, both TY21420 and TY21421 were efficacious in suppressing MC38 tumor growth.

Example 11

Enhanced Anti-Tumor Efficacy with Antibody Combinations

Figure 13:
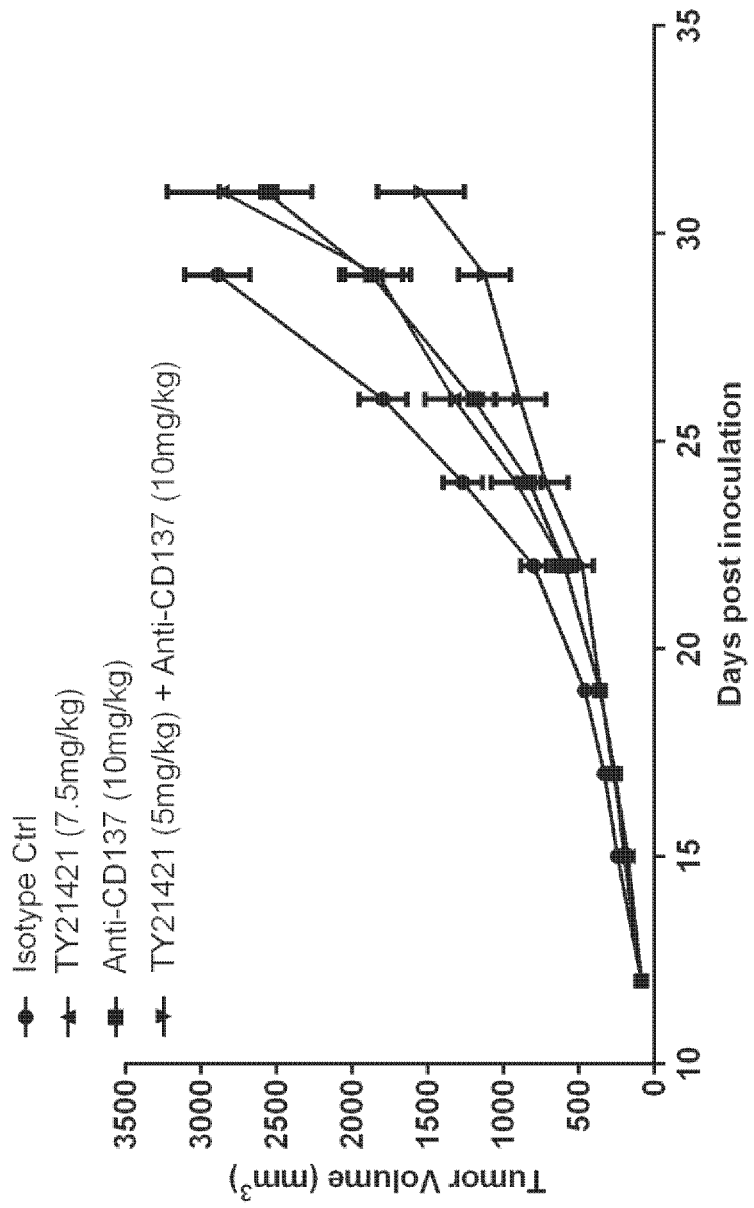
FIG. 13 shows enhanced anti-tumor efficacy with combination of TY21421 and a cross-reactive anti-CD137 antibody in LL/2 mouse lung cancer model.

11a. Enhanced Anti-Tumor Efficacy with Combination of TY21421 and a Species Cross-Reactive Anti-CD137 Antibody in LL/2 Mouse Lung Cancer Model C57BL/6 mice (n=8 per group) were transplanted subcutaneously with 2×105 LL/2 mouse lung cancer cells. When tumors were established (~87 mm3), these tumor-bearing mice were treated by intraperitoneal injection with isotype control, TY21421 (7.5 mg/kg, thrice a week×3 weeks), or anti-CD137 antibody (10 mg/kg, twice a week×3 weeks), such as those disclosed in PCT International Application No. PCT/CN2017/098332, incorporated herein by reference in its entirety, either as monotherapy or in combination. Tumor growth was monitored twice a week and reported as the mean tumor volume±SEM over time. As shown in FIG. 13, either TY21421 or anti-CD137 antibody, as a monotherapy, was efficacious in suppressing LL/2 mouse tumor growth. Interestingly, when used in combination, TY21421 and anti-CD137 antibody were even more potent in suppressing LL/2 mouse tumor growth.

Figure 14:
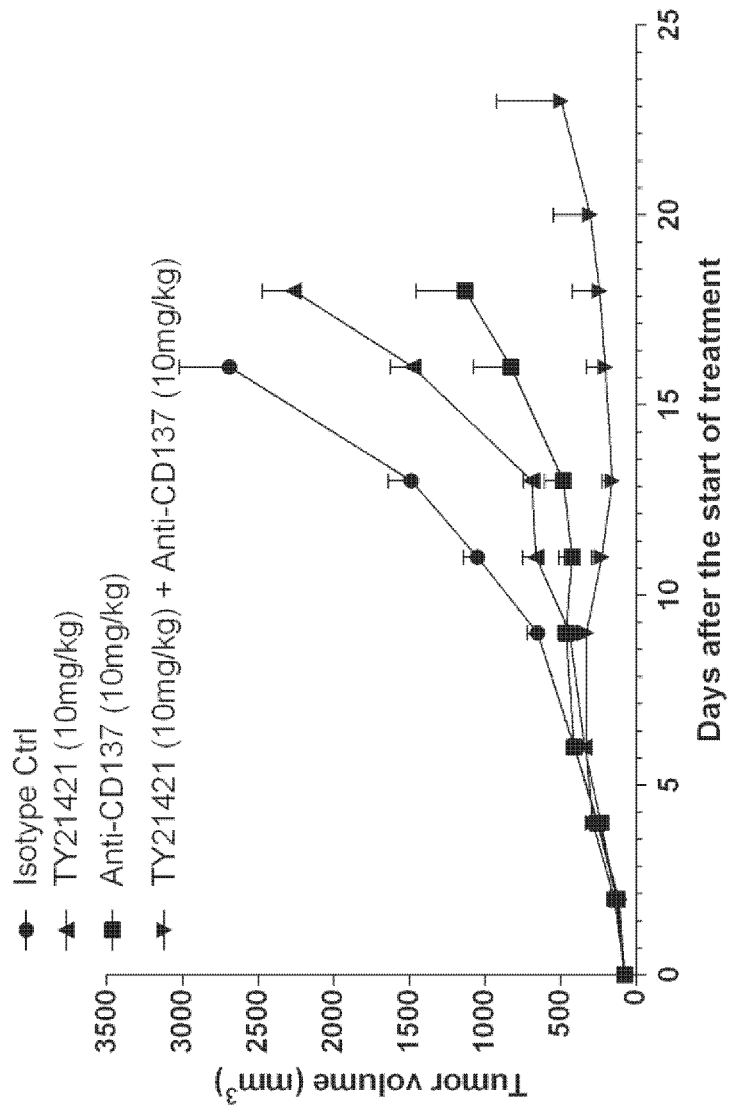
FIG. 14 shows enhanced anti-tumor efficacy with combination of TY21421 and a cross-reactive anti-CD137 antibody in 3LL mouse lung cancer model.

11b. Enhanced Anti-Tumor Efficacy with Combination of TY21421 and a Species Cross-Reactive Anti-CD137 Antibody in 3LL Mouse Lung Cancer Model C57BL/6 mice (n=8 per group) were transplanted subcutaneously with 2×106 3LL mouse lung cancer cells. When tumors were established (~76 mm3), these tumor-bearing mice were treated by intraperitoneal injection with isotype control, TY21421 (10 mg/kg, twice a week×3 weeks), or anti-CD137 antibody (10 mg/kg, twice a week×3 weeks), either as monotherapy or in combination. Tumor growth was monitored twice a week and reported as the mean tumor volume±SEM over time. As shown in FIG. 14, either TY21421 or anti-CD137 antibody, as a monotherapy, was efficacious in suppressing 3LL mouse tumor growth. Interestingly, when used in combination, TY21421 and anti-CD137 antibody were much more potent in suppressing 3LL mouse tumor growth.

Example 12

Application of an Anti-PD-L1 Antibody as a Theranostic Agent for Cancer Immunotherapy The mouse cross-reactive anti-PD-L1 antibody TY21421 was tested as a theranostic agent for cancer immunotherapy. The antibody TY21421 was conjugated with p-SCN-Bn-NOTA (Macrocyclics, Inc. Dallas, TX) in PBS buffer. On average, three molecules of p-SCN-Bn-NOTA were conjugated to each TY21421 molecule as measured by MALDI-TOF-MS. Afterwards, $^{64}$Cu—Cu$^{2+}$ (Peking University Cancer Hospital, Beijing, China) was chelated at 37° C. for 1 hr, and the chelated antibody ($^{64}$Cu-TY21421) was fractionated through size exclusion chromatography and stored in PBS (pH 7.4).

12a. PET/CT Imaging and Biodistribution of $^{64}$Cu-AG10130 in Mice with MC38 Xenografts The radiolabeled anti-PD-L1 antibody $^{64}$Cu-TY21421 (22.2±0.2 MBq) was injected into female C57BL/6 mice with MC38 xenografts, and images were recorded at 0.5 hr, 12 hr, 24 hr, 36 hr, 48 hr and 62 hr post injection using NanoScan PET-CT scanner (Mediso Medical Solutions HUN, Inc.). Images were reconstructed by the Tera-Tomo 3D method, and Variance Reduced D.W. Three-Dimensional ROIs (regions of interest) were acquired by Nucline NanoScan software (InterView™ FUSION, Mediso Medical Solutions HUN, Inc.) on the reconstructed PET images.

Figure 15:
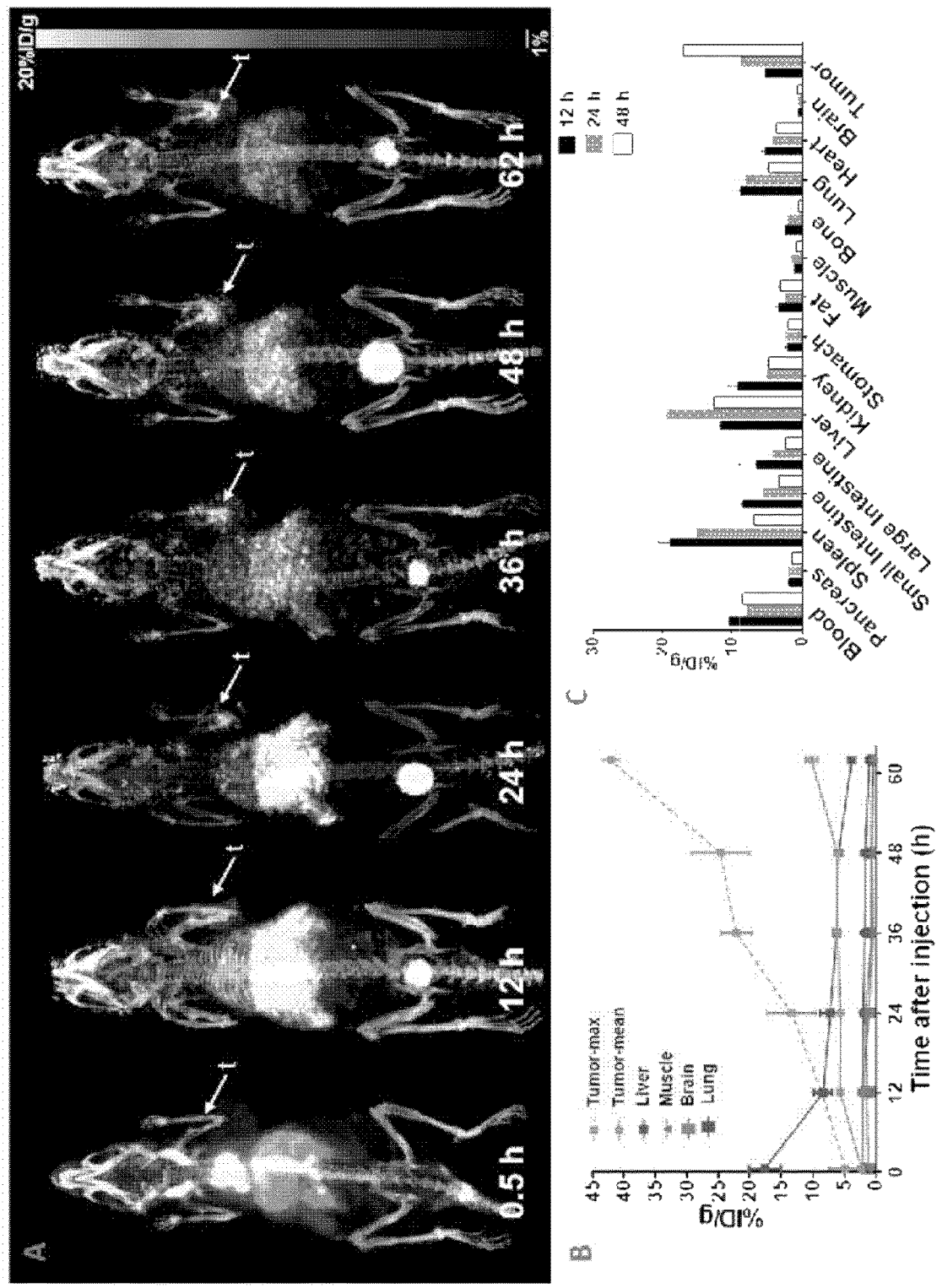
FIG. 15 shows PET/CT imaging and biodistribution analysis of $^{64}$Cu-TY21421 in mice with MC38 xenografts. (A) Representative PET/CT images of mice with MC38 xenografts at 0.5 hr, 12 hr, 24 hr, 36 hr, 48 hr and 62 hr post injection of $^{64}$Cu-TY21421. (B) The average time-course (n=4) of the uptake of $^{64}$Cu-TY21421 in mouse tumor, liver, muscle, brain and lung at 0.5 hr, 12 hr, 24 hr, 36 hr, 48 hr and 62 hr post injection. (C) The average (n=3) biodistribution and time-course of the uptake of $^{64}$Cu-TY21421 at 12 h, 24 h and 48 h post injection.

As shown in the representative PET/CT images in FIG. 15, uptake of $^{64}$Cu-TY21421 in the tumor site, as measured by ROI, gradually increased from 2.3±1.2% ID/g at 0.5 hr to 10.2±1.7% ID/g at 62 hr post injection (FIG. 15, panel B). In contrast, during the same period, uptake of $^{64}$Cu-TY21421 in liver and muscle gradually decreased (FIG. 15, panel B). Therefore, the ROI ratios of tumor/liver and tumor/muscle steadily increased to 62.1±23.3 and 3.18±1.06 respectively at 62 hr post injection.

Next, ex vivo biodistribution studies of $^{64}$Cu-TY21421 were carried out at 12 hr, 24 hr and 48 hr post injection. MC38 tumor-bearing female C57BL/6 mice (n=3 for each time point) were injected intravenously with $^{64}$Cu-TY21421 that, when corrected by its decay, the injection dose for each mouse was 0.56 MBq at 12 hr, 24 hr and 48 hr post injection. The tumors and multiple mouse organs were dissected and weighed, and the radioactivity was measured by gamma counter. As shown in FIG. 15, panel C and Table 7, the uptakes of $^{64}$Cu-TY21421 in the tumor, liver, muscle and bone were consistent with PET/CT imaging, i.e., uptake in the tumor increased in a time dependent manner, and became higher than liver and other major organs 48 hrs post injection.

TABLE 7

Average biodistribution of $^{64}$Cu-TY21421 in C57BL/6 Mice bearing MC38 tumors (n = 4).

| Organ | 12 h | 24 h | 48 h |
| --- | --- | --- | --- |
| Blood | 10.35 ± 2.96 | 7.64 ± 0.78 | 8.19 ± 2.53 |
| Pancreas | 11.72 ± 0.27 | 1.85 ± 0.13 | 1.12 ± 0.26 |
| Spleen | 18.82 ± 1.83 | 15.11 ± 0.55 | 6.37 ± 0.48 |
| Small Intestine | 8.44 ± 0.25 | 5.43 ± 0.21 | 3.04 ± 0.24 |
| Large Intestine | 6.50 ± 2.46 | 4.12 ± 0.76 | 2.00 ± 0.10 |
| Liver | 11.61 ± 0.64 | 19.33 ± 2.24 | 12.35 ± 1.27 |
| Kidney | 9.02 ± 1.54 | 4.76 ± 2.24 | 4.39 ± 1.13 |
| Stomach | 2.03 ± 0.31 | 2.18 ± 0.26 | 1.52 ± 0.14 |
| Fat | 3.23 ± 0.51 | 2.15 ± 0.67 | 2.85 ± 0.94 |
| Muscle | 1.09 ± 0.15 | 1.31 ± 0.23 | 0.64 ± 0.16 |
| Bone | 2.32 ± 0.49 | 1.95 ± 0.06 | 0.24 ± 1.32 |
| Lung | 8.73 ± 1.67 | 7.86 ± 1.87 | 4.44 ± 0.66 |
| Heart | 5.19 ± 0.52 | 4.19 ± 0.55 | 3.43 ± 0.60 |
| Brain | 0.48 ± 0.11 | 0.39 ± 0.00 | 0.48 ± 0.13 |
| Tail | 9.61 ± 1.29 | 8.35 ± 2.52 | 2.56 ± 0.46 |
| Tumor | 5.16 ± 0.17 | 8.19 ± 0.18 | 15.06 ± 4.52 |

12b. Comparison Between the Traditional PET Probe $^{18}$F-FDG and the PD-L1 Specific PET Probe $^{64}$Cu-TY21421

Figure 16:
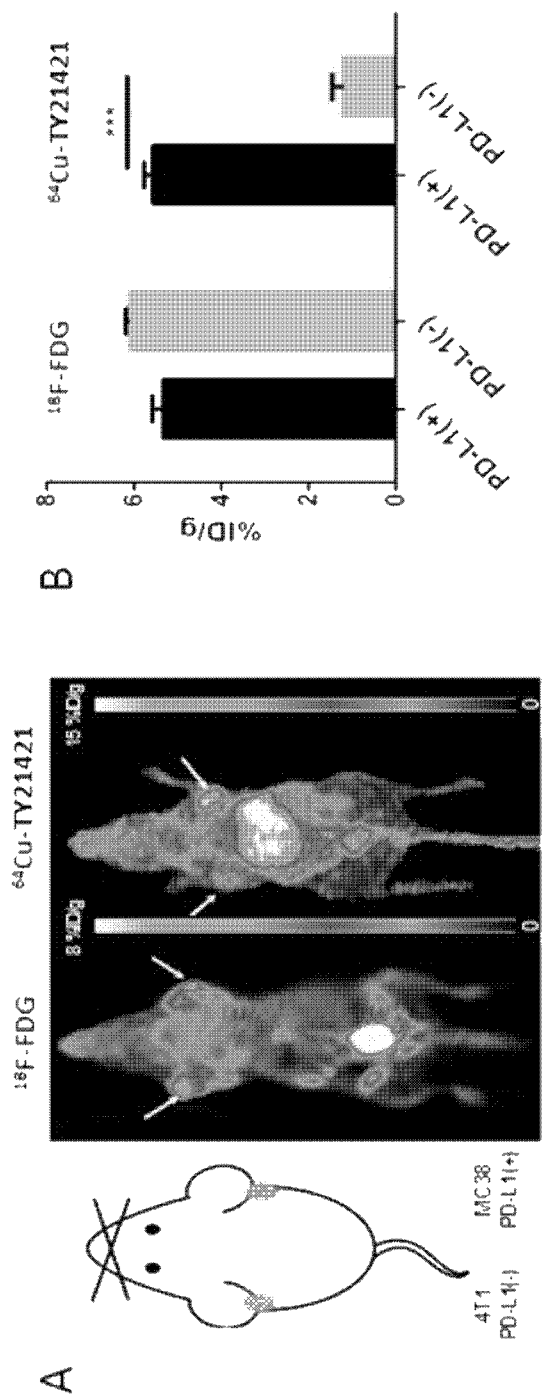
FIG. 16 shows the comparison between the traditional PET probe $^{18}$F-FDG and the PD-L1 specific PET probe $^{64}$Cu-TY21421 in assessing PD-L1 expression level in different tumors. (A) Representative PET images of $^{18}$F-FDG and $^{64}$Cu-TY21421 in mice bearing MC38 and 4T1 xenografts. (B) The average (n=4) uptake of $^{18}$F-FDG and $^{64}$Cu-TY21421 in MC38 and 4T1 tumors in NU/NU mice.

To compare and contrast between the traditional PET probe $^{18}$F-FDG and the PD-L1 specific PET probe $^{64}$Cu-TY21421, mice bearing MC38 and 4T1 xenografts were injected with $^{18}$F-FDG (7.4 MBq), and images were recorded 1 hr later. Afterwards, $^{64}$Cu-TY21421 (7.4 MBq) was injected, and images were recorded 12 hr later. As shown in FIG. 16, no significant differences of $^{18}$F-FDG uptake in the MC38 and 4T1 tumor sites were observed: $^{18}$F-FDG uptake was 5.3±0.4% ID/g for MC38 xenograft and 6.4±0.6% ID/g for 4T1 xenografts (FIG. 16, panel B). In contrast, $^{64}$Cu-TY21421 was much more specific: the $^{64}$Cu-TY21421 uptake was 5.6±0.3% ID/g for PD-L1 expressing MC38 tumor, and 1.3±0.4% ID/g for 4T1 tumor that does not express PD-L1, more than four fold difference (FIG. 16, panel B). The presence of PD-L1 in MC38 tumor and its absence in 4T1 tumor were confirmed with IHC experiments using an IHC-specific anti-PD-L1 antibody (#64988, Cell Signaling Technology).

12c. PET Imaging of $^{64}$Cu-TY21421 in Human Cancer Model

Figure 17:
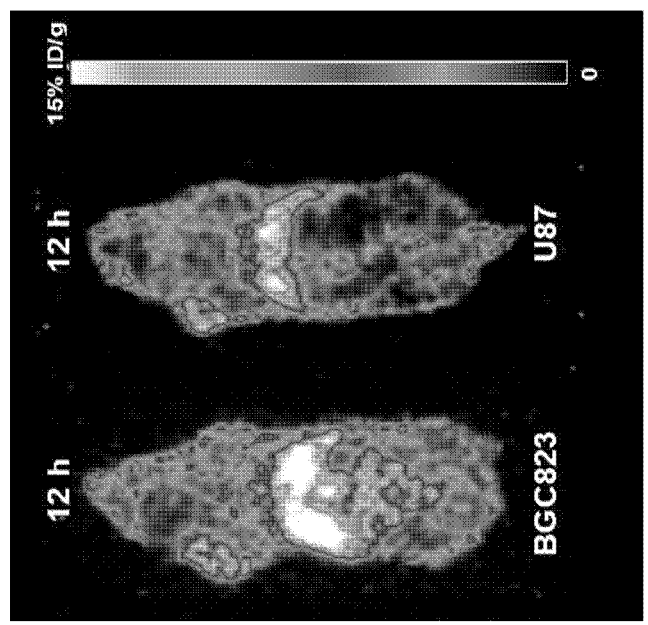
FIG. 17 shows micro-PET imaging of $^{64}$Cu-TY21421 in Nu/Nu mice bearing BGC823 and U87MG tumor xenografts 12 hr post injection.F

The radiolabeled anti-PD-L1 antibody $^{64}$Cu-TY21421 was also used to assess PD-L1 expression level in human cancer xenografts. Nu/Nu mice were inoculated with human gastric cancer (BGC823, National Infrastructure of Cell Line Resources, China) and human glioblastoma (U87MG, National Infrastructure of Cell Line Resources, China) xenografts, both were reported to have PD-L1 expression. $^{64}$Cu- TY21421 exhibited specific accumulation in both BGC823 and U87MG xenografts (FIG. 17). The uptake of $^{64}$Cu-TY21421 was 4.6±0.5% Dig in BGC823 (n=3) and 5.3±0.4% Dig in U87MG (n=3) at 12 hrs post injection.

EQUIVALENTS

The present disclosure provides among other things novel anti-PD-L1 antibodies and use thereof. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and sequence database entries mentioned herein are hereby incorporated by reference in their entirety as if each individual publication or patent was specifically and individually indicated to be incorporated by reference.

The invention claimed is:

1. An isolated antibody, or antigen-binding fragment thereof, that selectively binds to human PD-L1, comprising
(a) an HVR_L1 having the amino acid sequence of SEQ ID NO: 100, an HVR_L2 having the amino acid sequence of SEQ ID NO: 109, and an HVR_L3 having the amino acid sequence of SEQ ID NO: 118, and further comprising an HVR_H1 having the amino acid sequence of SEQ ID NO: 167, an HVR_H2 having the amino acid sequence of SEQ ID NO: 168, and an HVR_H3 having the amino acid sequence of SEQ ID NO: 169;

or (b) an HVR_L1 having the amino acid sequence of SEQ ID NO: 97, an HVR_L2 having the amino acid sequence of SEQ ID NO: 106, and an HVR_L3 having the amino acid sequence of SEQ ID NO: 115, and further comprising an HVR_H1 having the amino acid sequence of SEQ ID NO: 167, an HVR_H2 having the amino acid sequence of SEQ ID NO: 168, and an HVR_H3 having the amino acid sequence of SEQ ID NO: 169.

2. The antibody or fragment thereof of claim 1, further comprising:
(a) a VL having the amino acid sequence of SEQ ID NO: 158 and further comprising a VH having the amino acid sequence of SEQ ID NO: 127;
or
(b) a VL having the amino acid sequence of SEQ ID NO: 155 and further comprising a VH having the amino acid sequence of SEQ ID NO: 127.

3. The antibody or fragment thereof of claim 1, wherein the antibody or fragment thereof is cross-reactive with monkey and mouse PD-L1.

4. The antibody or fragment thereof of claim 1, wherein the antibody or fragment thereof binds human PD-L1 with a KD of 100 nM or less, as measured by surface plasmon resonance.

5. The antibody or fragment thereof of claim 1, wherein the antibody or fragment thereof binds human PD-L1 with a KD of 50 nm or less, as measured by surface plasmon resonance.

6. The antibody or fragment thereof of claim 1, wherein the antibody or fragment thereof binds human PD-L1 with a KD of 10 nM or less, as measured by surface plasmon resonance.

7. The antibody or fragment thereof of claim 1, further comprising a human IgG1 or IgG4 heavy chain constant region Fc, or a variant thereof.

8. A pharmaceutical composition comprising the antibody or fragment thereof of claim 1 and a pharmaceutically acceptable carrier.

9. A theranostic composition comprising the antibody or fragment thereof of claim 1 and a diagnostic imaging agent, wherein preferably the diagnostic imaging agent is a radionuclide label.

10. A method for diagnosing and treating a cancer in a subject in need thereof, comprising administering an effective amount of the theranostic composition of claim 9 to said subject.

11. A method of detecting PD-L1 in vitro, comprising fixing a cell with paraformaldehyde, and immunostaining the cell with the antibody or fragment thereof of claim 1.

* * * * *

SEQUENCE LISTING

```
<160> NUMBER OF SEQ ID NOS: 182

<210> SEQ ID NO 1
<211> LENGTH: 11
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (5)..(5)
<223> OTHER INFORMATION: Xaa = G or S
<220> FEATURE:
<221> NAME/KEY: VARIANT
<222> LOCATION: (6)..(6)
<223> OTHER INFORMATION: Xaa = I or V
<220> FEATURE:
<221> NAME/KEY: VARIANT
<222> LOCATION: (7)..(7)
<223> OTHER INFORMATION: Xaa = E, G or S
<220> FEATURE:
<221> NAME/KEY: VARIANT
<222> LOCATION: (8)..(8)
<223> OTHER INFORMATION: Xaa = K, P or S
<220> FEATURE:
<221> NAME/KEY: VARIANT
<222> LOCATION: (9)..(9)
<223> OTHER INFORMATION: Xaa = F, W or Y

<400> SEQUENCE: 1

Arg Ala Ser Gln Xaa Xaa Xaa Xaa Xaa Leu Ala
1               5                   10

<210> SEQ ID NO 2
<211> LENGTH: 15
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (4)..(4)
<223> OTHER INFORMATION: Xaa = E or Q
<220> FEATURE:
<221> NAME/KEY: VARIANT
<222> LOCATION: (9)..(9)
<223> OTHER INFORMATION: Xaa = F, H or Y
<220> FEATURE:
<221> NAME/KEY: VARIANT
<222> LOCATION: (11)..(11)
<223> OTHER INFORMATION: Xaa = I or K
<220> FEATURE:
<221> NAME/KEY: VARIANT
<222> LOCATION: (15)..(15)
<223> OTHER INFORMATION: Xaa = A or D

<400> SEQUENCE: 2

Arg Ala Ser Xaa Ser Val Asp Phe Xaa Gly Xaa Ser Phe Leu Xaa
1               5                   10                  15
```

```
<210> SEQ ID NO 3
<211> LENGTH: 11
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Q or R
<220> FEATURE:
<221> NAME/KEY: VARIANT
<222> LOCATION: (5)..(5)
<223> OTHER INFORMATION: Xaa = D, S or T
<220> FEATURE:
<221> NAME/KEY: VARIANT
<222> LOCATION: (8)..(8)
<223> OTHER INFORMATION: Xaa = K, S or T
<220> FEATURE:
<221> NAME/KEY: VARIANT
<222> LOCATION: (11)..(11)
<223> OTHER INFORMATION: Xaa = A or N

<400> SEQUENCE: 3

Xaa Ala Ser Gln Xaa Ile Pro Xaa Phe Leu Xaa
1               5                   10

<210> SEQ ID NO 4
<211> LENGTH: 11
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (6)..(6)
<223> OTHER INFORMATION: Xaa = I or V
<220> FEATURE:
<221> NAME/KEY: VARIANT
<222> LOCATION: (8)..(8)
<223> OTHER INFORMATION: Xaa = P or S
<220> FEATURE:
<221> NAME/KEY: VARIANT
<222> LOCATION: (9)..(9)
<223> OTHER INFORMATION: Xaa = W or Y

<400> SEQUENCE: 4

Arg Ala Ser Gln Gly Xaa Ser Xaa Xaa Leu Ala
1               5                   10

<210> SEQ ID NO 5
<211> LENGTH: 11
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (5)..(5)
<223> OTHER INFORMATION: Xaa = S or T

<400> SEQUENCE: 5

Arg Ala Ser Gln Xaa Ile Pro Ser Phe Leu Asn
1               5                   10

<210> SEQ ID NO 6
<211> LENGTH: 9
<212> TYPE: PRT
<213> ORGANISM: Artificial
<220> FEATURE:
<223> OTHER INFORMATION: Synthetic Construct
```

```
<220> FEATURE:
<221> NAME/KEY: VARIANT
<222> LOCATION: (4)..(4)
<223> OTHER INFORMATION: Xaa = N or S
<220> FEATURE:
<221> NAME/KEY: VARIANT
<222> LOCATION: (5)..(5)
<223> OTHER INFORMATION: Xaa = L or R
<220> FEATURE:
<221> NAME/KEY: VARIANT
<222> LOCATION: (6)..(6)
<223> OTHER INFORMATION: Xaa = A or E
<220> FEATURE:
<221> NAME/KEY: VARIANT
<222> LOCATION: (7)..(7)
<223> OTHER INFORMATION: Xaa = S or T
<220> FEATURE:
<221> NAME/KEY: VARIANT
<222> LOCATION: (9)..(9)
<223> OTHER INFORMATION: Xaa = I or V

<400> SEQUENCE: 6

Asp Ala Ser Xaa Xaa Xaa Xaa Gly Xaa
1               5

<210> SEQ ID NO 7
<211> LENGTH: 9
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (4)..(4)
<223> OTHER INFORMATION: Xaa = S or T

<400> SEQUENCE: 7

Ala Ala Ser Xaa Leu Gln Ser Gly Val
1               5

<210> SEQ ID NO 8
<211> LENGTH: 9
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (5)..(5)
<223> OTHER INFORMATION: Xaa = L or R
<220> FEATURE:
<221> NAME/KEY: VARIANT
<222> LOCATION: (6)..(6)
<223> OTHER INFORMATION: Xaa = A or E
<220> FEATURE:
<221> NAME/KEY: VARIANT
<222> LOCATION: (9)..(9)
<223> OTHER INFORMATION: Xaa = I or V

<400> SEQUENCE: 8

Asp Ala Ser Asn Xaa Xaa Thr Gly Xaa
1               5

<210> SEQ ID NO 9
<211> LENGTH: 11
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (7)..(7)
<223> OTHER INFORMATION: Xaa = A, H, S or Y
```

```
<400> SEQUENCE: 9

Tyr Cys Gln Gln Tyr Asp Xaa Trp Pro Tyr Thr
1               5                   10

<210> SEQ ID NO 10
<211> LENGTH: 13
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (4)..(4)
<223> OTHER INFORMATION: Xaa = H or Q
<220> FEATURE:
<221> NAME/KEY: VARIANT
<222> LOCATION: (6)..(6)
<223> OTHER INFORMATION: Xaa = G, I, S, T or V
<220> FEATURE:
<221> NAME/KEY: VARIANT
<222> LOCATION: (11)..(11)
<223> OTHER INFORMATION: Xaa = G, L, Q, R or V

<400> SEQUENCE: 10

Tyr Cys Gln Xaa Tyr Xaa Ser Trp Pro Arg Xaa Phe Thr
1               5                   10

<210> SEQ ID NO 11
<211> LENGTH: 11
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (7)..(7)
<223> OTHER INFORMATION: Xaa = A or S

<400> SEQUENCE: 11

Tyr Cys Gln Gln Tyr Asp Xaa Trp Pro Tyr Thr
1               5                   10

<210> SEQ ID NO 12
<211> LENGTH: 13
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (6)..(6)
<223> OTHER INFORMATION: Xaa = I or T

<400> SEQUENCE: 12

Tyr Cys Gln His Tyr Xaa Ser Trp Pro Arg Gln Phe Thr
1               5                   10

<210> SEQ ID NO 13
<211> LENGTH: 11
<212> TYPE: PRT
<213> ORGANISM: Artificial
<220> FEATURE:
<223> OTHER INFORMATION: Synthetic Construct

<400> SEQUENCE: 13

Arg Ala Ser Gln Gly Ile Gly Ser Phe Leu Ala
1               5                   10
```

```
<210> SEQ ID NO 14
<211> LENGTH: 15
<212> TYPE: PRT
<213> ORGANISM: Artificial
<220> FEATURE:
<223> OTHER INFORMATION: Synthetic Construct

<400> SEQUENCE: 14

Arg Ala Ser Glu Ser Val Asp Phe Tyr Gly Lys Ser Phe Leu Asp
1               5                   10                  15

<210> SEQ ID NO 15
<211> LENGTH: 15
<212> TYPE: PRT
<213> ORGANISM: Artificial
<220> FEATURE:
<223> OTHER INFORMATION: Synthetic Construct

<400> SEQUENCE: 15

Arg Ala Ser Gln Ser Val Asp Phe Tyr Gly Lys Ser Phe Leu Ala
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthetic Construct

<400> SEQUENCE: 16

Arg Ala Ser Glu Ser Val Asp Phe Phe Gly Lys Ser Phe Leu Ala
1               5                   10                  15

<210> SEQ ID NO 17
<211> LENGTH: 15
<212> TYPE: PRT
<213> ORGANISM: Artificial
<220> FEATURE:
<223> OTHER INFORMATION: Synthetic Construct

<400> SEQUENCE: 17

Arg Ala Ser Gln Ser Val Asp Phe Tyr Gly Lys Ser Phe Leu Asp
1               5                   10                  15

<210> SEQ ID NO 18
<211> LENGTH: 11
<212> TYPE: PRT
<213> ORGANISM: Artificial
<220> FEATURE:
<223> OTHER INFORMATION: Synthetic Construct

<400> SEQUENCE: 18

Arg Ala Ser Gln Ser Val Ser Ser Trp Leu Ala
1               5                   10

<210> SEQ ID NO 19
<211> LENGTH: 15
<212> TYPE: PRT
<213> ORGANISM: Artificial
<220> FEATURE:
<223> OTHER INFORMATION: Synthetic Construct

<400> SEQUENCE: 19

Arg Ala Ser Glu Ser Val Asp Phe Phe Gly Lys Ser Phe Leu Ala
1               5                   10                  15

<210> SEQ ID NO 20
```

```
<211> LENGTH: 15
<212> TYPE: PRT
<213> ORGANISM: Artificial
<220> FEATURE:
<223> OTHER INFORMATION: Synthetic Construct

<400> SEQUENCE: 20

Arg Ala Ser Glu Ser Val Asp Phe His Gly Ile Ser Phe Leu Ala
1               5                   10                  15

<210> SEQ ID NO 21
<211> LENGTH: 11
<212> TYPE: PRT
<213> ORGANISM: Artificial
<220> FEATURE:
<223> OTHER INFORMATION: Synthetic Construct

<400> SEQUENCE: 21

Arg Ala Ser Gln Ser Val Ser Pro Tyr Leu Ala
1               5                   10

<210> SEQ ID NO 22
<211> LENGTH: 12
<212> TYPE: PRT
<213> ORGANISM: Artificial
<220> FEATURE:
<223> OTHER INFORMATION: Synthetic Construct

<400> SEQUENCE: 22

Arg Ala Ser Gln Ser Val Gly Ser Ile Tyr Leu Gly
1               5                   10

<210> SEQ ID NO 23
<211> LENGTH: 15
<212> TYPE: PRT
<213> ORGANISM: Artificial
<220> FEATURE:
<223> OTHER INFORMATION: Synthetic Construct

<400> SEQUENCE: 23

Arg Ala Ser Gln Ser Val Asp Phe Tyr Gly Lys Ser Phe Leu Ala
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthetic Construct

<400> SEQUENCE: 24

Arg Ala Ser Glu Ser Val Asp Phe Tyr Gly Lys Ser Phe Leu Ala
1               5                   10                  15

<210> SEQ ID NO 25
<211> LENGTH: 15
<212> TYPE: PRT
<213> ORGANISM: Artificial
<220> FEATURE:
<223> OTHER INFORMATION: Synthetic Construct

<400> SEQUENCE: 25

Arg Ala Ser Gln Ser Val Asp Phe Tyr Gly Lys Ser Phe Leu Asp
1               5                   10                  15

<210> SEQ ID NO 26
<211> LENGTH: 15
```

```
<212> TYPE: PRT
<213> ORGANISM: Artificial
<220> FEATURE:
<223> OTHER INFORMATION: Synthetic Construct

<400> SEQUENCE: 26

Arg Ala Ser Glu Ser Val Asp Phe Tyr Gly Lys Ser Phe Leu Asp
1               5                   10                  15

<210> SEQ ID NO 27
<211> LENGTH: 15
<212> TYPE: PRT
<213> ORGANISM: Artificial
<220> FEATURE:
<223> OTHER INFORMATION: Synthetic Construct

<400> SEQUENCE: 27

Arg Ala Ser Glu Ser Val Asp Phe His Gly Lys Ser Phe Leu Ala
1               5                   10                  15

<210> SEQ ID NO 28
<211> LENGTH: 11
<212> TYPE: PRT
<213> ORGANISM: Artificial
<220> FEATURE:
<223> OTHER INFORMATION: Synthetic Construct

<400> SEQUENCE: 28

Arg Ala Ser Gln Gly Val Ser Pro Trp Leu Ala
1               5                   10

<210> SEQ ID NO 29
<211> LENGTH: 11
<212> TYPE: PRT
<213> ORGANISM: Artificial
<220> FEATURE:
<223> OTHER INFORMATION: Synthetic Construct

<400> SEQUENCE: 29

Arg Ala Ser Gln Ser Val Ser Pro Tyr Leu Ala
1               5                   10

<210> SEQ ID NO 30
<211> LENGTH: 15
<212> TYPE: PRT
<213> ORGANISM: Artificial
<220> FEATURE:
<223> OTHER INFORMATION: Synthetic Construct

<400> SEQUENCE: 30

Arg Ala Ser Gln Ser Val Asp Phe His Gly Lys Ser Phe Leu Asp
1               5                   10                  15

<210> SEQ ID NO 31
<211> LENGTH: 15
<212> TYPE: PRT
<213> ORGANISM: Artificial
<220> FEATURE:
<223> OTHER INFORMATION: Synthetic Construct

<400> SEQUENCE: 31

Arg Ala Ser Gln Ser Val Asp Phe Tyr Gly Lys Ser Phe Leu Ala
1               5                   10                  15

<210> SEQ ID NO 32
<211> LENGTH: 15
<212> TYPE: PRT
```

```
<213> ORGANISM: Artificial
<220> FEATURE:
<223> OTHER INFORMATION: Synthetic Construct

<400> SEQUENCE: 32

Arg Ala Ser Glu Ser Val Asp Phe Tyr Gly Lys Ser Phe Leu Ala
1               5                   10                  15

<210> SEQ ID NO 33
<211> LENGTH: 11
<212> TYPE: PRT
<213> ORGANISM: Artificial
<220> FEATURE:
<223> OTHER INFORMATION: Synthetic Construct

<400> SEQUENCE: 33

Arg Ala Ser Gln Ser Ile Glu Lys Trp Leu Ala
1               5                   10

<210> SEQ ID NO 34
<211> LENGTH: 15
<212> TYPE: PRT
<213> ORGANISM: Artificial
<220> FEATURE:
<223> OTHER INFORMATION: Synthetic Construct

<400> SEQUENCE: 34

Arg Ala Ser Gln Ser Val Asp Phe His Gly Ile Ser Phe Leu Asp
1               5                   10                  15

<210> SEQ ID NO 35
<211> LENGTH: 15
<212> TYPE: PRT
<213> ORGANISM: Artificial
<220> FEATURE:
<223> OTHER INFORMATION: Synthetic Construct

<400> SEQUENCE: 35

Arg Ala Ser Gln Ser Val Asp Phe Tyr Gly Lys Ser Phe Leu Asp
1               5                   10                  15

<210> SEQ ID NO 36
<211> LENGTH: 15
<212> TYPE: PRT
<213> ORGANISM: Artificial
<220> FEATURE:
<223> OTHER INFORMATION: Synthetic Construct

<400> SEQUENCE: 36

Arg Ala Ser Gln Ser Val Asp Phe His Gly Ile Ser Phe Leu Asp
1               5                   10                  15

<210> SEQ ID NO 37
<211> LENGTH: 11
<212> TYPE: PRT
<213> ORGANISM: Artificial
<220> FEATURE:
<223> OTHER INFORMATION: Synthetic Construct

<400> SEQUENCE: 37

Arg Ala Ser Gln Gly Val Ser Ser Tyr Leu Ala
1               5                   10

<210> SEQ ID NO 38
<211> LENGTH: 11
<212> TYPE: PRT
<213> ORGANISM: Artificial
```

```
<220> FEATURE:
<223> OTHER INFORMATION: Synthetic Construct

<400> SEQUENCE: 38

Arg Ala Ser Gln Gly Ile Ser Pro Trp Leu Ala
1               5                   10

<210> SEQ ID NO 39
<211> LENGTH: 11
<212> TYPE: PRT
<213> ORGANISM: Artificial
<220> FEATURE:
<223> OTHER INFORMATION: Synthetic Construct

<400> SEQUENCE: 39

Arg Ala Ser Gln Ser Val Ser Ser Tyr Leu Ala
1               5                   10

<210> SEQ ID NO 40
<211> LENGTH: 9
<212> TYPE: PRT
<213> ORGANISM: Artificial
<220> FEATURE:
<223> OTHER INFORMATION: Synthetic Construct

<400> SEQUENCE: 40

Asp Ala Ser Ser Leu Glu Ser Gly Val
1               5

<210> SEQ ID NO 41
<211> LENGTH: 9
<212> TYPE: PRT
<213> ORGANISM: Artificial
<220> FEATURE:
<223> OTHER INFORMATION: Synthetic Construct

<400> SEQUENCE: 41

Asp Ala Ser Asn Arg Ala Thr Gly Ile
1               5

<210> SEQ ID NO 42
<211> LENGTH: 9
<212> TYPE: PRT
<213> ORGANISM: Artificial
<220> FEATURE:
<223> OTHER INFORMATION: Synthetic Construct

<400> SEQUENCE: 42

Asp Ala Ser Ser Leu Glu Ser Gly Val
1               5

<210> SEQ ID NO 43
<211> LENGTH: 9
<212> TYPE: PRT
<213> ORGANISM: Artificial
<220> FEATURE:
<223> OTHER INFORMATION: Synthetic Construct

<400> SEQUENCE: 43

Asp Ala Ser Ser Leu Glu Ser Gly Val
1               5

<210> SEQ ID NO 44
<211> LENGTH: 9
<212> TYPE: PRT
<213> ORGANISM: Artificial
<220> FEATURE:
```

```
<223> OTHER INFORMATION: Synthetic Construct

<400> SEQUENCE: 44

Asp Ala Ser Asn Arg Ala Thr Gly Ile
1               5

<210> SEQ ID NO 45
<211> LENGTH: 9
<212> TYPE: PRT
<213> ORGANISM: Artificial
<220> FEATURE:
<223> OTHER INFORMATION: Synthetic Construct

<400> SEQUENCE: 45

Asp Ala Ser Ser Leu Glu Ser Gly Val
1               5

<210> SEQ ID NO 46
<211> LENGTH: 9
<212> TYPE: PRT
<213> ORGANISM: Artificial
<220> FEATURE:
<223> OTHER INFORMATION: Synthetic Construct

<400> SEQUENCE: 46

Asp Ala Ser Asn Leu Glu Thr Gly Val
1               5

<210> SEQ ID NO 47
<211> LENGTH: 9
<212> TYPE: PRT
<213> ORGANISM: Artificial
<220> FEATURE:
<223> OTHER INFORMATION: Synthetic Construct

<400> SEQUENCE: 47

Asp Ala Ser Asn Arg Ala Thr Gly Ile
1               5

<210> SEQ ID NO 48
<211> LENGTH: 9
<212> TYPE: PRT
<213> ORGANISM: Artificial
<220> FEATURE:
<223> OTHER INFORMATION: Synthetic Construct

<400> SEQUENCE: 48

Asp Ala Ser Asn Leu Glu Thr Gly Val
1               5

<210> SEQ ID NO 49
<211> LENGTH: 9
<212> TYPE: PRT
<213> ORGANISM: Artificial
<220> FEATURE:
<223> OTHER INFORMATION: Synthetic Construct

<400> SEQUENCE: 49

Asp Ala Ser Asn Arg Ala Thr Gly Ile
1               5

<210> SEQ ID NO 50
<211> LENGTH: 9
<212> TYPE: PRT
<213> ORGANISM: Artificial
<220> FEATURE:
<223> OTHER INFORMATION: Synthetic Construct
```

<400> SEQUENCE: 50

Asp Ala Ser Ser Leu Glu Ser Gly Val
1               5

<210> SEQ ID NO 51
<211> LENGTH: 9
<212> TYPE: PRT
<213> ORGANISM: Artificial
<220> FEATURE:
<223> OTHER INFORMATION: Synthetic Construct

<400> SEQUENCE: 51

Asp Ala Ser Asn Arg Ala Thr Gly Ile
1               5

<210> SEQ ID NO 52
<211> LENGTH: 9
<212> TYPE: PRT
<213> ORGANISM: Artificial
<220> FEATURE:
<223> OTHER INFORMATION: Synthetic Construct

<400> SEQUENCE: 52

Asp Ala Ser Asn Leu Glu Thr Gly Val
1               5

<210> SEQ ID NO 53
<211> LENGTH: 9
<212> TYPE: PRT
<213> ORGANISM: Artificial
<220> FEATURE:
<223> OTHER INFORMATION: Synthetic Construct

<400> SEQUENCE: 53

Asp Ala Ser Asn Arg Ala Thr Gly Ile
1               5

<210> SEQ ID NO 54
<211> LENGTH: 9
<212> TYPE: PRT
<213> ORGANISM: Artificial
<220> FEATURE:
<223> OTHER INFORMATION: Synthetic Construct

<400> SEQUENCE: 54

Asp Ala Ser Asn Arg Ala Thr Gly Ile
1               5

<210> SEQ ID NO 55
<211> LENGTH: 9
<212> TYPE: PRT
<213> ORGANISM: Artificial
<220> FEATURE:
<223> OTHER INFORMATION: Synthetic Construct

<400> SEQUENCE: 55

Asp Ala Ser Ser Leu Glu Ser Gly Val
1               5

<210> SEQ ID NO 56
<211> LENGTH: 9
<212> TYPE: PRT
<213> ORGANISM: Artificial
<220> FEATURE:
<223> OTHER INFORMATION: Synthetic Construct

```
<400> SEQUENCE: 56

Asp Ala Ser Asn Arg Ala Thr Gly Ile
1               5

<210> SEQ ID NO 57
<211> LENGTH: 9
<212> TYPE: PRT
<213> ORGANISM: Artificial
<220> FEATURE:
<223> OTHER INFORMATION: Synthetic Construct

<400> SEQUENCE: 57

Asp Ala Ser Asn Arg Ala Thr Gly Ile
1               5

<210> SEQ ID NO 58
<211> LENGTH: 9
<212> TYPE: PRT
<213> ORGANISM: Artificial
<220> FEATURE:
<223> OTHER INFORMATION: Synthetic Construct

<400> SEQUENCE: 58

Asp Ala Ser Ser Leu Glu Ser Gly Val
1               5

<210> SEQ ID NO 59
<211> LENGTH: 9
<212> TYPE: PRT
<213> ORGANISM: Artificial
<220> FEATURE:
<223> OTHER INFORMATION: Synthetic Construct

<400> SEQUENCE: 59

Asp Ala Ser Ser Leu Glu Ser Gly Val
1               5

<210> SEQ ID NO 60
<211> LENGTH: 9
<212> TYPE: PRT
<213> ORGANISM: Artificial
<220> FEATURE:
<223> OTHER INFORMATION: Synthetic Construct

<400> SEQUENCE: 60

Asp Ala Ser Ser Leu Glu Ser Gly Val
1               5

<210> SEQ ID NO 61
<211> LENGTH: 9
<212> TYPE: PRT
<213> ORGANISM: Artificial
<220> FEATURE:
<223> OTHER INFORMATION: Synthetic Construct

<400> SEQUENCE: 61

Asp Ala Ser Asn Arg Ala Thr Gly Ile
1               5

<210> SEQ ID NO 62
<211> LENGTH: 9
<212> TYPE: PRT
<213> ORGANISM: Artificial
<220> FEATURE:
<223> OTHER INFORMATION: Synthetic Construct

<400> SEQUENCE: 62
```

```
Asp Ala Ser Ser Leu Glu Ser Gly Val
1               5

<210> SEQ ID NO 63
<211> LENGTH: 9
<212> TYPE: PRT
<213> ORGANISM: Artificial
<220> FEATURE:
<223> OTHER INFORMATION: Synthetic Construct

<400> SEQUENCE: 63

Asp Ala Ser Asn Leu Glu Thr Gly Val
1               5

<210> SEQ ID NO 64
<211> LENGTH: 9
<212> TYPE: PRT
<213> ORGANISM: Artificial
<220> FEATURE:
<223> OTHER INFORMATION: Synthetic Construct

<400> SEQUENCE: 64

Asp Ala Ser Asn Leu Glu Thr Gly Val
1               5

<210> SEQ ID NO 65
<211> LENGTH: 9
<212> TYPE: PRT
<213> ORGANISM: Artificial
<220> FEATURE:
<223> OTHER INFORMATION: Synthetic Construct

<400> SEQUENCE: 65

Asp Ala Ser Asn Arg Ala Thr Gly Ile
1               5

<210> SEQ ID NO 66
<211> LENGTH: 9
<212> TYPE: PRT
<213> ORGANISM: Artificial
<220> FEATURE:
<223> OTHER INFORMATION: Synthetic Construct

<400> SEQUENCE: 66

Asp Ala Ser Asn Leu Glu Thr Gly Val
1               5

<210> SEQ ID NO 67
<211> LENGTH: 11
<212> TYPE: PRT
<213> ORGANISM: Artificial
<220> FEATURE:
<223> OTHER INFORMATION: Synthetic Construct

<400> SEQUENCE: 67

Tyr Cys Gln Gln Tyr Asp Tyr Trp Pro Tyr Thr
1               5                   10

<210> SEQ ID NO 68
<211> LENGTH: 11
<212> TYPE: PRT
<213> ORGANISM: Artificial
<220> FEATURE:
<223> OTHER INFORMATION: Synthetic Construct

<400> SEQUENCE: 68
```

Tyr Cys Gln Gln Tyr Asp Ser Trp Pro Tyr Thr
1               5                   10

<210> SEQ ID NO 69
<211> LENGTH: 11
<212> TYPE: PRT
<213> ORGANISM: Artificial
<220> FEATURE:
<223> OTHER INFORMATION: Synthetic Construct

<400> SEQUENCE: 69

Tyr Cys Gln Gln Tyr Asp His Trp Pro Tyr Thr
1               5                   10

<210> SEQ ID NO 70
<211> LENGTH: 11
<212> TYPE: PRT
<213> ORGANISM: Artificial
<220> FEATURE:
<223> OTHER INFORMATION: Synthetic Construct

<400> SEQUENCE: 70

Tyr Cys Gln Gln Tyr Asp Ser Trp Pro Tyr Thr
1               5                   10

<210> SEQ ID NO 71
<211> LENGTH: 11
<212> TYPE: PRT
<213> ORGANISM: Artificial
<220> FEATURE:
<223> OTHER INFORMATION: Synthetic Construct

<400> SEQUENCE: 71

Tyr Cys Gln Gln Tyr Asp Ser Trp Pro Tyr Thr
1               5                   10

<210> SEQ ID NO 72
<211> LENGTH: 11
<212> TYPE: PRT
<213> ORGANISM: Artificial
<220> FEATURE:
<223> OTHER INFORMATION: Synthetic Construct

<400> SEQUENCE: 72

Tyr Cys Gln Gln Tyr Asp Ser Trp Pro Tyr Thr
1               5                   10

<210> SEQ ID NO 73
<211> LENGTH: 11
<212> TYPE: PRT
<213> ORGANISM: Artificial
<220> FEATURE:
<223> OTHER INFORMATION: Synthetic Construct

<400> SEQUENCE: 73

Tyr Cys Gln Gln Tyr Asp His Trp Pro Tyr Thr
1               5                   10

<210> SEQ ID NO 74
<211> LENGTH: 11
<212> TYPE: PRT
<213> ORGANISM: Artificial
<220> FEATURE:
<223> OTHER INFORMATION: Synthetic Construct

<400> SEQUENCE: 74

Tyr Cys Gln Gln Tyr Asp His Trp Pro Tyr Thr

```
<210> SEQ ID NO 75
<211> LENGTH: 11
<212> TYPE: PRT
<213> ORGANISM: Artificial
<220> FEATURE:
<223> OTHER INFORMATION: Synthetic Construct

<400> SEQUENCE: 75

Tyr Cys Gln Gln Tyr Asp Ala Trp Pro Tyr Thr
1               5                   10

<210> SEQ ID NO 76
<211> LENGTH: 11
<212> TYPE: PRT
<213> ORGANISM: Artificial
<220> FEATURE:
<223> OTHER INFORMATION: Synthetic Construct

<400> SEQUENCE: 76

Tyr Cys Gln Gln Tyr Asp Ser Trp Pro Tyr Thr
1               5                   10

<210> SEQ ID NO 77
<211> LENGTH: 11
<212> TYPE: PRT
<213> ORGANISM: Artificial
<220> FEATURE:
<223> OTHER INFORMATION: Synthetic Construct

<400> SEQUENCE: 77

Tyr Cys Gln Gln Tyr Asp Ala Trp Pro Tyr Thr
1               5                   10

<210> SEQ ID NO 78
<211> LENGTH: 11
<212> TYPE: PRT
<213> ORGANISM: Artificial
<220> FEATURE:
<223> OTHER INFORMATION: Synthetic Construct

<400> SEQUENCE: 78

Tyr Cys Gln Gln Tyr Asp Tyr Trp Pro Tyr Thr
1               5                   10

<210> SEQ ID NO 79
<211> LENGTH: 11
<212> TYPE: PRT
<213> ORGANISM: Artificial
<220> FEATURE:
<223> OTHER INFORMATION: Synthetic Construct

<400> SEQUENCE: 79

Tyr Cys Gln Gln Tyr Asp Ala Trp Pro Tyr Thr
1               5                   10

<210> SEQ ID NO 80
<211> LENGTH: 11
<212> TYPE: PRT
<213> ORGANISM: Artificial
<220> FEATURE:
<223> OTHER INFORMATION: Synthetic Construct

<400> SEQUENCE: 80

Tyr Cys Gln Gln Tyr Asp His Trp Pro Tyr Thr
1               5                   10
```

```
<210> SEQ ID NO 81
<211> LENGTH: 11
<212> TYPE: PRT
<213> ORGANISM: Artificial
<220> FEATURE:
<223> OTHER INFORMATION: Synthetic Construct

<400> SEQUENCE: 81

Tyr Cys Gln Gln Tyr Asp His Trp Pro Tyr Thr
1               5                   10

<210> SEQ ID NO 82
<211> LENGTH: 11
<212> TYPE: PRT
<213> ORGANISM: Artificial
<220> FEATURE:
<223> OTHER INFORMATION: Synthetic Construct

<400> SEQUENCE: 82

Tyr Cys Gln Gln Tyr Asp Ala Trp Pro Tyr Thr
1               5                   10

<210> SEQ ID NO 83
<211> LENGTH: 11
<212> TYPE: PRT
<213> ORGANISM: Artificial
<220> FEATURE:
<223> OTHER INFORMATION: Synthetic Construct

<400> SEQUENCE: 83

Tyr Cys Gln Gln Tyr Asp Ala Trp Pro Tyr Thr
1               5                   10

<210> SEQ ID NO 84
<211> LENGTH: 11
<212> TYPE: PRT
<213> ORGANISM: Artificial
<220> FEATURE:
<223> OTHER INFORMATION: Synthetic Construct

<400> SEQUENCE: 84

Tyr Cys Gln Gln Tyr Asp Ser Trp Pro Tyr Thr
1               5                   10

<210> SEQ ID NO 85
<211> LENGTH: 11
<212> TYPE: PRT
<213> ORGANISM: Artificial
<220> FEATURE:
<223> OTHER INFORMATION: Synthetic Construct

<400> SEQUENCE: 85

Tyr Cys Gln Gln Tyr Asp Ser Trp Pro Tyr Thr
1               5                   10

<210> SEQ ID NO 86
<211> LENGTH: 11
<212> TYPE: PRT
<213> ORGANISM: Artificial
<220> FEATURE:
<223> OTHER INFORMATION: Synthetic Construct

<400> SEQUENCE: 86

Tyr Cys Gln Gln Tyr Asp Ser Trp Pro Tyr Thr
1               5                   10
```

```
<210> SEQ ID NO 87
<211> LENGTH: 11
<212> TYPE: PRT
<213> ORGANISM: Artificial
<220> FEATURE:
<223> OTHER INFORMATION: Synthetic Construct

<400> SEQUENCE: 87

Tyr Cys Gln Gln Tyr Asp Ala Trp Pro Tyr Thr
1               5                   10

<210> SEQ ID NO 88
<211> LENGTH: 11
<212> TYPE: PRT
<213> ORGANISM: Artificial
<220> FEATURE:
<223> OTHER INFORMATION: Synthetic Construct

<400> SEQUENCE: 88

Tyr Cys Gln Gln Tyr Asp His Trp Pro Tyr Thr
1               5                   10

<210> SEQ ID NO 89
<211> LENGTH: 11
<212> TYPE: PRT
<213> ORGANISM: Artificial
<220> FEATURE:
<223> OTHER INFORMATION: Synthetic Construct

<400> SEQUENCE: 89

Tyr Cys Gln Gln Tyr Asp His Trp Pro Tyr Thr
1               5                   10

<210> SEQ ID NO 90
<211> LENGTH: 11
<212> TYPE: PRT
<213> ORGANISM: Artificial
<220> FEATURE:
<223> OTHER INFORMATION: Synthetic Construct

<400> SEQUENCE: 90

Tyr Cys Gln Gln Tyr Asp Ser Trp Pro Tyr Thr
1               5                   10

<210> SEQ ID NO 91
<211> LENGTH: 11
<212> TYPE: PRT
<213> ORGANISM: Artificial
<220> FEATURE:
<223> OTHER INFORMATION: Synthetic Construct

<400> SEQUENCE: 91

Tyr Cys Gln Gln Tyr Asp Ala Trp Pro Tyr Thr
1               5                   10

<210> SEQ ID NO 92
<211> LENGTH: 11
<212> TYPE: PRT
<213> ORGANISM: Artificial
<220> FEATURE:
<223> OTHER INFORMATION: Synthetic Construct

<400> SEQUENCE: 92

Tyr Cys Gln Gln Tyr Asp Ser Trp Pro Tyr Thr
1               5                   10
```

```
<210> SEQ ID NO 93
<211> LENGTH: 11
<212> TYPE: PRT
<213> ORGANISM: Artificial
<220> FEATURE:
<223> OTHER INFORMATION: Synthetic Construct

<400> SEQUENCE: 93

Tyr Cys Gln Gln Tyr Asp Ala Trp Pro Tyr Thr
1               5                   10

<210> SEQ ID NO 94
<211> LENGTH: 11
<212> TYPE: PRT
<213> ORGANISM: Artificial
<220> FEATURE:
<223> OTHER INFORMATION: Synthetic Construct

<400> SEQUENCE: 94

Gln Ala Ser Gln Asp Ile Pro Thr Phe Leu Ala
1               5                   10

<210> SEQ ID NO 95
<211> LENGTH: 11
<212> TYPE: PRT
<213> ORGANISM: Artificial
<220> FEATURE:
<223> OTHER INFORMATION: Synthetic Construct

<400> SEQUENCE: 95

Arg Ala Ser Gln Thr Ile Pro Ser Phe Leu Asn
1               5                   10

<210> SEQ ID NO 96
<211> LENGTH: 11
<212> TYPE: PRT
<213> ORGANISM: Artificial
<220> FEATURE:
<223> OTHER INFORMATION: Synthetic Construct

<400> SEQUENCE: 96

Arg Ala Ser Gln Asp Ile Pro Lys Phe Leu Ala
1               5                   10

<210> SEQ ID NO 97
<211> LENGTH: 11
<212> TYPE: PRT
<213> ORGANISM: Artificial
<220> FEATURE:
<223> OTHER INFORMATION: Synthetic Construct

<400> SEQUENCE: 97

Arg Ala Ser Gln Thr Ile Pro Ser Phe Leu Asn
1               5                   10

<210> SEQ ID NO 98
<211> LENGTH: 11
<212> TYPE: PRT
<213> ORGANISM: Artificial
<220> FEATURE:
<223> OTHER INFORMATION: Synthetic Construct

<400> SEQUENCE: 98

Arg Ala Ser Gln Ser Ile Pro Ser Phe Leu Asn
1               5                   10

<210> SEQ ID NO 99
```

```
<211> LENGTH: 11
<212> TYPE: PRT
<213> ORGANISM: Artificial
<220> FEATURE:
<223> OTHER INFORMATION: Synthetic Construct

<400> SEQUENCE: 99

Arg Ala Ser Gln Ser Ile Pro Thr Phe Leu Asn
1               5                   10

<210> SEQ ID NO 100
<211> LENGTH: 11
<212> TYPE: PRT
<213> ORGANISM: Artificial
<220> FEATURE:
<223> OTHER INFORMATION: Synthetic Construct

<400> SEQUENCE: 100

Arg Ala Ser Gln Ser Ile Pro Ser Phe Leu Asn
1               5                   10

<210> SEQ ID NO 101
<211> LENGTH: 11
<212> TYPE: PRT
<213> ORGANISM: Artificial
<220> FEATURE:
<223> OTHER INFORMATION: Synthetic Construct

<400> SEQUENCE: 101

Arg Ala Ser Gln Thr Ile Pro Ser Phe Leu Asn
1               5                   10

<210> SEQ ID NO 102
<211> LENGTH: 11
<212> TYPE: PRT
<213> ORGANISM: Artificial
<220> FEATURE:
<223> OTHER INFORMATION: Synthetic Construct

<400> SEQUENCE: 102

Arg Ala Ser Gln Thr Ile Pro Ser Phe Leu Asn
1               5                   10

<210> SEQ ID NO 103
<211> LENGTH: 9
<212> TYPE: PRT
<213> ORGANISM: Artificial
<220> FEATURE:
<223> OTHER INFORMATION: Synthetic Construct

<400> SEQUENCE: 103

Ala Ala Ser Ser Leu Gln Ser Gly Val
1               5

<210> SEQ ID NO 104
<211> LENGTH: 9
<212> TYPE: PRT
<213> ORGANISM: Artificial
<220> FEATURE:
<223> OTHER INFORMATION: Synthetic Construct

<400> SEQUENCE: 104

Ala Ala Ser Thr Leu Gln Ser Gly Val
1               5

<210> SEQ ID NO 105
<211> LENGTH: 9
```

```
<212> TYPE: PRT
<213> ORGANISM: Artificial
<220> FEATURE:
<223> OTHER INFORMATION: Synthetic Construct

<400> SEQUENCE: 105

Ala Ala Ser Thr Leu Gln Ser Gly Val
1               5

<210> SEQ ID NO 106
<211> LENGTH: 9
<212> TYPE: PRT
<213> ORGANISM: Artificial
<220> FEATURE:
<223> OTHER INFORMATION: Synthetic Construct

<400> SEQUENCE: 106

Ala Ala Ser Ser Leu Gln Ser Gly Val
1               5

<210> SEQ ID NO 107
<211> LENGTH: 9
<212> TYPE: PRT
<213> ORGANISM: Artificial
<220> FEATURE:
<223> OTHER INFORMATION: Synthetic Construct

<400> SEQUENCE: 107

Ala Ala Ser Thr Leu Gln Ser Gly Val
1               5

<210> SEQ ID NO 108
<211> LENGTH: 9
<212> TYPE: PRT
<213> ORGANISM: Artificial
<220> FEATURE:
<223> OTHER INFORMATION: Synthetic Construct

<400> SEQUENCE: 108

Ala Ala Ser Thr Leu Gln Ser Gly Val
1               5

<210> SEQ ID NO 109
<211> LENGTH: 9
<212> TYPE: PRT
<213> ORGANISM: Artificial
<220> FEATURE:
<223> OTHER INFORMATION: Synthetic Construct

<400> SEQUENCE: 109

Ala Ala Ser Ser Leu Gln Ser Gly Val
1               5

<210> SEQ ID NO 110
<211> LENGTH: 9
<212> TYPE: PRT
<213> ORGANISM: Artificial
<220> FEATURE:
<223> OTHER INFORMATION: Synthetic Construct

<400> SEQUENCE: 110

Ala Ala Ser Thr Leu Gln Ser Gly Val
1               5

<210> SEQ ID NO 111
<211> LENGTH: 9
<212> TYPE: PRT
```

```
<213> ORGANISM: Artificial
<220> FEATURE:
<223> OTHER INFORMATION: Synthetic Construct

<400> SEQUENCE: 111

Ala Ala Ser Ser Leu Gln Ser Gly Val
1               5

<210> SEQ ID NO 112
<211> LENGTH: 13
<212> TYPE: PRT
<213> ORGANISM: Artificial
<220> FEATURE:
<223> OTHER INFORMATION: Synthetic Construct

<400> SEQUENCE: 112

Tyr Cys Gln Gln Tyr Val Ser Trp Pro Arg Gly Phe Thr
1               5                   10

<210> SEQ ID NO 113
<211> LENGTH: 13
<212> TYPE: PRT
<213> ORGANISM: Artificial
<220> FEATURE:
<223> OTHER INFORMATION: Synthetic Construct

<400> SEQUENCE: 113

Tyr Cys Gln His Tyr Ser Ser Trp Pro Arg Gly Phe Thr
1               5                   10

<210> SEQ ID NO 114
<211> LENGTH: 13
<212> TYPE: PRT
<213> ORGANISM: Artificial
<220> FEATURE:
<223> OTHER INFORMATION: Synthetic Construct

<400> SEQUENCE: 114

Tyr Cys Gln His Tyr Val Ser Trp Pro Arg Gln Phe Thr
1               5                   10

<210> SEQ ID NO 115
<211> LENGTH: 13
<212> TYPE: PRT
<213> ORGANISM: Artificial
<220> FEATURE:
<223> OTHER INFORMATION: Synthetic Construct

<400> SEQUENCE: 115

Tyr Cys Gln His Tyr Thr Ser Trp Pro Arg Gln Phe Thr
1               5                   10

<210> SEQ ID NO 116
<211> LENGTH: 13
<212> TYPE: PRT
<213> ORGANISM: Artificial
<220> FEATURE:
<223> OTHER INFORMATION: Synthetic Construct

<400> SEQUENCE: 116

Tyr Cys Gln Gln Tyr Ser Ser Trp Pro Arg Leu Phe Thr
1               5                   10

<210> SEQ ID NO 117
<211> LENGTH: 13
<212> TYPE: PRT
<213> ORGANISM: Artificial
```

<220> FEATURE:
<223> OTHER INFORMATION: Synthetic Construct

<400> SEQUENCE: 117

Tyr Cys Gln His Tyr Val Ser Trp Pro Arg Leu Phe Thr
1               5                   10

<210> SEQ ID NO 118
<211> LENGTH: 13
<212> TYPE: PRT
<213> ORGANISM: Artificial
<220> FEATURE:
<223> OTHER INFORMATION: Synthetic Construct

<400> SEQUENCE: 118

Tyr Cys Gln His Tyr Ile Ser Trp Pro Arg Gln Phe Thr
1               5                   10

<210> SEQ ID NO 119
<211> LENGTH: 13
<212> TYPE: PRT
<213> ORGANISM: Artificial
<220> FEATURE:
<223> OTHER INFORMATION: Synthetic Construct

<400> SEQUENCE: 119

Tyr Cys Gln His Tyr Ile Ser Trp Pro Arg Val Phe Thr
1               5                   10

<210> SEQ ID NO 120
<211> LENGTH: 13
<212> TYPE: PRT
<213> ORGANISM: Artificial
<220> FEATURE:
<223> OTHER INFORMATION: Synthetic Construct

<400> SEQUENCE: 120

Tyr Cys Gln His Tyr Gly Ser Trp Pro Arg Arg Phe Thr
1               5                   10

<210> SEQ ID NO 121
<211> LENGTH: 108
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (28)..(28)
<223> OTHER INFORMATION: Xaa = G or S
<220> FEATURE:
<221> NAME/KEY: VARIANT
<222> LOCATION: (29)..(29)
<223> OTHER INFORMATION: Xaa = I or V
<220> FEATURE:
<221> NAME/KEY: VARIANT
<222> LOCATION: (30)..(30)
<223> OTHER INFORMATION: Xaa = E, G or S
<220> FEATURE:
<221> NAME/KEY: VARIANT
<222> LOCATION: (31)..(31)
<223> OTHER INFORMATION: Xaa = K, P or S
<220> FEATURE:
<221> NAME/KEY: VARIANT
<222> LOCATION: (32)..(32)
<223> OTHER INFORMATION: Xaa = F, W or Y
<220> FEATURE:
<221> NAME/KEY: VARIANT
<222> LOCATION: (53)..(53)
<223> OTHER INFORMATION: Xaa = N or S
<220> FEATURE:

```
<221> NAME/KEY: VARIANT
<222> LOCATION: (54)..(54)
<223> OTHER INFORMATION: Xaa = L or R
<220> FEATURE:
<221> NAME/KEY: VARIANT
<222> LOCATION: (55)..(55)
<223> OTHER INFORMATION: Xaa = A or E
<220> FEATURE:
<221> NAME/KEY: VARIANT
<222> LOCATION: (56)..(56)
<223> OTHER INFORMATION: Xaa = S or T
<220> FEATURE:
<221> NAME/KEY: VARIANT
<222> LOCATION: (58)..(58)
<223> OTHER INFORMATION: Xaa = I or V
<220> FEATURE:
<221> NAME/KEY: VARIANT
<222> LOCATION: (93)..(93)
<223> OTHER INFORMATION: Xaa = A, S or Y

<400> SEQUENCE: 121

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Xaa Xaa Xaa Xaa Xaa
            20                  25                  30

Leu Ala Trp Tyr Gln Gln Lys Pro Gly Lys Ala Pro Lys Leu Leu Ile
        35                  40                  45

Tyr Asp Ala Ser Xaa Xaa Xaa Xaa Gly Xaa Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Xaa Trp Pro Tyr
                85                  90                  95

Thr Phe Gly Gln Gly Thr Lys Val Glu Ile Lys Arg
            100                 105

<210> SEQ ID NO 122
<211> LENGTH: 112
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (27)..(27)
<223> OTHER INFORMATION: Xaa = E or Q
<220> FEATURE:
<221> NAME/KEY: VARIANT
<222> LOCATION: (32)..(32)
<223> OTHER INFORMATION: Xaa = F, H or Y
<220> FEATURE:
<221> NAME/KEY: VARIANT
<222> LOCATION: (34)..(34)
<223> OTHER INFORMATION: Xaa = I or K
<220> FEATURE:
<221> NAME/KEY: VARIANT
<222> LOCATION: (38)..(38)
<223> OTHER INFORMATION: Xaa = A or D
<220> FEATURE:
<221> NAME/KEY: VARIANT
<222> LOCATION: (57)..(57)
<223> OTHER INFORMATION: Xaa = N or S
<220> FEATURE:
<221> NAME/KEY: VARIANT
<222> LOCATION: (58)..(58)
<223> OTHER INFORMATION: Xaa = L or R
<220> FEATURE:
<221> NAME/KEY: VARIANT
<222> LOCATION: (59)..(59)
<223> OTHER INFORMATION: Xaa = A or E
<220> FEATURE:
```

```
<221> NAME/KEY: VARIANT
<222> LOCATION: (60)..(60)
<223> OTHER INFORMATION: Xaa = S or T
<220> FEATURE:
<221> NAME/KEY: VARIANT
<222> LOCATION: (62)..(62)
<223> OTHER INFORMATION: Xaa = I or V
<220> FEATURE:
<221> NAME/KEY: VARIANT
<222> LOCATION: (97)..(97)
<223> OTHER INFORMATION: Xaa = A, H, S or Y

<400> SEQUENCE: 122

Asp Ile Gln Leu Thr Gln Ser Pro Ser Ser Leu Ser Ala Ser Val Gly
1               5                   10                  15

Asp Arg Val Thr Ile Thr Cys Arg Ala Ser Xaa Ser Val Asp Phe Xaa
            20                  25                  30

Gly Xaa Ser Phe Leu Xaa Trp Tyr Gln Gln Lys Pro Gly Lys Ala Pro
        35                  40                  45

Lys Leu Leu Ile Tyr Asp Ala Ser Xaa Xaa Xaa Xaa Gly Xaa Pro Ser
    50                  55                  60

Arg Phe Ser Gly Ser Gly Ser Gly Thr Asp Phe Thr Leu Thr Ile Ser
65              70                  75                  80

Ser Leu Gln Pro Glu Asp Phe Ala Thr Tyr Tyr Cys Gln Gln Tyr Asp
                85                  90                  95

Xaa Trp Pro Tyr Thr Phe Gly Gly Gly Thr Lys Val Glu Ile Lys Arg
            100                 105                 110

<210> SEQ ID NO 123
<211> LENGTH: 110
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (24)..(24)
<223> OTHER INFORMATION: Xaa = Q or R
<220> FEATURE:
<221> NAME/KEY: VARIANT
<222> LOCATION: (28)..(28)
<223> OTHER INFORMATION: Xaa = D, S or T
<220> FEATURE:
<221> NAME/KEY: VARIANT
<222> LOCATION: (31)..(31)
<223> OTHER INFORMATION: Xaa = K, S or T
<220> FEATURE:
<221> NAME/KEY: VARIANT
<222> LOCATION: (34)..(34)
<223> OTHER INFORMATION: Xaa = A or N
<220> FEATURE:
<221> NAME/KEY: VARIANT
<222> LOCATION: (53)..(53)
<223> OTHER INFORMATION: Xaa = S or T
<220> FEATURE:
<221> NAME/KEY: VARIANT
<222> LOCATION: (90)..(90)
<223> OTHER INFORMATION: Xaa = H or Q
<220> FEATURE:
<221> NAME/KEY: VARIANT
<222> LOCATION: (92)..(92)
<223> OTHER INFORMATION: Xaa = G, I, S, T or V
<220> FEATURE:
<221> NAME/KEY: VARIANT
<222> LOCATION: (97)..(97)
<223> OTHER INFORMATION: Xaa = G, L, Q, R or V

<400> SEQUENCE: 123

Asp Ile Gln Leu Thr Gln Ser Pro Ser Ser Leu Ser Ala Ser Val Gly
1               5                   10                  15
```

-continued

Asp Arg Val Thr Ile Thr Cys Xaa Ala Ser Gln Xaa Ile Pro Xaa Phe
            20                  25                  30

Leu Xaa Trp Tyr Gln Gln Lys Pro Gly Lys Ala Pro Lys Leu Leu Ile
        35                  40                  45

Tyr Ala Ala Ser Xaa Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Xaa Tyr Xaa Ser Trp Pro Arg
                85                  90                  95

Xaa Phe Thr Phe Gly Gln Gly Thr Lys Val Glu Ile Lys Arg
            100                 105                 110

<210> SEQ ID NO 124
<211> LENGTH: 108
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (29)..(29)
<223> OTHER INFORMATION: Xaa = I or V
<220> FEATURE:
<221> NAME/KEY: VARIANT
<222> LOCATION: (31)..(31)
<223> OTHER INFORMATION: Xaa = P or S
<220> FEATURE:
<221> NAME/KEY: VARIANT
<222> LOCATION: (32)..(32)
<223> OTHER INFORMATION: Xaa = W or Y
<220> FEATURE:
<221> NAME/KEY: VARIANT
<222> LOCATION: (54)..(54)
<223> OTHER INFORMATION: Xaa = L or R
<220> FEATURE:
<221> NAME/KEY: VARIANT
<222> LOCATION: (55)..(55)
<223> OTHER INFORMATION: Xaa = A or E
<220> FEATURE:
<221> NAME/KEY: VARIANT
<222> LOCATION: (58)..(58)
<223> OTHER INFORMATION: Xaa = I or V
<220> FEATURE:
<221> NAME/KEY: VARIANT
<222> LOCATION: (93)..(93)
<223> OTHER INFORMATION: Xaa = A or S

<400> SEQUENCE: 124

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Xaa Ser Xaa Xaa
            20                  25                  30

Leu Ala Trp Tyr Gln Gln Lys Pro Gly Lys Ala Pro Lys Leu Leu Ile
        35                  40                  45

Tyr Asp Ala Ser Asn Xaa Xaa Thr Gly Xaa Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Xaa Trp Pro Tyr
                85                  90                  95

Thr Phe Gly Gln Gly Thr Lys Val Glu Ile Lys Arg
            100                 105

```
<210> SEQ ID NO 125
<211> LENGTH: 110
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (28)..(28)
<223> OTHER INFORMATION: Xaa = S or T
<220> FEATURE:
<221> NAME/KEY: VARIANT
<222> LOCATION: (92)..(92)
<223> OTHER INFORMATION: Xaa = I or T

<400> SEQUENCE: 125

Asp Ile Gln Leu Thr Gln Ser Pro Ser Ser Leu Ser Ala Ser Val Gly
 1               5                   10                  15

Asp Arg Val Thr Ile Thr Cys Arg Ala Ser Gln Xaa Ile Pro Ser Phe
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Xaa Ser Trp Pro Arg
                 85                  90                  95

Gln Phe Thr Phe Gly Gln Gly Thr Lys Val Glu Ile Lys Arg
            100                 105                 110

<210> SEQ ID NO 126
<211> LENGTH: 120
<212> TYPE: PRT
<213> ORGANISM: Artificial
<220> FEATURE:
<223> OTHER INFORMATION: Synthetic Construct

<400> SEQUENCE: 126

Glu Val Gln Leu Val Glu Ser Gly Gly Gly Leu Val Gln Pro Gly Gly
 1               5                   10                  15

Ser Leu Arg Leu Ser Cys Ala Ala Ser Gly Tyr Thr Phe Ser Asn Tyr
             20                  25                  30

Gly Ile His Trp Val Arg Gln Ala Pro Gly Lys Gly Leu Glu Trp Ile
         35                  40                  45

Gly Trp Ile Tyr Pro Ser Gly Gly Thr Lys Tyr Ala Gln Lys Phe
 50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                 85                  90                  95

Ala Arg Glu Gly Gly Gly Tyr Gly Tyr Ala Leu Asp Tyr Trp Gly Gln
            100                 105                 110

Gly Thr Leu Val Thr Val Ser Ser
        115                 120

<210> SEQ ID NO 127
<211> LENGTH: 118
<212> TYPE: PRT
<213> ORGANISM: Artificial
<220> FEATURE:
<223> OTHER INFORMATION: Synthetic Construct
```

<400> SEQUENCE: 127

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr Tyr Trp Gly Trp Ile Arg Gln Ala Pro Gly Lys Gly Leu Glu Trp
        35                  40                  45

Ile Gly Ile Ile Tyr Pro Ser Gly Gly Thr Asn Tyr Ala Gln Lys
50                  55                  60

Phe Gln Gly Arg Val Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Gly Leu Gly Phe Asp Tyr Trp Gly Gln Gly Thr
            100                 105                 110

Leu Val Thr Val Ser Ser
            115
```

<210> SEQ ID NO 128
<211> LENGTH: 110
<212> TYPE: PRT
<213> ORGANISM: Artificial
<220> FEATURE:
<223> OTHER INFORMATION: Synthetic Construct

<400> SEQUENCE: 128

```
Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Pro Thr Phe
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Trp Pro Arg
                85                  90                  95

Gly Phe Thr Phe Gly Gln Gly Thr Lys Val Glu Ile Lys Arg
            100                 105                 110
```

<210> SEQ ID NO 129
<211> LENGTH: 108
<212> TYPE: PRT
<213> ORGANISM: Artificial
<220> FEATURE:
<223> OTHER INFORMATION: Synthetic Construct

<400> SEQUENCE: 129

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Phe
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Tyr Trp Pro Tyr
                85                  90                  95

Thr Phe Gly Gln Gly Thr Lys Val Glu Ile Lys Arg
            100                 105

<210> SEQ ID NO 130
<211> LENGTH: 112
<212> TYPE: PRT
<213> ORGANISM: Artificial
<220> FEATURE:
<223> OTHER INFORMATION: Synthetic Construct

<400> SEQUENCE: 130

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Tyr
            20                  25                  30

Gly Lys Ser Phe Leu Asp Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

Ser Trp Pro Tyr Thr Phe Gly Gln Gly Thr Lys Val Glu Ile Lys Arg
            100                 105                 110

<210> SEQ ID NO 131
<211> LENGTH: 112
<212> TYPE: PRT
<213> ORGANISM: Artificial
<220> FEATURE:
<223> OTHER INFORMATION: Synthetic Construct

<400> SEQUENCE: 131

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Lys Ser Phe Leu Ala Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

His Trp Pro Tyr Thr Phe Gly Gln Gly Thr Lys Val Glu Ile Lys Arg
            100                 105                 110

<210> SEQ ID NO 132
<211> LENGTH: 112
<212> TYPE: PRT
<213> ORGANISM: Artificial
<220> FEATURE:
<223> OTHER INFORMATION: Synthetic Construct

<400> SEQUENCE: 132

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Phe
            20                  25                  30

Gly Lys Ser Phe Leu Ala Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

Ser Trp Pro Tyr Thr Phe Gly Gln Gly Thr Lys Val Glu Ile Lys Arg
            100                 105                 110

<210> SEQ ID NO 133
<211> LENGTH: 112
<212> TYPE: PRT
<213> ORGANISM: Artificial
<220> FEATURE:
<223> OTHER INFORMATION: Synthetic Construct

<400> SEQUENCE: 133

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Lys Ser Phe Leu Asp Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

Ser Trp Pro Tyr Thr Phe Gly Gln Gly Thr Lys Val Glu Ile Lys Arg
            100                 105                 110

<210> SEQ ID NO 134
<211> LENGTH: 108
<212> TYPE: PRT
<213> ORGANISM: Artificial
<220> FEATURE:
<223> OTHER INFORMATION: Synthetic Construct

<400> SEQUENCE: 134

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Trp Pro Tyr
            85                  90                  95

Thr Phe Gly Gln Gly Thr Lys Val Glu Ile Lys Arg
            100                 105

<210> SEQ ID NO 135
<211> LENGTH: 112
<212> TYPE: PRT
<213> ORGANISM: Artificial
<220> FEATURE:
<223> OTHER INFORMATION: Synthetic Construct

<400> SEQUENCE: 135

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Phe
            20                  25                  30

Gly Lys Ser Phe Leu Ala Trp Tyr Gln Gln Lys Pro Gly Lys Ala Pro
        35                  40                  45

Lys Leu Leu Ile Tyr Asp Ala Ser Asn Leu Glu Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

His Trp Pro Tyr Thr Phe Gly Gln Gly Thr Lys Val Glu Ile Lys Arg
            100                 105                 110

<210> SEQ ID NO 136
<211> LENGTH: 112
<212> TYPE: PRT
<213> ORGANISM: Artificial
<220> FEATURE:
<223> OTHER INFORMATION: Synthetic Construct

<400> SEQUENCE: 136

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe His
            20                  25                  30

Gly Ile Ser Phe Leu Ala Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

His Trp Pro Tyr Thr Phe Gly Gln Gly Thr Lys Val Glu Ile Lys Arg
            100                 105                 110

<210> SEQ ID NO 137
<211> LENGTH: 108
<212> TYPE: PRT
<213> ORGANISM: Artificial
<220> FEATURE:
<223> OTHER INFORMATION: Synthetic Construct

<400> SEQUENCE: 137

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Pro Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Asp Ala Trp Pro Tyr
                85                  90                  95

Thr Phe Gly Gln Gly Thr Lys Val Glu Ile Lys Arg
            100                 105

<210> SEQ ID NO 138
<211> LENGTH: 109
<212> TYPE: PRT
<213> ORGANISM: Artificial
<220> FEATURE:
<223> OTHER INFORMATION: Synthetic Construct

<400> SEQUENCE: 138

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Gly Ser Ile
            20                  25                  30

Tyr Leu Gly Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65              70                  75                  80

Pro Glu Asp Phe Ala Thr Tyr Tyr Cys Gln Gln Tyr Asp Ser Trp Pro
                85                  90                  95

Tyr Thr Phe Gly Gln Gly Thr Lys Val Glu Ile Lys Arg
            100                 105

<210> SEQ ID NO 139
<211> LENGTH: 112
<212> TYPE: PRT
<213> ORGANISM: Artificial
<220> FEATURE:
<223> OTHER INFORMATION: Synthetic Construct

<400> SEQUENCE: 139

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Lys Ser Phe Leu Ala Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
    50                  55                  60

Arg Phe Ser Gly Ser Gly Ser Gly Thr Asp Phe Thr Leu Thr Ile Ser
65              70                  75                  80

Ser Leu Gln Pro Glu Asp Phe Ala Thr Tyr Tyr Cys Gln Gln Tyr Asp
                85                  90                  95

```
Ala Trp Pro Tyr Thr Phe Gly Gln Gly Thr Lys Val Glu Ile Lys Arg
            100                 105                 110
```

<210> SEQ ID NO 140
<211> LENGTH: 112
<212> TYPE: PRT
<213> ORGANISM: Artificial
<220> FEATURE:
<223> OTHER INFORMATION: Synthetic Construct

<400> SEQUENCE: 140

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Tyr
            20                  25                  30

Gly Lys Ser Phe Leu Ala Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

Tyr Trp Pro Tyr Thr Phe Gly Gly Thr Lys Val Glu Ile Lys Arg
            100                 105                 110
```

<210> SEQ ID NO 141
<211> LENGTH: 112
<212> TYPE: PRT
<213> ORGANISM: Artificial
<220> FEATURE:
<223> OTHER INFORMATION: Synthetic Construct

<400> SEQUENCE: 141

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Lys Ser Phe Leu Asp Trp Tyr Gln Gln Lys Pro Gly Lys Ala Pro
        35                  40                  45

Lys Leu Leu Ile Tyr Asp Ala Ser Asn Leu Glu Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

Ala Trp Pro Tyr Thr Phe Gly Gln Gly Thr Lys Val Glu Ile Lys Arg
            100                 105                 110
```

<210> SEQ ID NO 142
<211> LENGTH: 112
<212> TYPE: PRT
<213> ORGANISM: Artificial
<220> FEATURE:
<223> OTHER INFORMATION: Synthetic Construct

<400> SEQUENCE: 142

```
Asp Ile Gln Leu Thr Gln Ser Pro Ser Ser Leu Ser Ala Ser Val Gly
1               5                   10                  15
```

```
Asp Arg Val Thr Ile Thr Cys Arg Ala Ser Glu Ser Val Asp Phe Tyr
                20                  25                  30

Gly Lys Ser Phe Leu Asp Trp Tyr Gln Gln Lys Pro Gly Lys Ala Pro
            35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
            85                  90                  95

His Trp Pro Tyr Thr Phe Gly Gln Gly Thr Lys Val Glu Ile Lys Arg
        100                 105                 110
```

<210> SEQ ID NO 143
<211> LENGTH: 112
<212> TYPE: PRT
<213> ORGANISM: Artificial
<220> FEATURE:
<223> OTHER INFORMATION: Synthetic Construct

<400> SEQUENCE: 143

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe His
                20                  25                  30

Gly Lys Ser Phe Leu Ala Trp Tyr Gln Gln Lys Pro Gly Lys Ala Pro
            35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
            85                  90                  95

His Trp Pro Tyr Thr Phe Gly Gln Gly Thr Lys Val Glu Ile Lys Arg
        100                 105                 110
```

<210> SEQ ID NO 144
<211> LENGTH: 108
<212> TYPE: PRT
<213> ORGANISM: Artificial
<220> FEATURE:
<223> OTHER INFORMATION: Synthetic Construct

<400> SEQUENCE: 144

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Pro Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ala Trp Pro Tyr
            85                  90                  95

Thr Phe Gly Gln Gly Thr Lys Val Glu Ile Lys Arg
        100                 105
```

```
<210> SEQ ID NO 145
<211> LENGTH: 108
<212> TYPE: PRT
<213> ORGANISM: Artificial
<220> FEATURE:
<223> OTHER INFORMATION: Synthetic Construct

<400> SEQUENCE: 145

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Pro Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ala Trp Pro Tyr
                85                  90                  95

Thr Phe Gly Gln Gly Thr Lys Val Glu Ile Lys Arg
            100                 105

<210> SEQ ID NO 146
<211> LENGTH: 112
<212> TYPE: PRT
<213> ORGANISM: Artificial
<220> FEATURE:
<223> OTHER INFORMATION: Synthetic Construct

<400> SEQUENCE: 146

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe His
            20                  25                  30

Gly Lys Ser Phe Leu Asp Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

Ser Trp Pro Tyr Thr Phe Gly Gln Gly Thr Lys Val Glu Ile Lys Arg
            100                 105                 110

<210> SEQ ID NO 147
<211> LENGTH: 112
<212> TYPE: PRT
<213> ORGANISM: Artificial
<220> FEATURE:
<223> OTHER INFORMATION: Synthetic Construct

<400> SEQUENCE: 147

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30
```

```
Gly Lys Ser Phe Leu Ala Trp Tyr Gln Gln Lys Pro Gly Lys Ala Pro
            35                  40                  45

Lys Leu Leu Ile Tyr Asp Ala Ser Ser Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Tyr Asp
                85                  90                  95

Ser Trp Pro Tyr Thr Phe Gly Gln Gly Thr Lys Val Glu Ile Lys Arg
               100                 105                 110
```

<210> SEQ ID NO 148
<211> LENGTH: 112
<212> TYPE: PRT
<213> ORGANISM: Artificial
<220> FEATURE:
<223> OTHER INFORMATION: Synthetic Construct

<400> SEQUENCE: 148

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Glu Ser Val Asp Phe Tyr
                20                  25                  30

Gly Lys Ser Phe Leu Ala Trp Tyr Gln Gln Lys Pro Gly Lys Ala Pro
            35                  40                  45

Lys Leu Leu Ile Tyr Asp Ala Ser Ser Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Tyr Asp
                85                  90                  95

Ser Trp Pro Tyr Thr Phe Gly Gln Gly Thr Lys Val Glu Ile Lys Arg
               100                 105                 110
```

<210> SEQ ID NO 149
<211> LENGTH: 108
<212> TYPE: PRT
<213> ORGANISM: Artificial
<220> FEATURE:
<223> OTHER INFORMATION: Synthetic Construct

<400> SEQUENCE: 149

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Ile Glu Lys Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
             50                 55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asp Ala Trp Pro Tyr
                85                  90                  95

Thr Phe Gly Gln Gly Thr Lys Val Glu Ile Lys Arg
                100                 105
```

<210> SEQ ID NO 150

```
<211> LENGTH: 112
<212> TYPE: PRT
<213> ORGANISM: Artificial
<220> FEATURE:
<223> OTHER INFORMATION: Synthetic Construct

<400> SEQUENCE: 150

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe His
            20                  25                  30

Gly Ile Ser Phe Leu Asp Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

His Trp Pro Tyr Thr Phe Gly Gln Gly Thr Lys Val Glu Ile Lys Arg
            100                 105                 110

<210> SEQ ID NO 151
<211> LENGTH: 112
<212> TYPE: PRT
<213> ORGANISM: Artificial
<220> FEATURE:
<223> OTHER INFORMATION: Synthetic Construct

<400> SEQUENCE: 151

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Lys Ser Phe Leu Asp Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

His Trp Pro Tyr Thr Phe Gly Gln Gly Thr Lys Val Glu Ile Lys Arg
            100                 105                 110

<210> SEQ ID NO 152
<211> LENGTH: 112
<212> TYPE: PRT
<213> ORGANISM: Artificial
<220> FEATURE:
<223> OTHER INFORMATION: Synthetic Construct

<400> SEQUENCE: 152

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe His
            20                  25                  30

Gly Ile Ser Phe Leu Asp Trp Tyr Gln Gln Lys Pro Gly Lys Ala Pro
        35                  40                  45
```

```
Lys Leu Leu Ile Tyr Asp Ala Ser Asn Leu Glu Thr Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Tyr Asp
                 85                  90                  95

Ser Trp Pro Tyr Thr Phe Gly Gln Gly Thr Lys Val Glu Ile Lys Arg
                100                 105                 110

<210> SEQ ID NO 153
<211> LENGTH: 110
<212> TYPE: PRT
<213> ORGANISM: Artificial
<220> FEATURE:
<223> OTHER INFORMATION: Synthetic Construct

<400> SEQUENCE: 153

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Thr Ile Pro Ser Phe
                 20                  25                  30

Leu Asn Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Tyr Ser Ser Trp Pro Arg
                 85                  90                  95

Gly Phe Thr Phe Gly Gln Gly Thr Lys Val Glu Ile Lys Arg
                100                 105                 110

<210> SEQ ID NO 154
<211> LENGTH: 110
<212> TYPE: PRT
<213> ORGANISM: Artificial
<220> FEATURE:
<223> OTHER INFORMATION: Synthetic Construct

<400> SEQUENCE: 154

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asp Ile Pro Lys Phe
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Tyr Val Ser Trp Pro Arg
                 85                  90                  95

Gln Phe Thr Phe Gly Gln Gly Thr Lys Val Glu Ile Lys Arg
                100                 105                 110

<210> SEQ ID NO 155
<211> LENGTH: 110
<212> TYPE: PRT
<213> ORGANISM: Artificial
```

```
<220> FEATURE:
<223> OTHER INFORMATION: Synthetic Construct

<400> SEQUENCE: 155

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Thr Ile Pro Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Thr Ser Trp Pro Arg
                85                  90                  95

Gln Phe Thr Phe Gly Gln Gly Thr Lys Val Glu Ile Lys Arg
            100                 105                 110

<210> SEQ ID NO 156
<211> LENGTH: 110
<212> TYPE: PRT
<213> ORGANISM: Artificial
<220> FEATURE:
<223> OTHER INFORMATION: Synthetic Construct

<400> SEQUENCE: 156

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Pro Ser Phe
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Trp Pro Arg
                85                  90                  95

Leu Phe Thr Phe Gly Gln Gly Thr Lys Val Glu Ile Lys Arg
            100                 105                 110

<210> SEQ ID NO 157
<211> LENGTH: 110
<212> TYPE: PRT
<213> ORGANISM: Artificial
<220> FEATURE:
<223> OTHER INFORMATION: Synthetic Construct

<400> SEQUENCE: 157

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Pro Thr Phe
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60
```

-continued

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Val Ser Trp Pro Arg
                85                  90                  95

Leu Phe Thr Phe Gly Gln Gly Thr Lys Val Glu Ile Lys Arg
            100                 105                 110

<210> SEQ ID NO 158
<211> LENGTH: 110
<212> TYPE: PRT
<213> ORGANISM: Artificial
<220> FEATURE:
<223> OTHER INFORMATION: Synthetic Construct

<400> SEQUENCE: 158

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Pro Ser Phe
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Ile Ser Trp Pro Arg
                85                  90                  95

Gln Phe Thr Phe Gly Gln Gly Thr Lys Val Glu Ile Lys Arg
            100                 105                 110

<210> SEQ ID NO 159
<211> LENGTH: 110
<212> TYPE: PRT
<213> ORGANISM: Artificial
<220> FEATURE:
<223> OTHER INFORMATION: Synthetic Construct

<400> SEQUENCE: 159

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Thr Ile Pro Ser Phe
                20                  25                  30

Leu Asn Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Ile Ser Trp Pro Arg
                85                  90                  95

Val Phe Thr Phe Gly Gln Gly Thr Lys Val Glu Ile Lys Arg
            100                 105                 110

<210> SEQ ID NO 160
<211> LENGTH: 110
<212> TYPE: PRT
<213> ORGANISM: Artificial
<220> FEATURE:
<223> OTHER INFORMATION: Synthetic Construct

<400> SEQUENCE: 160

Asp Ile Gln Leu Thr Gln Ser Pro Ser Leu Ser Ala Ser Val Gly
1               5                   10                  15

Asp Arg Val Thr Ile Thr Cys Arg Ala Ser Gln Thr Ile Pro Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Gly Ser Trp Pro Arg
                85                  90                  95

Arg Phe Thr Phe Gly Gln Gly Thr Lys Val Glu Ile Lys Arg
            100                 105                 110

<210> SEQ ID NO 161
<211> LENGTH: 108
<212> TYPE: PRT
<213> ORGANISM: Artificial
<220> FEATURE:
<223> OTHER INFORMATION: Synthetic Construct

<400> SEQUENCE: 161

Asp Ile Gln Leu Thr Gln Ser Pro Ser Leu Ser Ala Ser Val Gly
1               5                   10                  15

Asp Arg Val Thr Ile Thr Cys Arg Ala Ser Gln Gly Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ala Trp Pro Tyr
                85                  90                  95

Thr Phe Gly Gln Gly Thr Lys Val Glu Ile Lys Arg
            100                 105

<210> SEQ ID NO 162
<211> LENGTH: 108
<212> TYPE: PRT
<213> ORGANISM: Artificial
<220> FEATURE:
<223> OTHER INFORMATION: Synthetic Construct

<400> SEQUENCE: 162

Asp Ile Gln Leu Thr Gln Ser Pro Ser Leu Ser Ala Ser Val Gly
1               5                   10                  15

Asp Arg Val Thr Ile Thr Cys Arg Ala Ser Gln Gly Ile Ser Pro Trp
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Trp Pro Tyr
                85                  90                  95

Thr Phe Gly Gln Gly Thr Lys Val Glu Ile Lys Arg
            100                 105

<210> SEQ ID NO 163
<211> LENGTH: 108
<212> TYPE: PRT
<213> ORGANISM: Artificial
<220> FEATURE:
<223> OTHER INFORMATION: Synthetic Construct

<400> SEQUENCE: 163

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ala Trp Pro Tyr
                85                  90                  95

Thr Phe Gly Gln Gly Thr Lys Val Glu Ile Lys Arg
            100                 105

<210> SEQ ID NO 164
<211> LENGTH: 11
<212> TYPE: PRT
<213> ORGANISM: Artificial
<220> FEATURE:
<223> OTHER INFORMATION: Synthetic Construct

<400> SEQUENCE: 164

Tyr Thr Phe Ser Asn Tyr Gly Ile His Trp Val
1               5                   10

<210> SEQ ID NO 165
<211> LENGTH: 21
<212> TYPE: PRT
<213> ORGANISM: Artificial
<220> FEATURE:
<223> OTHER INFORMATION: Synthetic Construct

<400> SEQUENCE: 165

Ile Gly Trp Ile Tyr Pro Ser Gly Gly Gly Thr Lys Tyr Ala Gln Lys
1               5                   10                  15

Phe Gln Gly Arg Val
            20

<210> SEQ ID NO 166
<211> LENGTH: 13
<212> TYPE: PRT
<213> ORGANISM: Artificial
<220> FEATURE:
<223> OTHER INFORMATION: Synthetic Construct

<400> SEQUENCE: 166

Ala Arg Glu Gly Gly Gly Tyr Gly Tyr Ala Leu Asp Tyr
1               5                   10

<210> SEQ ID NO 167
<211> LENGTH: 12
<212> TYPE: PRT
<213> ORGANISM: Artificial
<220> FEATURE:
<223> OTHER INFORMATION: Synthetic Construct

<400> SEQUENCE: 167

Tyr Ser Ile Ser Ser Gly Tyr Tyr Trp Gly Trp Ile
1               5                   10

<210> SEQ ID NO 168
<211> LENGTH: 21
<212> TYPE: PRT
<213> ORGANISM: Artificial
<220> FEATURE:
<223> OTHER INFORMATION: Synthetic Construct

<400> SEQUENCE: 168

Ile Gly Ile Ile Tyr Pro Ser Gly Gly Thr Asn Tyr Ala Gln Lys
1               5                   10                  15

Phe Gln Gly Arg Val
            20

<210> SEQ ID NO 169
<211> LENGTH: 10
<212> TYPE: PRT
<213> ORGANISM: Artificial
<220> FEATURE:
<223> OTHER INFORMATION: Synthetic Construct

<400> SEQUENCE: 169

Ala Arg Gly Gly Gly Leu Gly Phe Asp Tyr
1               5                   10

<210> SEQ ID NO 170
<211> LENGTH: 118
<212> TYPE: PRT
<213> ORGANISM: Artificial
<220> FEATURE:
<223> OTHER INFORMATION: Synthetic Construct

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
            115

<210> SEQ ID NO 171
<211> LENGTH: 108

<212> TYPE: PRT
<213> ORGANISM: Artificial
<220> FEATURE:
<223> OTHER INFORMATION: Synthetic Construct

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 172
<211> LENGTH: 11
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = F or Y
<220> FEATURE:
<221> NAME/KEY: VARIANT
<222> LOCATION: (4)..(4)
<223> OTHER INFORMATION: Xaa = S or T
<220> FEATURE:
<221> NAME/KEY: VARIANT
<222> LOCATION: (5)..(5)
<223> OTHER INFORMATION: Xaa = G, N or S
<220> FEATURE:
<221> NAME/KEY: VARIANT
<222> LOCATION: (7)..(7)
<223> OTHER INFORMATION: Xaa = A, G or W

<400> SEQUENCE: 172

Xaa Thr Phe Xaa Xaa Tyr Xaa Ile His Trp Val
1               5                   10

<210> SEQ ID NO 173
<211> LENGTH: 12
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (4)..(4)
<223> OTHER INFORMATION: Xaa = S or T
<220> FEATURE:
<221> NAME/KEY: VARIANT
<222> LOCATION: (7)..(7)
<223> OTHER INFORMATION: Xaa = H or Y
<220> FEATURE:
<221> NAME/KEY: VARIANT
<222> LOCATION: (8)..(8)
<223> OTHER INFORMATION: Xaa = H or Y
<220> FEATURE:
<221> NAME/KEY: VARIANT
<222> LOCATION: (10)..(10)

```
<223> OTHER INFORMATION: Xaa = A, D, G, N, S or T

<400> SEQUENCE: 173

Tyr Ser Ile Xaa Ser Gly Xaa Xaa Trp Xaa Trp Ile
1               5                   10

<210> SEQ ID NO 174
<211> LENGTH: 13
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (6)..(6)
<223> OTHER INFORMATION: Xaa = G or S
<220> FEATURE:
<221> NAME/KEY: VARIANT
<222> LOCATION: (9)..(9)
<223> OTHER INFORMATION: Xaa = A or G
<220> FEATURE:
<221> NAME/KEY: VARIANT
<222> LOCATION: (11)..(11)
<223> OTHER INFORMATION: Xaa = A, G, S or T

<400> SEQUENCE: 174

Phe Ser Leu Ser Thr Xaa Gly Val Xaa Val Xaa Trp Ile
1               5                   10

<210> SEQ ID NO 175
<211> LENGTH: 20
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (7)..(7)
<223> OTHER INFORMATION: Xaa = A, D or Y
<220> FEATURE:
<221> NAME/KEY: VARIANT
<222> LOCATION: (8)..(8)
<223> OTHER INFORMATION: Xaa = D or G
<220> FEATURE:
<221> NAME/KEY: VARIANT
<222> LOCATION: (11)..(11)
<223> OTHER INFORMATION: Xaa = R, S or Y
<220> FEATURE:
<221> NAME/KEY: VARIANT
<222> LOCATION: (14)..(14)
<223> OTHER INFORMATION: Xaa = P or T

<400> SEQUENCE: 175

Leu Ala Leu Ile Asp Trp Xaa Xaa Asp Lys Xaa Tyr Ser Xaa Ser Leu
1               5                   10                  15

Lys Ser Arg Leu
            20

<210> SEQ ID NO 176
<211> LENGTH: 20
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (3)..(3)
<223> OTHER INFORMATION: Xaa = D or E
<220> FEATURE:
<221> NAME/KEY: VARIANT
<222> LOCATION: (9)..(9)
<223> OTHER INFORMATION: Xaa = N or S
```

```
<220> FEATURE:
<221> NAME/KEY: VARIANT
<222> LOCATION: (13)..(13)
<223> OTHER INFORMATION: Xaa = N or S

<400> SEQUENCE: 176

Ile Gly Xaa Ile Tyr His Ser Gly Xaa Thr Tyr Tyr Xaa Pro Ser Leu
1               5                   10                  15

Lys Ser Arg Val
            20

<210> SEQ ID NO 177
<211> LENGTH: 21
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (3)..(3)
<223> OTHER INFORMATION: Xaa = A, G, S, V or Y
<220> FEATURE:
<221> NAME/KEY: VARIANT
<222> LOCATION: (7)..(7)
<223> OTHER INFORMATION: Xaa = A, D, S or Y
<220> FEATURE:
<221> NAME/KEY: VARIANT
<222> LOCATION: (9)..(9)
<223> OTHER INFORMATION: Xaa = D, G or S
<220> FEATURE:
<221> NAME/KEY: VARIANT
<222> LOCATION: (10)..(10)
<223> OTHER INFORMATION: Xaa = S or T

<400> SEQUENCE: 177

Val Ser Xaa Ile Ser Gly Xaa Gly Xaa Xaa Thr Tyr Tyr Ala Asp Ser
1               5                   10                  15

Val Lys Gly Arg Phe
            20

<210> SEQ ID NO 178
<211> LENGTH: 15
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (3)..(3)
<223> OTHER INFORMATION: Xaa = E or G
<220> FEATURE:
<221> NAME/KEY: VARIANT
<222> LOCATION: (5)..(5)
<223> OTHER INFORMATION: Xaa = E or S
<220> FEATURE:
<221> NAME/KEY: VARIANT
<222> LOCATION: (6)..(6)
<223> OTHER INFORMATION: Xaa = D or T
<220> FEATURE:
<221> NAME/KEY: VARIANT
<222> LOCATION: (7)..(7)
<223> OTHER INFORMATION: Xaa = A, T or V
<220> FEATURE:
<221> NAME/KEY: VARIANT
<222> LOCATION: (9)..(9)
<223> OTHER INFORMATION: Xaa = A, I, L, T or V
<220> FEATURE:
<221> NAME/KEY: VARIANT
<222> LOCATION: (14)..(14)
<223> OTHER INFORMATION: Xaa = A, D or G

<400> SEQUENCE: 178
```

```
Ala Arg Xaa Gly Xaa Xaa Xaa Val Xaa Gly Asp Trp Phe Xaa Tyr
1               5                   10                  15
```

<210> SEQ ID NO 179
<211> LENGTH: 11
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Q or R
<220> FEATURE:
<221> NAME/KEY: VARIANT
<222> LOCATION: (5)..(5)
<223> OTHER INFORMATION: Xaa = D, G or S
<220> FEATURE:
<221> NAME/KEY: VARIANT
<222> LOCATION: (6)..(6)
<223> OTHER INFORMATION: Xaa = I or V
<220> FEATURE:
<221> NAME/KEY: VARIANT
<222> LOCATION: (7)..(7)
<223> OTHER INFORMATION: Xaa = G, R, S or T
<220> FEATURE:
<221> NAME/KEY: VARIANT
<222> LOCATION: (8)..(8)
<223> OTHER INFORMATION: Xaa = P, R, S or T
<220> FEATURE:
<221> NAME/KEY: VARIANT
<222> LOCATION: (9)..(9)
<223> OTHER INFORMATION: Xaa = A, D, F, S, V or Y
<220> FEATURE:
<221> NAME/KEY: VARIANT
<222> LOCATION: (10)..(10)
<223> OTHER INFORMATION: Xaa = L or V
<220> FEATURE:
<221> NAME/KEY: VARIANT
<222> LOCATION: (11)..(11)
<223> OTHER INFORMATION: Xaa = A, G or N

<400> SEQUENCE: 179

```
Xaa Ala Ser Gln Xaa Xaa Xaa Xaa Xaa Xaa Xaa
1               5                   10
```

<210> SEQ ID NO 180
<211> LENGTH: 9
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = A or D
<220> FEATURE:
<221> NAME/KEY: VARIANT
<222> LOCATION: (4)..(4)
<223> OTHER INFORMATION: Xaa = N, S or T
<220> FEATURE:
<221> NAME/KEY: VARIANT
<222> LOCATION: (5)..(5)
<223> OTHER INFORMATION: Xaa = L or R
<220> FEATURE:
<221> NAME/KEY: VARIANT
<222> LOCATION: (6)..(6)
<223> OTHER INFORMATION: Xaa = A, E or Q
<220> FEATURE:
<221> NAME/KEY: VARIANT
<222> LOCATION: (7)..(7)
<223> OTHER INFORMATION: Xaa = S or T
<220> FEATURE:
<221> NAME/KEY: VARIANT
<222> LOCATION: (9)..(9)
<223> OTHER INFORMATION: Xaa = I or V

```
<400> SEQUENCE: 180

Xaa Ala Ser Xaa Xaa Xaa Xaa Gly Xaa
1               5

<210> SEQ ID NO 181
<211> LENGTH: 10
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (5)..(5)
<223> OTHER INFORMATION: Xaa = A, G, S or Y
<220> FEATURE:
<221> NAME/KEY: VARIANT
<222> LOCATION: (7)..(7)
<223> OTHER INFORMATION: Xaa = Q, S or Y
<220> FEATURE:
<221> NAME/KEY: VARIANT
<222> LOCATION: (8)..(8)
<223> OTHER INFORMATION: Xaa = I, L, T or Y
<220> FEATURE:
<221> NAME/KEY: VARIANT
<222> LOCATION: (9)..(9)
<223> OTHER INFORMATION: Xaa = I, S, V or W

<400> SEQUENCE: 181

Tyr Cys Gln Gln Xaa Tyr Xaa Xaa Xaa Thr
1               5                   10

<210> SEQ ID NO 182
<211> LENGTH: 11
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (3)..(3)
<223> OTHER INFORMATION: Xaa = E or Q
<220> FEATURE:
<221> NAME/KEY: VARIANT
<222> LOCATION: (5)..(5)
<223> OTHER INFORMATION: Xaa = P, S or Y
<220> FEATURE:
<221> NAME/KEY: VARIANT
<222> LOCATION: (6)..(6)
<223> OTHER INFORMATION: Xaa = D, L, S, T or Y
<220> FEATURE:
<221> NAME/KEY: VARIANT
<222> LOCATION: (7)..(7)
<223> OTHER INFORMATION: Xaa = D, E, H, S or T
<220> FEATURE:
<221> NAME/KEY: VARIANT
<222> LOCATION: (8)..(8)
<223> OTHER INFORMATION: Xaa = D, L, T or W
<220> FEATURE:
<221> NAME/KEY: VARIANT
<222> LOCATION: (10)..(10)
<223> OTHER INFORMATION: Xaa = L, P, R or V

<400> SEQUENCE: 182

Tyr Cys Xaa Gln Xaa Xaa Xaa Xaa Pro Xaa Thr
1               5                   10
```